US008507473B2

(12) United States Patent
Boatman et al.

(10) Patent No.: US 8,507,473 B2
(45) Date of Patent: Aug. 13, 2013

(54) 3H-IMIDAZO[4,5-B]PYRIDIN-5-OL DERIVATIVES USEFUL IN THE TREATMENT OF GPR81 RECEPTOR DISORDERS

(75) Inventors: P. Douglas Boatman, San Diego, CA (US); Benjamin R. Johnson, San Diego, CA (US); Jae-Kyu Jung, San Diego, CA (US); Michelle Kasem, Chula Vista, CA (US); Thomas O. Schrader, San Diego, CA (US); Philip J. Skinner, San Diego, CA (US); Steven Colletti, Princeton Junction, NJ (US)

(73) Assignees: Arena Pharmaceuticals, Inc., San Diego, CA (US); Merck Sharp & Dohme Corp., Rahway, NJ (US)

( * ) Notice: Subject to any disclaimer, the term of this patent is extended or adjusted under 35 U.S.C. 154(b) by 335 days.

(21) Appl. No.: 13/063,305

(22) PCT Filed: Sep. 10, 2009

(86) PCT No.: PCT/US2009/005083
§ 371 (c)(1),
(2), (4) Date: Mar. 10, 2011

(87) PCT Pub. No.: WO2010/030360
PCT Pub. Date: Mar. 18, 2010

(65) Prior Publication Data
US 2011/0172209 A1    Jul. 14, 2011

Related U.S. Application Data

(60) Provisional application No. 61/191,670, filed on Sep. 11, 2008.

(51) Int. Cl.
| C07D 471/04 | (2006.01) |
| A61K 31/437 | (2006.01) |
| A61K 31/55 | (2006.01) |
| A61P 3/06 | (2006.01) |
| A61P 3/10 | (2006.01) |
| A61P 9/10 | (2006.01) |

(52) U.S. Cl.
USPC ....... 514/217.07; 514/303; 546/118; 540/597

(58) Field of Classification Search
USPC ............. 514/217.07, 303; 546/118; 540/597
See application file for complete search history.

(56) References Cited

U.S. PATENT DOCUMENTS

| 2004/0180885 A1 | 9/2004 | Torisu et al. |
| 2005/0222216 A1 | 10/2005 | Iwahashi et al. |
| 2006/0069117 A1 | 3/2006 | Rault et al. |
| 2006/0194864 A1 | 8/2006 | Torisu et al. |

FOREIGN PATENT DOCUMENTS

| EP | 1 305 286 | 12/2004 |
| EP | 1 878 724 | 1/2008 |
| FR | 2 846 656 | 4/2004 |
| WO | WO 99/16755 | 4/1999 |
| WO | WO 01/66520 | 9/2001 |
| WO | WO 01/79169 | 10/2001 |
| WO | WO 02/094830 | 11/2002 |
| WO | WO 03/022814 | 3/2003 |
| WO | 03057696 | * 7/2003 |
| WO | WO 03/062200 | 7/2003 |
| WO | WO 03/078409 | 9/2003 |
| WO | WO 2004/103370 | 12/2004 |
| WO | WO 2008/063321 | 5/2008 |

OTHER PUBLICATIONS

*Bioreversible Carriers in Drug Design*, ed. Edward B. Roche, American Pharmaceutical Association and Pergamon Press, 1987.
Collier, et al., *J. Labelled Compd. Radiopharm*, 1999, 42, S264-S266.
Delporte, et al.; *Biochem J*, (Jul. 2002), 367:677-85.
Gabriel et al., *Assay and Drug Development Technologies*, 1:291-303, 2003.
Goodman and Gilman's Pharmacological Basis of Therapeutics, Editors Harmon JG and Limbird LE, chapter 36, Mahley RW and Bersot TP (2001), pp. 971-1002.
Greene, et al.; *Protecting Groups in Organic Synthesis*; 3rd Edition, 1999 [Wiley].
Guillory, *Polymorphism in Pharmaceutical Solids;* Generation of Polymorphs, Hydrates, Solvates, and Amorphous Solids; ed. Harry G. Brittan, vol. 95, Marcel Dekker, Inc. NY, 1999.
Higuchi, et al., *Pro-drugs as Novel Delivery Systems*, vol. 14 of the A.C.S. Symposium Series.
*J. Med. Chem.*, 1997, 40, 1808.
*Journal of Pharmaceutical Sciences*, 66:1-19(1977).
Lago et al., *Cytokine Growth Factor Rev*, Jun.-Aug. 2007; 18(3-4):313-35.

(Continued)

*Primary Examiner* — Niloofar Rahmani
(74) *Attorney, Agent, or Firm* — Fish & Richardson P.C.; Lyle W. Spruce

(57) ABSTRACT

The present invention is directed to certain 3H-imidazo[4,5-b]pyridin-5-ol derivatives of Formula (Ia) and pharmaceutically acceptable salts thereof, which exhibit useful pharmacological properties, for example, as agonists of the GPR81 receptor. Also provided by the present invention are pharmaceutical compositions containing compounds of the invention, and methods of using the compounds and compositions of the invention in the treatment of GPR81 associated disorders, for example, dyslipidemia, atherosclerosis, atheromatous disease, hypertension, coronary heart disease, stroke, insulin resistance, impaired glucose tolerance, type 2 diabetes, syndrome X, obesity, psoriasis, rheumatoid arthritis, Crohn's disease, transplant rejection, multiple sclerosis, systemic lupus erythematosus, ulcerative colitis, type 1 diabetes and acne.

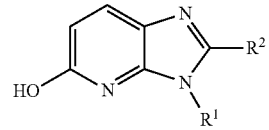

(Ia)

26 Claims, 7 Drawing Sheets

(56) References Cited

OTHER PUBLICATIONS

LeBas, et al., *J Labelled Compd. Radiopharm.*, 2001, 44, S280-S282.
Matsuda, et al.; *J. Biol. Chem.*, (Jul. 2002), 277:37487-91.
*Nature Medicine, Special Focus on Atherosclerosis,* (2002) 8:1209-1262.
Okamoto, et al., *Circulation,* (2002) 26:2767-70.
Remington, *The Science and Practice of Pharmacy,* 20th Edition, 2000, Lippincott Williams and Wilkins, (Editors: Gennaro et al.).
Staiger, et al., *Horm Metab Res,* (2002), 34:601-3.
Takemura et al., *Curr. Atheroscler. Rep.,* Sep. 2007;9(3):238-43.
Tomas, et al., *Proc. Natl. Acad. Sci. USA,* (Nov. 27, 2002).
Yamauchi, et al.; *Nat. Med.,* (2003) 8:1288-95.
Zaki, et al.; *The Synthesis of Imidazo [4,5-d]pyridines from a substituted Imidazole and Acyl or Sulfonyl Acetonitrile;* Tetrahedron 63; 2007; pp. 3745-3753.
Zhu, et al., *J. Org. Chem.,* 2002, 67, 943-948.

* cited by examiner

3H-IMIDAZO[4,5-B]PYRIDIN-5-OL DERIVATIVES USEFUL IN THE TREATMENT OF GPR81 RECEPTOR DISORDERS

This application is a §371 National Stage Application of International Application No. PCT/US2009/05083, filed Sep. 10, 2009, which claims the benefit of priority of U.S. Provisional Application No. 61/191,670, filed Sep. 11, 2008, each of which is incorporated herein by reference in its entirety.

FIELD OF THE INVENTION

The present invention relates to certain 3H-imidazo[4,5-b]pyridin-5-ol derivatives of Formula (Ia) and pharmaceutically acceptable salts thereof, which exhibit useful pharmacological properties, for example, as agonists of the GPR81 receptor. Also provided by the present invention are pharmaceutical compositions containing compounds of the invention, and methods of using the compounds and compositions of the invention in the treatment of GPR81-associated disorders, for example, dyslipidemia, atherosclerosis, atheromatous disease, hypertension, coronary heart disease, stroke, insulin resistance, impaired glucose tolerance, type 2 diabetes, syndrome X, obesity, psoriasis, rheumatoid arthritis, Crohn's disease, transplant rejection, multiple sclerosis, systemic lupus erythematosus, ulcerative colitis, type 1 diabetes and acne.

BACKGROUND OF THE INVENTION

Atherosclerosis is a process where deposits of fatty substances, cholesterol and other substances build up in the inner lining of an artery. This buildup is called plaque. Plaques that rupture cause blood clots to form that can block blood flow to the heart (heart attack) or the brain (stroke). Heart attack is the number one cause of death for both men and women in the United States and stroke is the number three cause of death [see, for example, *Nature Medicine, Special Focus on Atherosclerosis*, (2002) 8:1209-1262]. Abnormally high levels of circulating lipids are a major predisposing factor in development of atherosclerosis. Elevated levels of low density lipoprotein (LDL) cholesterol, elevated levels of triglycerides, or low levels of high density lipoprotein (HDL) cholesterol are, independently, risk factors for atherosclerosis and associated pathologies. In addition, high levels of plasma free fatty acids are associated with insulin resistance and type 2 diabetes.

Diabetes afflicts several million people worldwide. In the United States alone, there are more than 18 million diabetics, with 600,000 new cases diagnosed each year. People with diabetes are at higher risk for heart disease, blindness, kidney failure, infection, extremity amputations, and other chronic conditions. It is estimated that the direct medical expenditures and indirect expenditures attributable to diabetes in the United States were $132 billion in 2002. Taken together, diabetes complications are one of the nation's leading causes of death.

One strategy for decreasing LDL-cholesterol, increasing HDL-cholesterol, and decreasing plasma free fatty acids is to inhibit lipolysis in adipose tissue. This approach involves regulation of hormone sensitive lipase, which is the rate-limiting enzyme in lipolysis. Lipolytic agents increase cellular levels of cAMP, which leads to activation of hormone sensitive lipase within adipocytes. Agents that lower intracellular cAMP levels, by contrast, would be antilipolytic.

It is also worth noting that an increase in cellular levels of cAMP down-regulates the secretion of adiponectin from adipocytes [Delporte, M. L. et al. *Biochem J* (2002) July]. Reduced levels of plasma adiponectin have been associated with metabolic-related disorders, including atherosclerosis, coronary heart disease, insulin resistance and type 2 diabetes [Matsuda, M. et al. *J. Biol. Chem.* (2002) July and reviewed therein].

Niacin is also one of the oldest used drugs for the treatment of lipid-associated disorders. It is a valuable drug in that it favorably affects virtually lipid parameters [Goodman and Gilman's Pharmacological Basis of Therapeutics, editors Harmon J G and Limbird L E, Chapter 36, Mahley R W and Bersot T P (2001) pages 971-1002]. Unfortunately, the doses of niacin required to alter serum lipid levels can be quite large and at these dosages adverse side effects are frequent. Side effects can include intense cutaneous flushing, gastrointestinal disturbances, liver toxicity, and disruption of glucose metabolism and uric acid levels. Often, 30-40% of patients cease taking niacin treatment within days after initiating therapy. Statins are also commonly used to treat lipid-associated disorders. The side effects of statins include muscle pain, myopathy, rhabdomyolysis, serious liver problems and kidney problems.

Therapies do exist to treat diabetes, such as α-glucosidase inhibitors, biguanides, thiazolidinediones, meglitinides, sulfonylureas and exogenous insulin. However, these therapies have limited effectiveness and are associated with significant safety and tolerability issues such as risk for hypoglycemic episodes, weight gain, gastrointestinal disturbances and anemia. In addition, many of the treatment options require injection or multiple daily dosing which present compliance challenges.

Thus, there exists a need for the identification of antilipolytic agents for the treatment of metabolic-related disorders such as dyslipidemia, atherosclerosis and diabetes. The present invention satisfies this need and provides related advantages as well.

SUMMARY OF THE INVENTION

Figure 1:
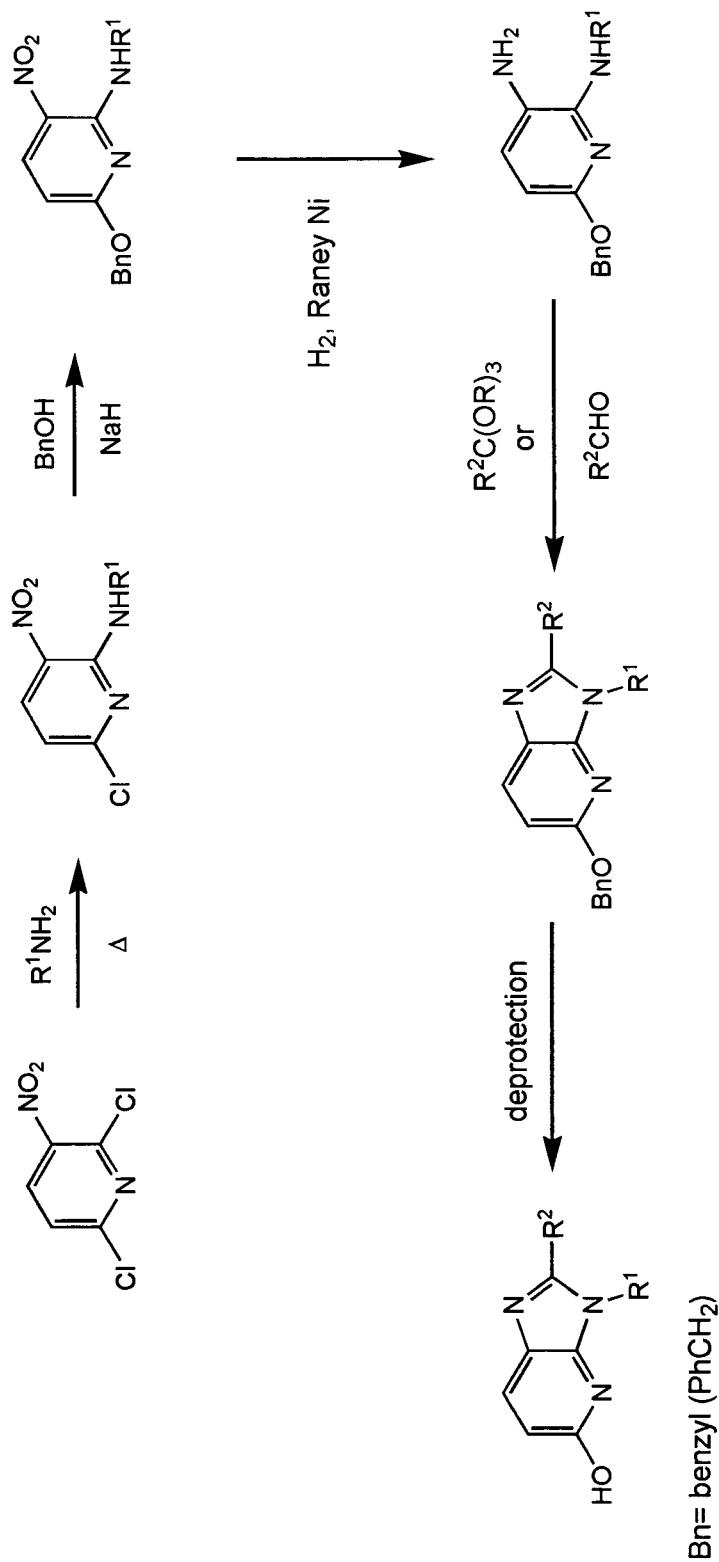
FIG. 1 shows a general method for the preparation of compounds of the present invention. The 2,6-dichloro-3-nitropyridine starting material undergoes one initial nucleophilic displacement with a primary amine, followed by a second nucleophilic displacement with benzyl alcohol. Following the reduction of the nitro group, the di-amino intermediate is condensed with formates or aldehydes to prepare compounds. Subsequent deprotection affords compounds of the present invention of formula (Ia).

The present invention relates to certain 3H-imidazo[4,5-b]pyridin-5-ol derivatives as shown in Formula (Ia) and pharmaceutically acceptable salts, solvates and hydrates thereof:

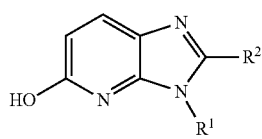

(Ia)

wherein $R^1$ is aryl, heteroaryl, $C_3$-$C_{10}$ cycloalkyl, or heterocyclyl, each optionally substituted with 1, 2, or 3 substitutents independently selected from the group consisting of $C_1$-$C_6$ alkoxy, $C_1$-$C_6$ alkoxycarbonyl, $C_1$-$C_6$ alkyl, $C_1$-$C_6$ alkylthio, aryl, $C_3$-$C_6$ cycloalkyl, halogen, $C_1$-$C_6$ haloalkoxy, $C_1$-$C_6$ haloalkyl, $C_1$-$C_6$ haloalkylthio, hydroxyl, nitro, and oxo, wherein $C_1$-$C_6$ alkyl is optionally substituted with aryl, or two adjacent substitutents together with the atoms to which they are both bonded form a five-membered cycloalkyl or a five-membered heterocyclyl; and $R^2$ is H, $C_1$-$C_6$ alkyl, $C_1$-$C_6$ alkylthio, amino, aryl, $C_3$-$C_6$ cycloalkyl, or halogen.

One aspect of the present invention encompasses pharmaceutical compositions comprising a compound of the present invention and a pharmaceutically acceptable carrier.

One aspect of the present invention encompasses methods for modulating the activity of a GPR81 receptor by contacting the receptor with a compound, as described herein, or a pharmaceutical composition thereof.

One aspect of the present invention encompasses methods for aganizing the activity of a GPR81 receptor by contacting the receptor with a compound, as described herein, or a pharmaceutical composition thereof.

One aspect of the present invention encompasses methods for aganizing the activity of a GPR81 receptor by contacting the receptor with a compound, as described herein, or a pharmaceutical composition thereof.

One aspect of the present invention encompasses methods for the treatment of a GPR81 receptor related disorder in an individual, comprising administering to the individual in need thereof, a therapeutically effective amount of a compound or a pharmaceutical composition as described herein.

One aspect of the present invention encompasses methods for the treatment of a metabolic-related disorder in an individual, comprising administering to the individual in need thereof, a therapeutically effective amount of a compound or a pharmaceutical composition as described herein.

In some embodiments, the metabolic-related disorder is selected from the group consisting of dyslipidemia, atherosclerosis, atheromatous disease, hypertension, coronary heart disease, stroke, insulin resistance, impaired glucose tolerance, type 2 diabetes, syndrome X, and obesity.

One aspect of the present invention encompasses methods for the treatment of psoriasis, rheumatoid arthritis, Crohn's disease, transplant rejection, multiple sclerosis, systemic lupus erythematosus, ulcerative colitis, type 1 diabetes, or acne in an individual, comprising administering to the individual in need thereof, a therapeutically effective amount of a compound or a pharmaceutical composition as described herein.

One aspect of the present invention is the use of a compound, as described herein, in the manufacture of a medicament for the treatment of a GPR81 receptor related disorder.

One aspect of the present invention is the use of a compound, as described herein, in the manufacture of a medicament for the treatment of a metabolic-related disorder.

One aspect of the present invention is the use of a compound, as described herein, in the manufacture of a medicament for the treatment of an inflammatory disorder.

One aspect of the present invention is the use of a compound, as described herein, in the manufacture of a medicament for the treatment of an autoimmune disorder.

One aspect of the present invention encompasses compounds, as described herein, for use in a method of treatment of the human or animal body by therapy.

One aspect of the present invention encompasses compounds, as described herein, for use in a method of treatment of a GPR81 receptor related disorder.

One aspect of the present invention encompasses compounds, as described herein, for use in a method of treatment of a metabolic-related disorder.

One aspect of the present invention encompasses compounds, as described herein, for use in a method of treatment of dyslipidemia, atherosclerosis, atheromatous disease, hypertension, coronary heart disease, stroke, insulin resistance, impaired glucose tolerance, type 2 diabetes, syndrome X, or obesity.

One aspect of the present invention encompasses compounds, as described herein, for use in a method of treatment of psoriasis, rheumatoid arthritis, Crohn's disease, transplant rejection, multiple sclerosis, systemic lupus erythematosus, ulcerative colitis, type 1 diabetes, or acne.

One aspect of the present invention encompasses processes for preparing pharmaceutical compositions comprising admixing a compound, as described herein, and a pharmaceutically acceptable carrier.

These and other aspects of the invention disclosed herein will be set forth in greater detail as the patent disclosure proceeds.

DETAILED DESCRIPTION OF THE INVENTION

Definitions

For clarity and consistency, the following definitions will be used throughout this patent document.

The term "agonist" is intended to mean a moiety that interacts with and activates a G-protein-coupled receptor, such as the GPR81 receptor, and can thereby initiate a physiological or pharmacological response characteristic of that receptor. For example, an agonist activites an intracellular response upon binding to the receptor, or enhances GTP binding to a membranes.

The term "antagonist" is intended to mean a moiety that competitively binds to the receptor at the same site as an agonist (for example, the endogenous ligand), but which does not activate the intracellular response initiated by the active form of the receptor and can thereby inhibit the intracellular responses by an agonist or partial agonist. An antagonist does not diminish the baseline intracellular response which is obroad served in the abroad sence of an agonist or partial agonist.

The term "hydrate" as used herein means a compound of the invention or a salt thereof, that further includes a stoichiometric or non-stoichiometric amount of water bound by non-covalent intermolecular forces.

The term "solvate" as used herein means a compound of the invention or a salt thereof, that further includes a stoichiometric or non-stoichiometric amount of a solvent bound by non-covalent intermolecular forces. Preferred solvents are non-toxic and/or acceptable for administration to humans.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "individual" is intended to mean any animal, including mammals, preferably mice, rats, other rodents, rabbits, dogs, cats, swine, cattle, sheep, horses, or primates and most preferably humans.

The term "inverse agonist" is intended to mean a moiety that binds to the endogenous form of the receptor or to the constitutively activated form of the receptor and which inhibits the baseline intracellular response initiated by the active form of the receptor below the normal base level of activity which is obroad served in the abroad sence of an agonist or partial agonist, or decrease GTP binding to a membrane. In some embodiments, the baseline intracellular response is inhibited in the presence of the inverse agonist by at least 30%, by at least 50%, or by at least 75%, as compared with the baseline response in the abroad sence of the inverse agonist.

The term "modulate or modulating" is intended to mean an increase or decrease in the amount, quality, response or effect of a particular activity, function or molecule.

The term "pharmaceutical composition" is intended to mean a composition comprising at least one active ingredient, including but not limited to, salts, solvates and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" is intended to mean the amount of active compound or pharmaceutical agent that elicits the biological or medicinal response in a tissue, system, animal, individual or human that is being sought by a researcher, veterinarian, medical doctor or other clinician or caregiver, or by an individual, which includes one or more of the following:

(1) Preventing the disease, for example, preventing a disease, condition or disorder in an individual that may be predisposed to the disease, condition or disorder but does not yet experience or display the pathology or symptomatology of the disease, (2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

Chemical Group, Moiety or Radical

The term "$C_1$-$C_6$ alkoxy" is intended to mean a $C_1$-$C_6$ alkyl radical, as defined herein, attached directly to an oxygen atom, some embodiments are 1 to 5 carbons, some embodiments are 1 to 4 carbons, some embodiments are 1 to 3 carbons and some embodiments are 1 or 2 carbons. Examples include methoxy, ethoxy, n-propoxy, isopropoxy, n-butoxy, tert-butoxy, isobutoxy, sec-butoxy and the like.

The term "$C_1$-$C_6$ alkoxycarbonyl" is intended to mean a $C_1$-$C_6$ alkyl ester of a carboxylic acid, wherein the alkyl group is as defined herein. Examples include, but are not limited to, carbomethoxy [i.e., —C(=O)OCH$_3$], carboethoxy, carbopropoxy, carboisopropoxy, carbobutoxy, carbo-sec-butoxy, carbo-isobutoxy, carbo-tert-butoxy, carbo-n-pentoxy, carbo-isopentoxy, carbo-tert-pentoxy, carbo-neo-pentoxy, carbo-n-hexyloxy and the like.

The term "$C_1$-$C_6$ alkyl" is intended to mean a straight or branched carbon radical containing 1 to 6 carbons. Some embodiments are 1 to 5 carbons, some embodiments are 1 to 4 carbons, some embodiments are 1 to 3 carbons and some embodiments are 1 or 2 carbons. Examples of an alkyl include, but not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl, and the like.

The term "$C_1$-$C_6$ alkylthio" is intended to mean a $C_1$-$C_6$ alkyl radical attached to a sulfur atom (i.e., —S—) wherein the alkyl radical has the same definition as described herein. Examples include, but are not limited to, methylsulfanyl (i.e., CH$_3$S—), ethylsulfanyl, n-propylsulfanyl, isopropylsulfanyl, n-butylsulfanyl, sec-butylsulfanyl, isobutylsulfanyl, tert-butylsulfanyl, and the like.

The term "amino" is intended to mean the group —NH$_2$.

The term "aryl" is intended to mean an aromatic ring radical containing 6 to 10 ring carbons. Examples include phenyl, indenyl, dihydroindenyl, naphthalenyl, and the like. In some embodiments aryl is phenyl, and naphthalenyl.

The term "$C_3$-$C_{10}$ cycloalkyl" is intended to mean a saturated ring radical containing 3 to 10 carbons. Some embodiments contain 3 to 6 carbons; some embodiments contain 3 to 5 carbons; some embodiments contain 5 to 7 carbons; some embodiments contain 3 to 4 carbons. It is understood that "$C_3$-$C_{10}$ cycloalkyl" embraces mono-, di- and tri-cyclic ring radicals. Examples include 1-adamantyl, 2-adamantyl, bicyclo[2.2.1]heptan-2-yl, bicyclo[2.2.2]octan-2-yl cyclopropyl, cyclobutyl, cyclopentyl, cyclohexyl, cycloheptyl, and the like The term "$C_1$-$C_6$ haloalkoxy" is intended to mean a $C_1$-$C_6$ haloalkyl, as defined herein, which is directly attached to an oxygen atom. Examples include, but are not limited to, difluoromethoxy, trifluoromethoxy, 2,2,2-trifluoroethoxy, pentafluoroethoxy and the like.

The term "$C_1$-$C_6$ haloalkyl" is intended to mean an $C_1$-$C_6$ alkyl group, as defined herein, wherein the alkyl is substituted with one halogen up to fully substituted and a fully substituted $C_1$-$C_6$ haloalkyl can be represented by the formula $C_aL_{2a+1}$ wherein L is a halogen and "a" is 1, 2, 3, 4, 5 or 6. When more than one halogen is present then they may be the same or different and selected from the group consisting of F, Cl, Br and I, some embodiments are 1 to 5 carbons, some embodiments are 1 to 4 carbons, some embodiments are 1 to 3 carbons and some embodiments are 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like.

The term "$C_1$-$C_6$ haloalkylthio" is intended to mean a $C_1$-$C_6$ haloalkyl radical attached to a sulfur atom (i.e., —S—) wherein the haloalkyl radical has the same definition as described herein. Examples include, but are not limited to, trifluoromethylsulfanyl (i.e., $CF_3S$—), difluoromethylsulfanyl, 2,2-difluoroethylsulfanyl, 2,2-difluoropropylsulfanyl, and the like.

The term "halogen" or "halo" is intended to mean to a fluoro, chloro, bromo or iodo group.

The term "heteroaryl" is intended to mean an aromatic ring system containing 5 to 14 aromatic ring atoms that may be a single ring, two fused rings or three fused rings wherein at least one aromatic ring atom is a heteroatom selected from, for example, but not limited to, the group consisting of O, S and N wherein the N can be optionally substituted with H, $C_1$-$C_4$ acyl or $C_1$-$C_4$ alkyl. Some embodiments contain 5 or 6 ring atoms for example furanyl, thienyl, pyrrolyl, imidazolyl, oxazolyl, thiazolyl, isoxazolyl, pyrazolyl, isothiazolyl, oxadiazolyl, triazolyl, thiadiazolyl, pyridinyl, pyrazinyl, pyrimidinyl, pyridazinyl, and triazinyl, and the like. Some embodiments contain 8 to 14 ring atoms for example quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl, phenazinyl, phenothiazinyl, phenoxazinyl, benzoxazolyl, benzothiazolyl, 1H-benzimidazolyl, imidazopyridinyl, benzothienyl, benzofuranyl, and isobenzofuran and the like The term "heterocyclic" or "heterocyclyl" is intended to mean a non-aromatic carbon ring containing 3 to 8 ring atoms wherein one, two or three ring atoms are heteroatoms selected from, for example, the group consisting of O, S and NH, wherein the N is optionally substituted with $C_1$-$C_4$ alkyl or as described herein and S is optionally substituted with 1 or 2 oxygens. In some embodiments, the nitrogen is optionally substituted with $C_1$-$C_4$ acyl or $C_1$-$C_4$ alkyl, and ring carbon atoms are optionally substituted with oxo or a thiooxo thus forming a carbonyl or thiocarbonyl group. The heterocyclic group can be attached/bonded to any available ring atom, for example, ring carbon, ring nitrogen and the like. In some embodiments the heterocyclic group is a 3-, 4-, 5-, 6- or 7-membered ring. Examples of a heterocyclic group include, but are not limited to, aziridin-1-yl, aziridin-2-yl, azetidin-1-yl, azetidin-2-yl, azetidin-3-yl, piperidin-1-yl, piperidin-2-yl, piperidin-3-yl, piperidin-4-yl, morpholin-2-yl, morpholin-3-yl, morpholin-4-yl, piperzin-1-yl, piperzin-2-yl, piperzin-3-yl, piperzin-4-yl, pyrrolidin-1-yl, pyrrolidin-2-yl, pyrrolidin-3-yl, [1,3]-dioxolan-2-yl, 1,3-dioxol-2-yl, 1,3-dioxol-4-yl, thiomorpholin-4-yl, 1,4-oxazepan-4-yl, 1,1-dioxothiomorpholin-4-yl, azepan-1-yl, azepan-2-yl, azepan-3-yl, azepan-4-yl, tetrahydrofuran-2-yl, tetrahydrofuran-3-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, and the like.

The term "hydroxyl" is intended to mean the group —OH.

The term "naphthalenyl" is intended to mean:

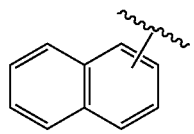

The term "nitro" is intended to mean the group —$NO_2$.

The term "oxo" is intended to mean a double-bonded oxygen atom, thus an "oxo" group bonded together with a carbon atom forms a carbonyl group.

The term "phenyl" is intended to mean:

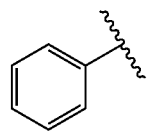 [SMILES: *c1ccccc1]

Compounds of the Invention:

One aspect of the present invention pertains to certain compounds of Formula (Ia) and pharmaceutically acceptable salts, solvates and hydrates thereof:

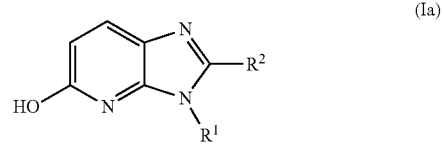

(Ia)

wherein:

$R^1$ and $R^2$ have the same definitions as described herein, supra and infra.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., $R^1$ and $R^2$) contained within the generic chemical formulae described herein, for example, (Ia, etc.) are specifically embraced by the present invention just as if each and every combination was individually explicitly recited, to the extent that such combinations embrace compounds that result in stable compounds (i.e., compounds that can be isolated, characterized and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valance of substitution; for example, a methyl group can be substituted with 1, 2, or 3 substitutents, a methylene group can be substituted by 1 or 2 substitutents, a phenyl group can be substituted with 1, 2, 3, 4, or 5 substitutents, a naphthalenyl group can be substituted with 1, 2, 3, 4, 5, 6, or 7 substitutents and the like. Likewise, "substituted with one or more substitutents" refers to the substitution of a group with one substituent up to the total number of substitutents physically allowed by the group. Further, when a group is substituted with more than one group they can be identical or they can be different.

Compounds of the invention also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

Compounds of the invention also include all isotopes of atoms occurring in the intermediates and/or final compounds. Isotopes include those atoms having the same atomic number but different mass numbers. For example, isotopes of hydrogen include deuterium and tritium.

It is understood and appreciated that compounds of Formula (Ia) and formulae related thereto may have one or more chiral centers and therefore can exist as enantiomers and/or diastereomers. The invention is understood to extend to and embrace all such enantiomers, diastereomers and mixtures thereof, including but not limited to racemates. It is understood that compounds of Formula (Ia) and formulae used throughout this disclosure are intended to represent all individual enantiomers and mixtures thereof, unless stated or shown otherwise.

The Group $R^1$

In some embodiments, $R^1$ is aryl, heteroaryl, $C_3$-$C_{10}$ cycloalkyl, or heterocyclyl, each optionally substituted with 1, 2, or 3 substitutents independently selected from the group consisting of $C_1$-$C_6$ alkoxy, $C_1$-$C_6$ alkoxycarbonyl, $C_1$-$C_6$ alkyl, $C_1$-$C_6$ alkylthio, aryl, $C_3$-$C_6$ cycloalkyl, halogen, $C_1$-$C_6$ haloalkoxy, $C_1$-$C_6$ haloalkyl, $C_1$-$C_6$ haloalkylthio, hydroxyl, nitro, and oxo, wherein $C_1$-$C_6$ alkyl is optionally substituted with aryl; or two adjacent substitutents together with the atoms to which they are both bonded form a five-membered cycloalkyl or a five-membered heterocyclyl.

In some embodiments, $R^1$ is phenyl or naphthalenyl, optionally substituted with 1, 2, or 3 substitutents independently selected from the group consisting of $C_1$-$C_6$ alkoxy, $C_1$-$C_6$ alkyl, $C_1$-$C_6$ alkylthio, aryl, $C_3$-$C_6$ cycloalkyl, halogen, $C_1$-$C_6$ haloalkoxy, $C_1$-$C_6$ haloalkyl, $C_1$-$C_6$ haloalkylthio, and nitro, and wherein $C_1$-$C_6$ alkyl is optionally substituted with aryl; or two adjacent substitutents together with the atoms to which they are both bonded form a five-membered cycloalkyl or a five-membered heterocyclyl.

In some embodiments, $R^1$ is phenyl or naphthalenyl, optionally substituted with 1, 2, or 3 substitutents independently selected from the group consisting of methoxy, methyl, ethyl, isopropyl, cyclopropyl, methylthio, phenyl, bromo, chloro, fluoro, iodo, trifluoromethoxy, trifluoromethylthio, and nitro.

In some embodiments, $R^1$ is phenyl, optionally substituted with 1, 2, or 3 substitutents independently selected from the group consisting of methoxy, methyl, ethyl, isopropyl, cyclopropyl, methylthio, phenyl, bromo, chloro, fluoro, iodo, trifluoromethoxy, trifluoromethyl, trifluoromethylthio, and nitro.

In some embodiments, $R^1$ is selected from the group consisting of 2-(methylthio)phenyl, 2-(trifluoromethoxy)phenyl, 2-(trifluoromethylthio)phenyl, 2,3,4-trichlorophenyl, 2,3-dichlorophenyl, 2,3-difluorophenyl, 2,3-dihydro-1H-inden-4-yl, 2,3-dihydro-1H-inden-5-yl, 2,3-dimethylphenyl, 2,3-diphenyl, 2,4,5-trichlorophenyl, 2,4-bis(trifluoromethyl)phenyl, 2,4-dichlorophenyl, 2,4-dimethylphenyl, 2,5-dimethylphenyl, 2,6-dichlorophenyl, 2-bromo-3-methylphenyl, 2-bromophenyl, 2-chloro-3-fluorophenyl, 2-chlorophenyl, 2-cyclopropylphenyl, 2-ethylphenyl, 2-fluoro-3-(trifluoromethyl)phenyl, 2-fluoro-3-methylphenyl, 2-fluorophenyl, 2-isopropylphenyl, 2-methoxyphenyl, 2-nitrophenyl, 3,4-dimethylphenyl, 3,5-dimethylphenyl, 3-bromo-2-(trifluoromethyl)phenyl, 3-chloro-2-fluorophenyl, 3-chloro-2-methylphenyl, 3-chlorophenyl, 3-fluoro-2-(trifluoromethyl)phenyl, 3-fluoro-2-methylphenyl, 4-benzylphenyl, 4-bromo-2-(trifluoromethyl)phenyl, 4-bromo-2-methylphenyl, 4-bromo-5-chloro-2-methylphenyl, 4-bromophenyl, 4-chloro-2-(trifluoromethyl)phenyl, 4-ethylphenyl, 4-fluoro-2-(trifluoromethyl)phenyl, 4-fluoro-2-methylphenyl, 4-fluorophenyl, 4-methoxyphenyl, 5-chloro-2-methylphenyl, benzo[d][1,3]dioxol-5-yl, biphenyl-2-yl, o-tolyl, phenyl, and p-tolyl.

In some embodiments, $R^1$ is naphthalenyl, optionally substituted with $C_1$-$C_6$ alkyl, or halogen.

In some embodiments, $R^1$ is naphthalenyl, optionally substituted with methyl or chloro.

In some embodiments, $R^1$ is selected from the group consisting of 2-methylnaphthalen-1-yl, 4-chloronaphthalen-1-yl, and naphthalen-1-yl.

In some embodiments, $R^1$ is heteroaryl, optionally substituted with halogen.

In some embodiments, $R^1$ is pyridinyl or thienyl, each optionally substituted with halogen. It is understood that thienyl encompasses thiophen-2-yl, and thiophen-3-yl. For example compound 24.

In some embodiments, $R^1$ is pyridinyl or thienyl, each optionally substituted with chloro.

In some embodiments, $R^1$ is 3-chloropyridin-4-yl or thiophen-3-yl.

In some embodiments, $R^1$ is $C_3$-$C_{10}$ cycloalkyl, optionally substituted with 1 or 2 substitutents independently selected from the group consisting of $C_1$-$C_6$ alkyl, halogen, hydroxyl, and oxo.

In some embodiments, $R^1$ is $C_3$-$C_{10}$ cycloalkyl, optionally substituted with 1 or 2 substitutents independently selected from the group consisting of ethyl, methyl, fluoro, hydroxyl, and oxo.

In some embodiments, $R^1$ is selected from the group consisting of 1-ethylcyclohexyl, 1-methylcyclohexyl, 2,2-difluorocycloheptyl, 2-hydroxycycloheptyl, 2-methylcyclohexyl, 2-oxocyclohexyl, 4-hydroxycyclohexyl, adamant-1-yl, bicyclo[2.2.1]heptan-2-yl, cyclobutyl, cycloheptanon-2-yl, cycloheptyl, cyclohexyl, cyclooctyl, and cyclopentyl.

In some embodiments, $R^1$ is heterocyclyl optionally substituted with $C_1$-$C_6$ alkoxycarbonyl.

In some embodiments, $R^1$ is selected from the group consisting of azepanyl, tetrahydro-2H-pyranyl, and tetrahydro-2H-thiopyranyl each optionally substituted with tert-butoxycarbonyl.

In some embodiments, $R^1$ is selected from the group consisting of 1-(tert-butoxycarbonyl)azepan-4-yl, tetrahydro-2H-pyran-4-yl, and tetrahydro-2H-thiopyran-4-yl.

The Group $R^2$

In some embodiments, $R^2$ is H, $C_1$-$C_6$ alkyl, $C_1$-$C_6$ alkylthio, amino, aryl, $C_3$-$C_6$ cycloalkyl, or halogen.

In some embodiments, $R^2$ is selected from the group consisting of H, amino, bromo, chloro, cyclopropyl, methyl, methylthio, phenyl, and n-propyl.

In some embodiments, $R^2$ is H.
In some embodiments, $R^2$ is amino.
In some embodiments, $R^2$ is bromo.
In some embodiments, $R^2$ is chloro.
In some embodiments, $R^2$ is cyclopropyl.
In some embodiments, $R^2$ is methyl.
In some embodiments, $R^2$ is methylthio.
In some embodiments, $R^2$ is phenyl.
In some embodiments, $R^2$ is n-propyl.

Certain Combinations

Some embodiments of the present invention pertain to compounds of Formula (Ia) and pharmaceutically acceptable salts, solvates and hydrates thereof:
wherein:
$R^1$ is aryl, optionally substituted with 1, 2, or 3 substitutents independently selected from the group consisting of $C_1$-$C_6$ alkoxy, $C_1$-$C_6$ alkyl, $C_1$-$C_6$ alkylthio, aryl, $C_3$-$C_6$ cycloalkyl, halogen, $C_1$-$C_6$ haloalkoxy, $C_1$-$C_6$ haloalkyl, $C_1$-$C_6$ haloalkylthio, and nitro, and wherein $C_1$-$C_6$ alkyl is optionally substituted with aryl, or
two adjacent substitutents together with the atoms to which they are both bonded form a five-membered cycloalkyl or a five-membered heterocyclyl.
$R^2$ is H, $C_1$-$C_6$ alkyl, $C_1$-$C_6$ alkylthio, amino, aryl, $C_3$-$C_6$ cycloalkyl, or halogen.

Some embodiments of the present invention pertain to compounds of Formula (Ia) and pharmaceutically acceptable salts, solvates and hydrates thereof:
wherein:
$R^1$ is selected from the group consisting of phenyl, naphthalenyl, pyridinyl, thienyl, adamantyl, cyclobutyl, cycloheptyl, cyclohexyl, cyclooctyl, cyclopentyl, azepanyl, tetrahydro-2H-pyranyl, and tetrahydro-2H-thiopyranyl, each optionally substituted with 1, 2, or 3 substitutents independently selected from the group consisting of tert-butoxycarbonyl, methoxy, methyl, ethyl, isopropyl, cyclopropyl, methylthio, phenyl, bromo, chloro, fluoro, hydroxyl, iodo, oxo, trifluoromethoxy, trifluoromethyl, trifluoromethylthio, and nitro; and
$R^2$ is H, amino, bromo, chloro, cyclopropyl, methyl, methylthio, phenyl, and n-propyl.

Some embodiments of the present invention pertain to compounds of Formula (Ia) and pharmaceutically acceptable salts, solvates and hydrates thereof:
wherein:
$R^1$ is selected from the group consisting of 2-(methylthio) phenyl, 2-(trifluoromethoxy)phenyl, 2-(trifluoromethylthio) phenyl, 2,3,4-trichlorophenyl, 2,3-dichlorophenyl, 2,3-difluorophenyl, 2,3-dihydro-1H-inden-4-yl, 2,3-dihydro-1H-inden-5-yl, 2,3-dimethylphenyl, 2,3-diphenyl, 2,4,5-trichlorophenyl, 2,4-bis(trifluoromethyl)phenyl, 2,4-dichlorophenyl, 2,4-dimethylphenyl, 2,5-dimethylphenyl, 2,6-dichlorophenyl, 2-bromo-3-methylphenyl, 2-bromophenyl, 2-chloro-3-fluorophenyl, 2-chlorophenyl, 2-cyclopropylphenyl, 2-ethylphenyl, 2-fluoro-3-(trifluoromethyl)phenyl, 2-fluoro-3-methylphenyl, 2-fluorophenyl, 2-isopropylphenyl, 2-methoxyphenyl, 2-nitrophenyl, 3,4-dimethylphenyl, 3,5-dimethylphenyl, 3-bromo-2-(trifluoromethyl)phenyl, 3-chloro-2-fluorophenyl, 3-chloro-2-methylphenyl, 3-chlorophenyl, 3-fluoro-2-(trifluoromethyl)phenyl, 3-fluoro-2-methylphenyl, 4-benzylphenyl, 4-bromo-2-(trifluoromethyl) phenyl, 4-bromo-2-methylphenyl, 4-bromo-5-chloro-2-methylphenyl, 4-bromophenyl, 4-chloro-2-(trifluoromethyl) phenyl, 4-ethylphenyl, 4-fluoro-2-(trifluoromethyl)phenyl, 4-fluoro-2-methylphenyl, 4-fluorophenyl, 4-methoxyphenyl, 5-chloro-2-methylphenyl, benzo[d][1,3]dioxol-5-yl, biphenyl-2-yl, o-tolyl, phenyl, and p-tolyl; and
$R^2$ is H, amino, bromo, chloro, cyclopropyl, methyl, methylthio, phenyl, and n-propyl.

Some embodiments of the present invention pertain to compounds of Formula (Ia) and pharmaceutically acceptable salts, solvates and hydrates thereof:
wherein:
$R^1$ is 2-methylnaphthalen-1-yl, 4-chloronaphthalen-1-yl, and naphthalen-1-yl; and
$R^2$ is H, amino, bromo, chloro, cyclopropyl, methyl, methylthio, phenyl, and n-propyl.

Some embodiments of the present invention pertain to compounds of Formula (Ia) and pharmaceutically acceptable salts, solvates and hydrates thereof:
wherein:
$R^1$ is selected from the group consisting of 1-ethylcyclohexyl, 1-methylcyclohexyl, 2,2-difluorocycloheptyl, 2-hydroxycycloheptyl, 2-methylcyclohexyl, cycloheptanon-2-yl, 2-oxocyclohexyl, 4-hydroxycyclohexyl, adamant-1-yl, bicyclo[2.2.1]heptan-2-yl, cyclobutyl, cycloheptanon-2-yl, cycloheptyl, cyclohexyl, cyclooctyl, and cyclopentyl; and
$R^2$ is H, amino, bromo, chloro, cyclopropyl, methyl, methylthio, phenyl, and n-propyl.

Some embodiments of the present invention pertain to compounds of Formula (Ia) and pharmaceutically acceptable salts, solvates and hydrates thereof:
wherein:
$R^1$ is 3-chloropyridin-4-yl or thiophen-3-yl; and
$R^2$ is H, amino, bromo, chloro, cyclopropyl, methyl, methylthio, phenyl, and n-propyl.

Some embodiments of the present invention pertain to compounds of Formula (Ia) and pharmaceutically acceptable salts, solvates and hydrates thereof:
wherein:
$R^1$ is selected from the group consisting of azepanyl, tetrahydro-2H-pyranyl, and tetrahydro-2H-thiopyranyl; and
$R^2$ is H, amino, bromo, chloro, cyclopropyl, methyl, methylthio, phenyl, and n-propyl.

Some embodiments of the present invention include every combination of one or more compounds selected from the following group shown in TABLE A.

TABLE A

| Cmpd No. | Chemical Structure | Chemical Name |
|---|---|---|
| 1 | 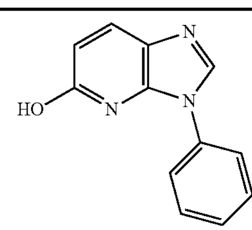 | 3-phenyl-3H-imidazo[4,5-b]pyridin-5-ol |

TABLE A-continued

| Cmpd No. | Chemical Structure | Chemical Name |
|---|---|---|
| 2 | 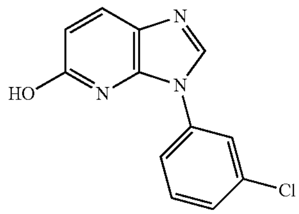 [SMILES: Oc1ccc2ncn(-c3cccc(Cl)c3)c2n1] | 3-(3-chlorophenyl)-3H-imidazo[4,5-b]pyridin-5-ol |
| 3 | 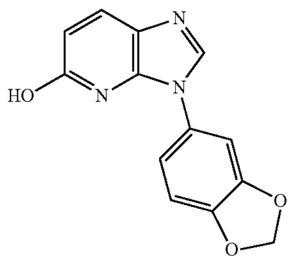 [SMILES: Oc1ccc2ncn(-c3ccc4c(c3)OCO4)c2n1] | 3-(benzo[d][1,3]dioxol-5-yl)-3H-imidazo[4,5-b]pyridin-5-ol |
| 4 | 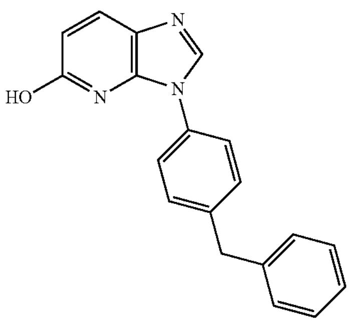 [SMILES: Oc1ccc2ncn(-c3ccc(Cc4ccccc4)cc3)c2n1] | 3-(4-benzylphenyl)-3H-imidazo[4,5-b]pyridin-5-ol |
| 5 | 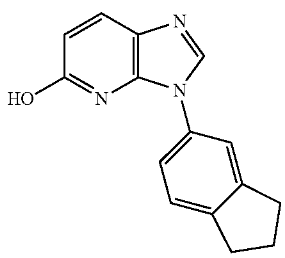 [SMILES: Oc1ccc2ncn(-c3ccc4c(c3)CCC4)c2n1] | 3-(2,3-dihydro-1H-inden-5-yl)-3H-imidazo[4,5-b]pyridin-5-ol |
| 6 | 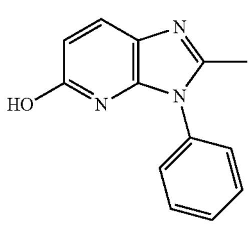 [SMILES: Cc1nc2ccc(O)nc2n1-c1ccccc1] | 2-methyl-3-phenyl-3H-imidazo[4,5-b]pyridin-5-ol |
| 7 | 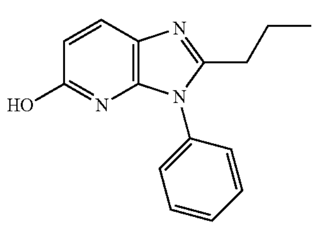 [SMILES: CCCc1nc2ccc(O)nc2n1-c1ccccc1] | 3-phenyl-2-propyl-3H-imidazo[4,5-b]pyridin-5-ol |
| 8 | | 2,3-diphenyl-3H-imidazo[4,5-b]pyridin-5-ol |
| 9 | | 2-amino-3-phenyl-3H-imidazo[4,5-b]pyridin-5-ol |
| 10 | | 3-(4-fluorophenyl)-3H-imidazo[4,5-b]pyridin-5-ol |
| 11 | | 3-(4-methoxyphenyl)-3H-imidazo[4,5-b]pyridin-5-ol |
| 12 | | 3-p-tolyl-3H-imidazo[4,5-b]pyridin-5-ol |
| 13 | | 2-amino-3-(4-ethylphenyl)-3H-imidazo[4,5-b]pyridin-5-ol |

TABLE A-continued

| Cmpd No. | Chemical Structure | Chemical Name |
|---|---|---|
| 14 | 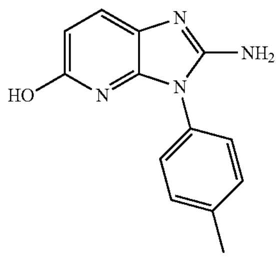 [SMILES: Cc1ccc(-n2c(N)nc3ccc(O)nc32)cc1] | 2-amino-3-p-tolyl-3H-imidazo[4,5-b]pyridin-5-ol |
| 15 | 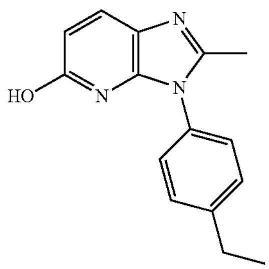 [SMILES: CCc1ccc(-n2c(C)nc3ccc(O)nc32)cc1] | 3-(4-ethylphenyl)-2-methyl-3H-imidazo[4,5-b]pyridin-5-ol |
| 16 | 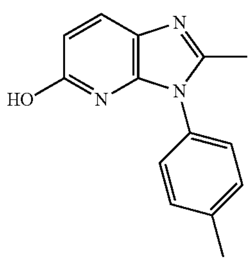 [SMILES: Cc1ccc(-n2c(C)nc3ccc(O)nc32)cc1] | 2-methyl-3-p-tolyl-3H-imidazo[4,5-b]pyridin-5-ol |
| 17 | 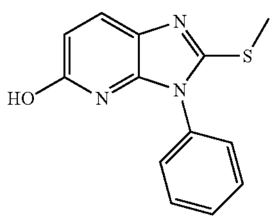 [SMILES: CSc1nc2ccc(O)nc2n1-c1ccccc1] | 2-(methylthio)-3-phenyl-3H-imidazo[4,5-b]pyridin-5-ol |
| 18 | 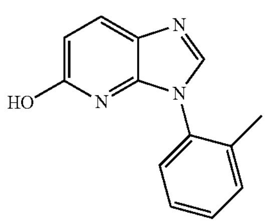 [SMILES: Cc1ccccc1-n1cnc2ccc(O)nc21] | 3-o-tolyl-3H-imidazo[4,5-b]pyridin-5-ol |
| 19 | 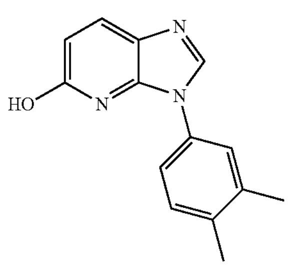 [SMILES: Cc1ccc(-n2cnc3ccc(O)nc32)cc1C] | 3-(3,4-dimethylphenyl)-3H-imidazo[4,5-b]pyridin-5-ol |
| 20 | | 3-(3,5-dimethylphenyl)-3H-imidazo[4,5-b]pyridin-5-ol |
| 21 | | 3-(2,5-dimethylphenyl)-3H-imidazo[4,5-b]pyridin-5-ol |
| 22 | | 3-(4-bromophenyl)-2-methyl-3H-imidazo[4,5-b]pyridin-5-ol |
| 23 | | 2-amino-3-(4-bromophenyl)-3H-imidazo[4,5-b]pyridin-5-ol |
| 24 | | 3-(thiophen-3-yl)-3H-imidazo[4,5-b]pyridin-5-ol |
| 25 | | 3-(2-chlorophenyl)-3H-imidazo[4,5-b]pyridin-5-ol |

TABLE A-continued

| Cmpd No. | Chemical Structure | Chemical Name |
|---|---|---|
| 26 | 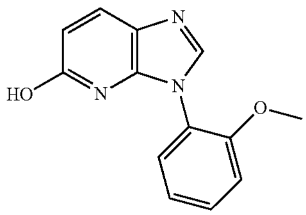 [SMILES: COc1ccccc1-n1cnc2ccc(O)nc21] | 3-(2-methoxyphenyl)-3H-imidazo[4,5-b]pyridin-5-ol |
| 27 | 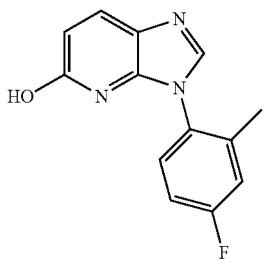 [SMILES: Cc1cc(F)ccc1-n1cnc2ccc(O)nc21] | 3-(4-fluoro-2-methylphenyl)-3H-imidazo[4,5-b]pyridin-5-ol |
| 28 | 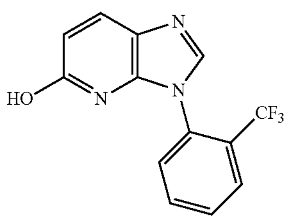 [SMILES: Oc1ccc2ncn(-c3ccccc3C(F)(F)F)c2n1] | 3-(2-(trifluoromethyl)phenyl)-3H-imidazo[4,5-b]pyridin-5-ol |
| 29 | 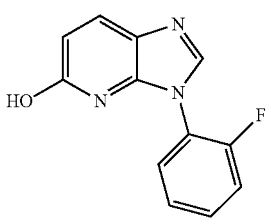 [SMILES: Oc1ccc2ncn(-c3ccccc3F)c2n1] | 3-(2-fluorophenyl)-3H-imidazo[4,5-b]pyridin-5-ol |
| 30 | 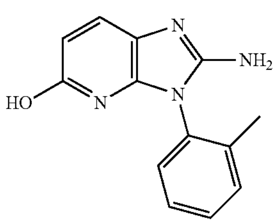 [SMILES: Cc1ccccc1-n1c(N)nc2ccc(O)nc21] | 2-amino-3-o-tolyl-3H-imidazo[4,5-b]pyridin-5-ol |
| 31 | 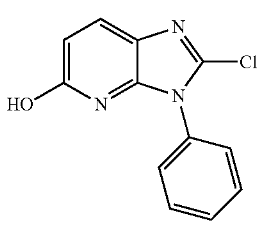 [SMILES: Oc1ccc2nc(Cl)n(-c3ccccc3)c2n1] | 2-chloro-3-phenyl-3H-imidazo[4,5-b]pyridin-5-ol |
| 32 | 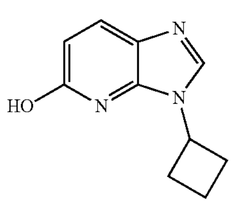 [SMILES: Oc1ccc2ncn(C3CCC3)c2n1] | 3-cyclobutyl-3H-imidazo[4,5-b]pyridin-5-ol |
| 33 | | 3-(2,4-dimethylphenyl)-3H-imidazo[4,5-b]pyridin-5-ol |
| 34 | | 3-(2,6-dimethylphenyl)-3H-imidazo[4,5-b]pyridin-5-ol |
| 35 | | 3-(2-isopropylphenyl)-3H-imidazo[4,5-b]pyridin-5-ol |
| 36 | | 3-(2-ethylphenyl)-3H-imidazo[4,5-b]pyridin-5-ol |
| 37 | | 3-(4-bromo-2-methylphenyl)-3H-imidazo[4,5-b]pyridin-5-ol |
| 38 | | 2-amino-3-(2-(trifluoromethyl)phenyl)-3H-imidazo[4,5-b]pyridin-5-ol |

TABLE A-continued

| Cmpd No. | Chemical Structure | Chemical Name |
|---|---|---|
| 39 | 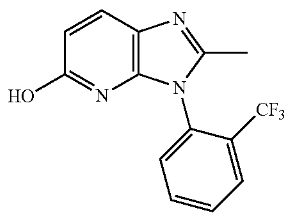 [SMILES: Cc1nc2ccc(O)nc2n1-c1ccccc1C(F)(F)F] | 2-methyl-3-(2-(trifluoromethyl)phenyl)-3H-imidazo[4,5-b]pyridin-5-ol |
| 40 | 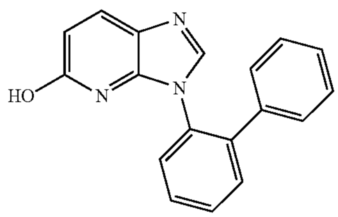 [SMILES: Oc1ccc2ncn(-c3ccccc3-c3ccccc3)c2n1] | 3-(biphenyl-2-yl)-3H-imidazo[4,5-b]pyridin-5-ol |
| 41 | 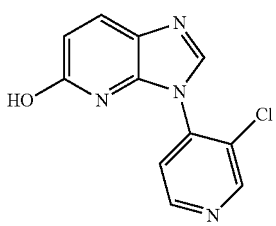 [SMILES: Oc1ccc2ncn(-c3ccncc3Cl)c2n1] | 3-(3-chloropyridin-4-yl)-3H-imidazo[4,5-b]pyridin-5-ol |
| 42 | 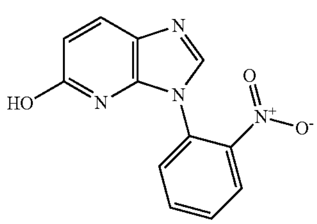 [SMILES: O=[N+]([O-])c1ccccc1-n1cnc2ccc(O)nc21] | 3-(2-nitrophenyl)-3H-imidazo[4,5-b]pyridin-5-ol |
| 43 | 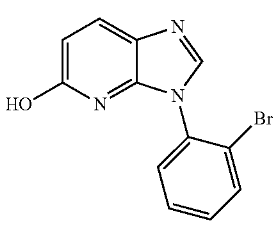 [SMILES: Oc1ccc2ncn(-c3ccccc3Br)c2n1] | 3-(2-bromophenyl)-3H-imidazo[4,5-b]pyridin-5-ol |
| 44 | 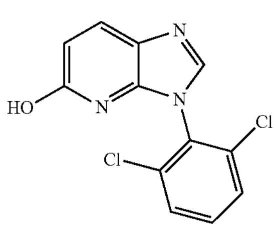 [SMILES: Oc1ccc2ncn(-c3c(Cl)cccc3Cl)c2n1] | 3-(2,6-dichlorophenyl)-3H-imidazo[4,5-b]pyridin-5-ol |
| 45 | | 3-(4-bromo-5-chloro-2-methylphenyl)-3H-imidazo[4,5-b]pyridin-5-ol |
| 46 | | 3-(5-chloro-2-methylphenyl)-3H-imidazo[4,5-b]pyridin-5-ol |
| 47 | | 3-cyclopentyl-3H-imidazo[4,5-b]pyridin-5-ol |
| 48 | | 3-cycloheptyl-3H-imidazo[4,5-b]pyridin-5-ol |
| 49 | | 3-(2,4-dichlorophenyl)-3H-imidazo[4,5-b]pyridin-5-ol |
| 50 | | 3-(3-chloro-2-fluorophenyl)-3H-imidazo[4,5-b]pyridin-5-ol |

TABLE A-continued

| Cmpd No. | Chemical Structure | Chemical Name |
|---|---|---|
| 51 | 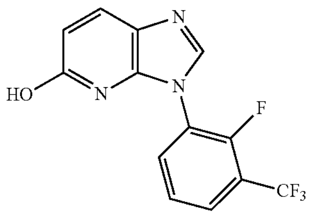 [SMILES: Oc1ccc2ncn(-c3cccc(C(F)(F)F)c3F)c2n1] | 3-(2-fluoro-3-(trifluoromethyl)phenyl)-3H-imidazo[4,5-b]pyridin-5-ol |
| 52 | 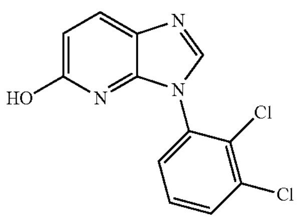 [SMILES: Oc1ccc2ncn(-c3cccc(Cl)c3Cl)c2n1] | 3-(2,3-dichlorophenyl)-3H-imidazo[4,5-b]pyridin-5-ol |
| 53 | 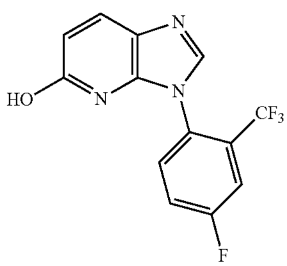 [SMILES: Oc1ccc2ncn(-c3ccc(F)cc3C(F)(F)F)c2n1] | 3-(4-fluoro-2-(trifluoromethyl)phenyl)-3H-imidazo[4,5-b]pyridin-5-ol |
| 54 | 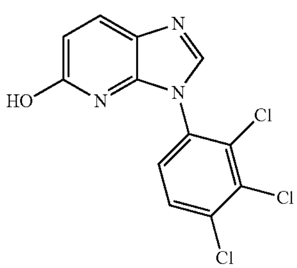 [SMILES: Oc1ccc2ncn(-c3ccc(Cl)c(Cl)c3Cl)c2n1] | 3-(2,3,4-trichlorophenyl)-3H-imidazo[4,5-b]pyridin-5-ol |
| 55 | 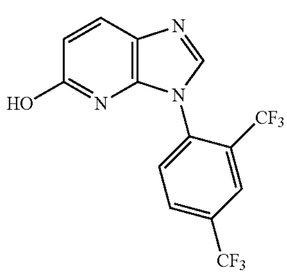 [SMILES: Oc1ccc2ncn(-c3ccc(C(F)(F)F)cc3C(F)(F)F)c2n1] | 3-(2,4-bis(trifluoromethyl)phenyl)-3H-imidazo[4,5-b]pyridin-5-ol |
| 56 | 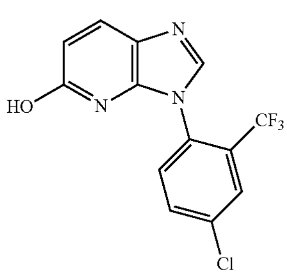 [SMILES: Oc1ccc2ncn(-c3ccc(Cl)cc3C(F)(F)F)c2n1] | 3-(4-chloro-2-(trifluoromethyl)phenyl)-3H-imidazo[4,5-b]pyridin-5-ol |
| 57 | | 3-(4-bromo-2-(trifluoromethyl)phenyl)-3H-imidazo[4,5-b]pyridin-5-ol |
| 58 | | 2-amino-3-(2-fluorophenyl)-3H-imidazo[4,5-b]pyridin-5-ol |
| 59 | | 3-(2,3-difluorophenyl)-3H-imidazo[4,5-b]pyridin-5-ol |
| 60 | | 3-(3-fluoro-2-methylphenyl)-3H-imidazo[4,5-b]pyridin-5-ol |
| 61 | | 3-(3-chloro-2-methylphenyl)-3H-imidazo[4,5-b]pyridin-5-ol |
| 62 | | 3-(2-chloro-3-fluorophenyl)-3H-imidazo[4,5-b]pyridin-5-ol |

TABLE A-continued

| Cmpd No. | Chemical Name |
|---|---|
| 63 | 2-amino-3-(2,3-difluorophenyl)-3H-imidazo[4,5-b]pyridin-5-ol |
| 64 | 2-amino-3-(3-fluoro-2-methylphenyl)-3H-imidazo[4,5-b]pyridin-5-ol |
| 65 | 2-amino-3-(3-chloro-2-methylphenyl)-3H-imidazo[4,5-b]pyridin-5-ol |
| 66 | 2-amino-3-(2-chloro-3-fluorophenyl)-3H-imidazo[4,5-b]pyridin-5-ol |
| 67 | 3-(2-fluoro-3-methylphenyl)-3H-imidazo[4,5-b]pyridin-5-ol |
| 68 | 3-(tetrahydro-2H-pyran-4-yl)-3H-imidazo[4,5-b]pyridin-5-ol |
| 69 | 2-chloro-3-(2-chlorophenyl)-3H-imidazo[4,5-b]pyridin-5-ol |
| 70 | 2-(5-hydroxy-3H-imidazo[4,5-b]pyridin-3-yl)cycloheptanone |
| 71 | 3-(2-hydroxycycloheptyl)-3H-imidazo[4,5-b]pyridin-5-ol |
| 72 | 2-amino-3-(2,4,5-trichlorophenyl)-3H-imidazo[4,5-b]pyridin-5-ol |
| 73 | 2-methyl-3-(2,4,5-trichlorophenyl)-3H-imidazo[4,5-b]pyridin-5-ol |
| 74 | 3-(2,4,5-trichlorophenyl)-3H-imidazo[4,5-b]pyridin-5-ol |
| 75 | 3-(4-chloronaphthalen-1-yl)-2-methyl-3H-imidazo[4,5-b]pyridin-5-ol |

TABLE A-continued

| Cmpd No. | Chemical Structure | Chemical Name |
|---|---|---|
| 76 | 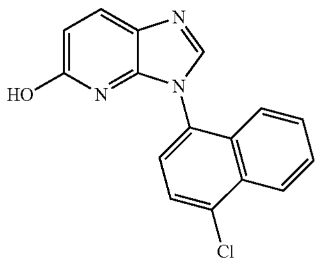 [SMILES: Oc1ccc2ncn(-c3ccc(Cl)c4ccccc34)c2n1] | 3-(4-chloronaphthalen-1-yl)-3H-imidazo[4,5-b]pyridin-5-ol |
| 77 | 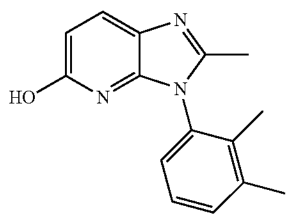 [SMILES: Cc1cccc(-n2c(C)nc3ccc(O)nc32)c1C] | 3-(2,3-dimethylphenyl)-2-methyl-3H-imidazo[4,5-b]pyridin-5-ol |
| 78 | 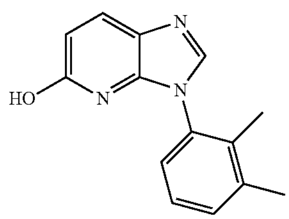 [SMILES: Cc1cccc(-n2cnc3ccc(O)nc32)c1C] | 3-(2,3-dimethylphenyl)-3H-imidazo[4,5-b]pyridin-5-ol |
| 79 | 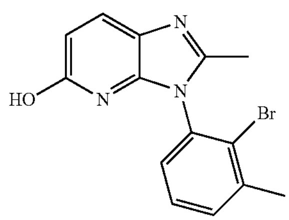 [SMILES: Cc1cccc(-n2c(C)nc3ccc(O)nc32)c1Br] | 3-(2-bromo-3-methylphenyl)-2-methyl-3H-imidazo[4,5-b]pyridin-5-ol |
| 80 | 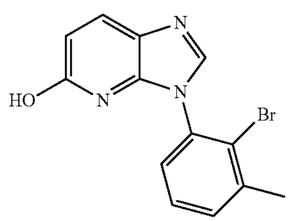 [SMILES: Cc1cccc(-n2cnc3ccc(O)nc32)c1Br] | 3-(2-bromo-3-methylphenyl)-3H-imidazo[4,5-b]pyridin-5-ol |
| 81 | 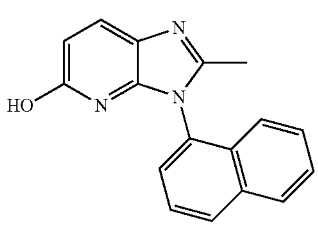 [SMILES: Cc1nc2ccc(O)nc2n1-c1cccc2ccccc12] | 2-methyl-3-(naphthalen-1-yl)-3H-imidazo[4,5-b]pyridin-5-ol |
| 82 | | 2-methyl-3-(2,3,4-trichlorophenyl)-3H-imidazo[4,5-b]pyridin-5-ol |
| 83 | | 2-amino-3-(2,3,4-trichlorophenyl)-3H-imidazo[4,5-b]pyridin-5-ol |
| 84 | | 3-(2-methylnaphthalen-1-yl)-3H-imidazo[4,5-b]pyridin-5-ol |
| 85 | | 3-(naphthalen-1-yl)-3H-imidazo[4,5-b]pyridin-5-ol |
| 86 | | 2-amino-3-(naphthalen-1-yl)-3H-imidazo[4,5-b]pyridin-5-ol |
| 87 | | 2-amino-3-(4-chloronaphthalen-1-yl)-3H-imidazo[4,5-b]pyridin-5-ol |

TABLE A-continued

| Cmpd No. | Chemical Name |
|---|---|
| 88 | 2-amino-3-(2-methylnaphthalen-1-yl)-3H-imidazo[4,5-b]pyridin-5-ol |
| 89 | 2-methyl-3-(2-methylnaphthalen-1-yl)-3H-imidazo[4,5-b]pyridin-5-ol |
| 90 | 3-(4-hydroxycyclohexyl)-3H-imidazo[4,5-b]pyridin-5-ol |
| 91 | 2-(5-hydroxy-3H-imidazo[4,5-b]pyridin-3-yl)cyclohexanone |
| 92 | 3-cyclohexyl-3H-imidazo[4,5-b]pyridin-5-ol |
| 93 | 2-amino-3-cycloheptyl-3H-imidazo[4,5-b]pyridin-5-ol |
| 94 | 3-cyclooctyl-3H-imidazo[4,5-b]pyridin-5-ol |
| 95 | 3-cycloheptyl-2-methyl-3H-imidazo[4,5-b]pyridin-5-ol |
| 96 | 3-(2-hydroxycyclohexyl)-3H-imidazo[4,5-b]pyridin-5-ol |
| 97 | 3-(tetrahydro-2H-thiopyran-4-yl)-3H-imidazo[4,5-b]pyridin-5-ol |
| 98 | 3-(bicyclo[2.2.1]heptan-2-yl)-3H-imidazo[4,5-b]pyridin-5-ol |
| 99 | 3-(2,3-dihydro-1H-inden-4-yl)-3H-imidazo[4,5-b]pyridin-5-ol |
| 100 | 2-amino-3-(2,3-dihydro-1H-inden-4-yl)-3H-imidazo[4,5-b]pyridin-5-ol |
| 101 | 3-(3-bromo-2-(trifluoromethyl)phenyl)-3H-imidazo[4,5-b]pyridin-5-ol |

TABLE A-continued

| Cmpd No. | Chemical Name |
|---|---|
| 102 | 2-chloro-3-(2-fluorophenyl)-3H-imidazo[4,5-b]pyridin-5-ol |
| 103 | 2-bromo-3-(2-fluorophenyl)-3H-imidazo[4,5-b]pyridin-5-ol |
| 104 | tert-butyl 4-(5-hydroxy-3H-imidazo[4,5-b]pyridin-3-yl)azepane-1-carboxylate |
| 105 | 2-bromo-3-(2-chlorophenyl)-3H-imidazo[4,5-b]pyridin-5-ol |
| 106 | 3-(2-cyclopropylphenyl)-3H-imidazo[4,5-b]pyridin-5-ol |
| 107 | 3-(2-(trifluoromethoxy)phenyl)-3H-imidazo[4,5-b]pyridin-5-ol |
| 108 | 2-methyl-3-(2-(trifluoromethoxy)phenyl)-3H-imidazo[4,5-b]pyridin-5-ol |
| 109 | 2-amino-3-(2-(trifluoromethoxy)phenyl)-3H-imidazo[4,5-b]pyridin-5-ol |
| 110 | 2-methyl-3-(2-(methylthio)phenyl)-3H-imidazo[4,5-b]pyridin-5-ol |
| 111 | 3-(3-fluoro-2-(trifluoromethyl)phenyl)-3H-imidazo[4,5-b]pyridin-5-ol |
| 112 | 3-(2-chlorophenyl)-2-methyl-3H-imidazo[4,5-b]pyridin-5-ol |
| 113 | 2-amino-3-(2-chlorophenyl)-3H-imidazo[4,5-b]pyridin-5-ol |
| 114 | 3-(adamant-1-yl)-3H-imidazo[4,5-b]pyridin-5-ol |

TABLE A-continued

| Cmpd No. | Chemical Name |
|---|---|
| 115 | 3-(adamant-1-yl)-2-methyl-3H-imidazo[4,5-b]pyridin-5-ol |
| 116 | 3-(adamant-1-yl)-2-amino-3H-imidazo[4,5-b]pyridin-5-ol |
| 117 | 3-(2-fluorophenyl)-2-methyl-3H-imidazo[4,5-b]pyridin-5-ol |
| 118 | 3-(2,2-difluorocycloheptyl)-3H-imidazo[4,5-b]pyridin-5-ol |
| 119 | 3-(2-methylcyclohexyl)-3H-imidazo[4,5-b]pyridin-5-ol |
| 120 | 3-(2-chlorophenyl)-2-cyclopropyl-3H-imidazo[4,5-b]pyridin-5-ol |
| 121 | 3-(2-(trifluoromethylthio)phenyl)-3H-imidazo[4,5-b]pyridin-5-ol |
| 122 | 2-methyl-3-(2-(trifluoromethylthio)phenyl)-3H-imidazo[4,5-b]pyridin-5-ol |
| 123 | 2-amino-3-(2-(trifluoromethylthio)phenyl)-3H-imidazo[4,5-b]pyridin-5-ol |
| 124 | 2-cyclopropyl-3-(2-(trifluoromethoxy)phenyl)-3H-imidazo[4,5-b]pyridin-5-ol |
| 125 | 2-chloro-3-(2-(trifluoromethoxy)phenyl)-3H-imidazo[4,5-b]pyridin-5-ol |
| 126 | 3-cyclohexyl-2-methyl-3H-imidazo[4,5-b]pyridin-5-ol |
| 127 | 2-chloro-3-cyclohexyl-3H-imidazo[4,5-b]pyridin-5-ol |

TABLE A-continued

| Cmpd No. | Chemical Name |
|---|---|
| 128 | 3-(2-bromophenyl)-2-methyl-3H-imidazo[4,5-b]pyridin-5-ol |
| 129 | 3-(2-bromophenyl)-2-chloro-3H-imidazo[4,5-b]pyridin-5-ol |
| 130 | 2-bromo-3-(2-bromophenyl)-3H-imidazo[4,5-b]pyridin-5-ol |
| 131 | 2-chloro-3-(2-(trifluoromethyl)phenyl)-3H-imidazo[4,5-b]pyridin-5-ol |
| 132 | 2-chloro-3-(2-(trifluoromethylthio)phenyl)-3H-imidazo[4,5-b]pyridin-5-ol |
| 133 | 2-chloro-3-(2-cyclopropylphenyl)-3H-imidazo[4,5-b]pyridin-5-ol |
| 134 | 2-chloro-3-o-tolyl-3H-imidazo[4,5-b]pyridin-5-ol |
| 135 | 2-bromo-3-o-tolyl-3H-imidazo[4,5-b]pyridin-5-ol |
| 136 | 3-(bicyclo[2.2.1]heptan-2-yl)-2-chloro-3H-imidazo[4,5-b]pyridin-5-ol |
| 137 | 3-(1-methylcyclohexyl)-3H-imidazo[4,5-b]pyridin-5-ol |
| 138 | 2-chloro-3-(2-methylcyclohexyl)-3H-imidazo[4,5-b]pyridin-5-ol |
| 139 | 3-(1-ethylcyclohexyl)-2-methyl-3H-imidazo[4,5-b]pyridin-5-ol |
| 140 | 2-methyl-3-(1-ethylcyclohexyl)-3H-imidazo[4,5-b]pyridin-5-ol |

Additionally, individual compounds and chemical genera of the present invention, for example those compounds found in TABLE A including diastereomers and enantiomers thereof, encompass all pharmaceutically acceptable salts, solvates and particularly hydrates, thereof.

It is understood that the present invention embraces each diastereomer, each enantiomer and mixtures thereof of each compound and generic formula disclosed herein just as if they were each individually disclosed with the specific stereochemical designation for each chiral carbon. Separation of the individual isomers (such as, by chiral HPLC, recrystallization of diastereomeric mixtures and the like) or selective synthesis (such as, by enantiomeric selective syntheses and the like) of the individual isomers is accomplished by application of various methods which are well known to practitioners in the art.

The compounds of the Formula (Ia) of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]; incorporated herein by reference in its entirety).

Indications and Methods of Prophylaxis and/or Treatment

The compounds disclosed herein are believed to be useful in the treatment and/or prevention of several diseases and disorders, and in the amelioration of symptoms thereof. These compounds can be used alone or in combination with other compounds for the treatment and/or prevention of diseases and disorders.

As disclosed herein, GPR81 is coupled to Gi, which results in a decrease in the level of intracellular cAMP. Also as disclosed herein, GPR81 is expressed endogenously by adipocytes. In one embodiment, GPR81 inhibits intracellular lipolysis. In another embodiment, agonists of the invention are useful as therapeutic agents for the prevention or treatment of metabolic-related disorders, including, for example, dyslipidemia, atherosclerosis, atheromatous disease, hypertension, coronary heart disease, stroke, insulin resistance, impaired glucose tolerance, type 2 diabetes, syndrome X, and obesity. In one embodiment, the metabolic-related disorder is dyslipidemia. In another embodiment, the metabolic-related disorder is atherosclerosis. In a further embodiment, the metabolic-related disorder is type 2 diabetes.

Dyslipidemia is a general term for abnormal concentrations of blood lipids such as cholesterol, triglycerides and lipoproteins. For example, dyslipidemia includes terms such as hyperlipidemia which is a term for elevated concentrations of any or all of the lipids in the plasma such as cholesterol, triglycerides and lipoproteins. Hyperlipidemia can be acquired or can be congenital. Specific forms of hyperlipidemia can include, for example, hypercholesteremia, familial dysbetalipoproteinemia, diabetic dyslipidemia, nephrotic dyslipidemia and familial combined hyperlipidemia. Hypercholesteremia is characterized by an elevation in serum low density lipoprotein-cholesterol and serum total cholesterol. Familial dysbetalipoproteinemia, also known as type III hyperlipidemia, is characterized by an accumulation of very low density lipoprotein-cholesterol (VLDL-cholesterol) particles called beta-VLDLs in the serum. Also associated with this condition, is a replacement of normal apolipoprotein E3 with abnormal isoform apolipoprotein E2. Diabetic dyslipidemia is characterized by multiple lipoprotein abnormalities, such as an overproduction of VLDL-cholesterol, abnormal VLDL triglyceride lipolysis, reduced LDL-cholesterol receptor activity and, on occasion, Type III hyperlipidemia. Nephrotic dyslipidemia is difficult to treat and frequently includes hypercholesteremia and hypertriglyceridemia. Familial combined hyperlipidemia is characterized by multiple phenotypes of hyperlipidemia, i.e., type IIa, IIb, IV, V or hyperapobetalipoproteinemia.

Atherosclerosis is a process where deposits of fatty substances, cholesterol and other substances build up in the inner lining of an artery. This buildup is called plaque. Plaques that rupture cause blood clots to form that can block blood flow to the heart (heart attack) or the brain (stroke). Heart attack is the number one cause of death for both men and women in the United States and stroke is the number three cause of death [see, for example, Nature Medicine, Special Focus on Atherosclerosis, (2002) 8:1209-1262]. Abnormally high levels of circulating lipids are a major predisposing factor in development of atherosclerosis. Elevated levels of low density lipoprotein (LDL) cholesterol, elevated levels of triglycerides, or low levels of high density lipoprotein (HDL) cholesterol are, independently, risk factors for atherosclerosis and associated pathologies.

In one embodiment, the compound of the invention is used to treat an individual in need of a change in lipid metabolism selected from the group consisting of: a decrease in the level of plasma triglycerides, a decrease in the level of plasma free fatty acids, a decrease in the level of plasma cholesterol, a decrease in the level of LDL-cholesterol, an increase in the level of HDL-cholesterol, a decrease in the total cholesterol/HDL-cholesterol ratio and an increase in the level of plasma adiponectin.

Atheromatous disease is the accumulation of atheroma which is a deposition or swelling in artery walls that is made up of cells, or cell debris, that contain lipids (cholesterol and fatty acids), calcium and a variable amount of fibrous connective tissue. In the context of heart or artery matters, atheromata are commonly referred to as atheromatous plaques. The deposition (swelling) is between the endothelium lining and the smooth muscle wall central region (media) of the arterial tube. While the early stages, based on gross appearance, have traditionally been termed fatty streaks by pathologists, they are not composed of fat cells, i.e. adipose cells, but of accumulations of white blood cells, especially macrophages that have taken up oxidized low-density lipoprotein (LDL). After they accumulate large amounts of cytoplasmic membranes (with associated high cholesterol content) they are called foam cells. When foam cells die, their contents are released, which attracts more macrophages and creates an extracellular lipid core near the center to inner surface of each atherosclerotic plaque. Conversely, the outer, older portions of the plaque become more calcific, less metabolically active and more physically stiff over time. Collectively, the process of atheroma development within an individual is called atherogenesis and the overall result of the disease process is termed atherosclerosis.

Metabolic-related disorders generally include any disorder related to a non-optimal level of an atherosclerosis-associated serum lipid, for example, LDL-cholesterol, VLDL-cholesterol, HDL-cholesterol or triglycerides in a subject. Therefore, a metabolic-related disorder can be, for example, an elevated level of LDL-cholesterol, a reduced level of HDL-cholesterol, or a disorder caused, at least in part, by a non-optimal level of an atherosclerosis associated serum lipid such as atherosclerosis, heart attack (myocardial infarction), or stroke. Regarding LDL-cholesterol levels, the American Heart Association currently considers an LDL-cholesterol level of less than 100 mg/dL as optimal. 100-129 mg/dL is near optimal, 130-159 mg/dL is borderline-high, 160-189 mg/dL is high and 190 mg/dL is considered a very high level of LDL-cholesterol. Regarding triglyceride levels, the American Heart Association currently considers less than 150 mg/L as normal. 150-199 mg/dL is borderline-high, 200-499 mg/dL is high and 500 mg/dL is considered a very high level of triglycerides.

Disorders that are caused, at least in part, by a non-optimal level of an atherosclerosis-associated serum lipid are included in the definition of a metabolic-related disorder. Such disorders include, for example, coronary artery disease (CAD) or coronary heart disease, congestive heart failure, angina, aneurysm, ischemic heart disease, myocardial infarction and stroke. A metabolic-related disorder can include heart disease such as coronary heart disease, which is a disorder comprising a narrowing of the small blood vessels that supply blood to the heart, and congestive heart failure where the heart loses its ability to pump blood efficiently. A metabolic-related disorder can include a disorder caused by reduced blood flow to a tissue or organ due to partial or complete blockage of a blood vessel. Such disorders include, for example, angina, ischemic heart disease, myocardial infarction and stroke. A metabolic-related disorder can include a disorder caused by weakened blood vessels such as, for example, an aneurysm, which is a weakened area in a blood vessel often caused by atherosclerosis.

The methods, compositions and kits of the invention can be used to prevent or treat a metabolic-related disorder in a subject. When used to prevent a metabolic-related disorder, the subject can have optimal levels of lipids but may be at risk for a metabolic-related disorder for other reasons, for example, a family history of a metabolic-related disorder. The methods, composition and kits of the invention can be used prophylactically to prevent a metabolic-related disorder in a subject of any age, for example, in a child or adult with risk factors for developing a metabolic-related disorder.

Heart disease includes, but is not limited to, cardiac insufficiency, coronary insufficiency, coronary artery disease, and high blood pressure (hypertension). Peripheral vascular disease refers to diseases of blood vessels outside the heart and brain. Organic peripheral vascular diseases are caused by structural changes in the blood vessels, such as inflammation and tissue damage. Peripheral artery disease is an example. Peripheral artery disease (PAD) is a condition similar to coronary artery disease and carotid artery disease. In PAD, fatty deposits build up along artery walls and affect blood circulation, mainly in arteries leading to the legs and feet. In its early stages a common symptom is cramping or fatigue in the legs and buttocks during activity. Such cramping subsides when the person stands still. This is called "intermittent claudication." People with PAD have a higher risk of death from stroke and heart attack, due to the risk of blood clots.

Stroke or cerebrovascular accident is the rapidly developing loss of brain functions due to a disturbance in the blood vessels supplying blood to the brain. This can be due to ischemia (lack of blood supply) caused by thrombosis or embolism, or due to a hemorrhage. Risk factors for stroke include advanced age, hypertension, previous stroke or transient ischaemic attack (TIA), diabetes, high cholesterol, cigarette smoking, atrial fibrillation, migraine with aura, and thrombophilia (a tendency to thrombosis).

Insulin resistance encompasses the usual diagnosis of insulin resistance made by any of a number of methods, including, for example, the intravenous glucose tolerance test or measurement of the fasting insulin level. It is well known that there is a good correlation between the height of the fasting insulin level and the degree of insulin resistance. Therefore, one could use elevated fasting insulin levels as a surrogate marker for insulin resistance for the purpose of identifying which normal glucose tolerance (NGT) individuals have insulin resistance. A diagnosis of insulin resistance can also be made using the euglycemic glucose clamp test.

Impaired glucose tolerance indicates a condition associated with insulin-resistance that is intermediate between frank, type 2 diabetes and normal glucose tolerance. Impaired glucose tolerance is diagnosed by a procedure wherein an affected person's postprandial glucose response is determined to be abnormal as assessed by two-hour postprandial plasma glucose levels. In this test, a measured amount of glucose is given to the patient and blood glucose levels are measured at regular intervals, usually every half hour for the first two hours and every hour thereafter. In a "normal" or non-impaired glucose tolerant individual, glucose levels rise during the first two hours to a level less than 140 mg/dL and then drop rapidly. In an impaired glucose tolerant individual, the blood glucose levels rise higher and drop-off level at a slower rate.

Diabetes encompasses the usual diagnosis of diabetes made from any method including, for example, symptoms of diabetes (e.g., polyuria, polydipsia, polyphagia) plus casual blood glucose levels greater than or equal to 200 mg/dL, wherein casual blood glucose is defined any time of the day regardless of the timing of meal or drink consumption; or eight-hour fasting blood glucose levels greater than or equal to 126 mg/dL; or blood glucose levels greater than or equal to 200 mg/dL two hours following oral administration of 75 g anhydrous glucose dissolved in water. In addition, the term diabetes also includes the "pre-diabetic" state, defined by the American Diabetes Association to be a fasting blood glucose level of 100-125 mg/dL or blood glucose levels of 140-199 mg/dL two hours following oral administration of glucose.

Syndrome X, also called metabolic syndrome, is characterized by a group of metabolic risk factors in one person. They include: central obesity (excessive fat tissue in and around the abdomen), atherogenic dyslipidemia (blood fat disorders—mainly high triglycerides and low HDL cholesterol), raised blood pressure (130/85 mm Hg or higher), insulin resistance or glucose intolerance, a prothrombotic state (e.g., high fibrinogen or plasminogen activator inhibitor in the blood), and a pro-inflammatory state (e.g., elevated high-sensitivity C-reactive protein in the blood).

As disclosed above, GPR81 is coupled to Gi and is expressed endogenously by adipocytes. It is known that an increase in cellular levels of cAMP down-regulates the secretion of adiponectin from adipocytes [Delporte, M L et al. *Biochem J* (2002) 367:677-85]. Reduced levels of plasma adiponectin have been associated with metabolic-related disorders, including atherosclerosis, coronary heart disease, stroke, insulin resistance and type 2 diabetes [Matsuda, M. et al. *J. Biol. Chem.* (2002) 277:37487-91; also see: Yamauchi T et al., *Nat Med* (2002) 8:1288-95; and Tomas E et al., *Proc Natl Acad Sci USA* (2002) November 27]. Globular adiponectin protected ob/ob mice from diabetes and apoE deficient mice from atherosclerosis [Yamauchi, T. et al. *J. Biol. Chem.* (2002), also see Okamoto, Y. et al. *Circulation* (2002) 26:2767-70]. There is evidence that the regulation of human serum adiponectin levels through modulation of adipocyte intracellular cAMP level is independent of adipocyte lipolysis [Staiger H et al., Horm Metab Res (2002) 34:601-3].

In some embodiments, the present invention is directed to methods of modulating the activity of a GPR81 receptor by contacting the receptor with a compound or a pharmaceutical composition as described herein.

In some embodiments, the present invention is directed to methods of agonizing a GPR81 receptor by contacting the receptor with a compound or a pharmaceutical composition as described herein.

In some embodiments, the present invention is directed to methods for the treatment of a GPR81 receptor related disorder in an individual, comprising administering to the individual in need thereof, a therapeutically effective amount of a compound or a pharmaceutical composition as described herein.

In some embodiments, the present invention is directed to methods for the treatment of a metabolic-related disorder in an individual, comprising administering to the individual in need thereof, a therapeutically effective amount of a compound or a pharmaceutical composition as described herein.

In some embodiments, the present invention is directed to methods for the treatment of a metabolic-related disorder in an individual, wherein metabolic-related disorder is selected from the group consisting of dyslipidemia, atherosclerosis, atheromatous disease, hypertension, coronary heart disease, stroke, insulin resistance, impaired glucose tolerance, type 2 diabetes, syndrome X, and obesity, comprising administering to the individual in need thereof, a therapeutically effective amount of a compound or a pharmaceutical composition as described herein.

In some embodiments, the present invention is directed to methods for the treatment of dyslipidemia, comprising administering to the individual in need thereof, a therapeutically effective amount of a compound or a pharmaceutical composition as described herein.

In some embodiments, the present invention is directed to methods for the treatment of atherosclerosis, comprising administering to the individual in need thereof, a therapeutically effective amount of a compound or a pharmaceutical composition as described herein.

In some embodiments, the present invention is directed to methods for the treatment of atheromatous disease, comprising administering to the individual in need thereof, a therapeutically effective amount of a compound or a pharmaceutical composition as described herein.

In some embodiments, the present invention is directed to methods for the treatment of hypertension, comprising administering to the individual in need thereof, a therapeutically effective amount of a compound or a pharmaceutical composition as described herein.

In some embodiments, the present invention is directed to methods for the treatment of coronary heart disease, comprising administering to the individual in need thereof, a therapeutically effective amount of a compound or a pharmaceutical composition as described herein.

In some embodiments, the present invention is directed to methods for the treatment of stroke, comprising administering to the individual in need thereof, a therapeutically effective amount of a compound or a pharmaceutical composition as described herein.

In some embodiments, the present invention is directed to methods for the treatment of insulin resistance, comprising administering to the individual in need thereof, a therapeutically effective amount of a compound or a pharmaceutical composition as described herein.

In some embodiments, the present invention is directed to methods for the treatment of impaired glucose tolerance, comprising administering to the individual in need thereof, a therapeutically effective amount of a compound or a pharmaceutical composition as described herein.

In some embodiments, the present invention is directed to methods for the treatment of type 2 diabetes, comprising administering to the individual in need thereof, a therapeutically effective amount of a compound or a pharmaceutical composition as described herein.

In some embodiments, the present invention is directed to methods for the treatment of syndrome X, comprising administering to the individual in need thereof, a therapeutically effective amount of a compound or a pharmaceutical composition as described herein.

In some embodiments, the present invention is directed to methods for the treatment of obesity, comprising administering to the individual in need thereof, a therapeutically effective amount of a compound or a pharmaceutical composition as described herein.

In some embodiments, the present invention is directed to the use of a compound, as described herein, in the manufacture of a medicament for the treatment of a GPR81 receptor related disorder.

In some embodiments, the present invention is directed to the use of a compound, as described herein, in the manufacture of a medicament for the treatment of a metabolic-related disorder.

In some embodiments, the present invention is directed to the use of a compound, as described herein, in the manufacture of a medicament for the treatment of dyslipidemia, atherosclerosis, atheromatous disease, hypertension, coronary heart disease, stroke, insulin resistance, impaired glucose tolerance, type 2 diabetes, syndrome X, or obesity.

In some embodiments, the present invention is directed to the use of a compound, as described herein, in the manufacture of a medicament for the treatment of dyslipidemia.

In some embodiments, the present invention is directed to the use of a compound, as described herein, in the manufacture of a medicament for the treatment of atherosclerosis.

In some embodiments, the present invention is directed to the use of a compound, as described herein, in the manufacture of a medicament for the treatment of atheromatous disease.

In some embodiments, the present invention is directed to the use of a compound, as described herein, in the manufacture of a medicament for the treatment of hypertension.

In some embodiments, the present invention is directed to the use of a compound, as described herein, in the manufacture of a medicament for the treatment of coronary heart disease.

In some embodiments, the present invention is directed to the use of a compound, as described herein, in the manufacture of a medicament for the treatment of stroke.

In some embodiments, the present invention is directed to the use of a compound, as described herein, in the manufacture of a medicament for the treatment of insulin resistance.

In some embodiments, the present invention is directed to the use of a compound, as described herein, in the manufacture of a medicament for the treatment of impaired glucose tolerance.

In some embodiments, the present invention is directed to the use of a compound, as described herein, in the manufacture of a medicament for the treatment of type 2 diabetes.

In some embodiments, the present invention is directed to the use of a compound, as described herein, in the manufacture of a medicament for the treatment of syndrome X.

In some embodiments, the present invention is directed to the use of a compound, as described herein, in the manufacture of a medicament for the treatment of obesity.

In some embodiments, the present invention is directed compounds, as described herein, for use in a method of treatment of the human or animal body by therapy.

In some embodiments, the present invention is directed compounds, as described herein, for use in a method of treatment of a GPR81 receptor related disorder.

In some embodiments, the present invention is directed compounds, as described herein, for use in a method of treatment of a metabolic-related disorder.

In some embodiments, the present invention is directed compounds, as described herein, for use in a method of treatment of dyslipidemia, atherosclerosis, atheromatous disease, hypertension, coronary heart disease, stroke, insulin resistance, impaired glucose tolerance, type 2 diabetes, syndrome X, or obesity.

In some embodiments, the present invention is directed compounds, as described herein, for use in a method of treatment of dyslipidemia.

In some embodiments, the present invention is directed compounds, as described herein, for use in a method of treatment of atherosclerosis.

In some embodiments, the present invention is directed compounds, as described herein, for use in a method of treatment of atheromatous disease.

In some embodiments, the present invention is directed compounds, as described herein, for use in a method of treatment of hypertension.

In some embodiments, the present invention is directed compounds, as described herein, for use in a method of treatment of coronary heart disease.

In some embodiments, the present invention is directed compounds, as described herein, for use in a method of treatment of stroke.

In some embodiments, the present invention is directed compounds, as described herein, for use in a method of treatment of insulin resistance.

In some embodiments, the present invention is directed compounds, as described herein, for use in a method of treatment of impaired glucose tolerance.

In some embodiments, the present invention is directed compounds, as described herein, for use in a method of treatment of type 2 diabetes.

In some embodiments, the present invention is directed compounds, as described herein, for use in a method of treatment of syndrome X.

In some embodiments, the present invention is directed compounds, as described herein, for use in a method of treatment of obesity.

Adiponectin is also known to inhibit inflammation [see, for example, Takemura et al. *Curr. Atheroscler. Rep.* 2007 September; 9(3):238-43 and Lago et al., *Cytokine Growth Factor Rev* 2007 June-August; 18(3-4):313-35]. In one embodiment, agonists of the invention are useful as therapeutic agents for the prevention or treatment of inflammation and autoimmunity. The present invention relates to compounds that are GPR81 receptor agonists having at least immunosuppressive, anti-inflammatory and/or hemostatic activities.

GPR81 receptor agonists are useful to treat or prevent conditions where suppression of the immune system or agonism of the GPR81 receptor is in order, such as diseases and disorders mediated by lymphocytes, transplant rejection, autoimmune diseases and disorders, inflammatory diseases and disorders (e.g., acute and chronic inflammatory conditions), cancer, and conditions that have an underlying defect in vascular integrity or that are associated with angiogenesis such as may be pathologic (e.g., as may occur in inflammation, tumor development and atherosclerosis). Such conditions where suppression of the immune system or agonism of the GPR81 receptor is in order include diseases and disorders mediated by lymphocytes, conditions that have an underlying defect in vascular integrity, autoimmune diseases and disorders, inflammatory diseases and disorders (e.g., acute and chronic inflammatory conditions), (acute or chronic) rejection of cells, tissue or solid organ grafts, arthritis including psoriatic arthritis and rheumatoid arthritis, diabetes including type 1 diabetes, demyelinating disease including multiple sclerosis, ischemia-reperfusion injury including renal and cardiac ischemia-reperfusion injury, inflammatory skin disease including psoriasis, atopic dermatitis and acne, hyperproliferative skin disease including acne, inflammatory bowel disease including Crohn's disease and ulcerative colitis, systemic lupus erythematosis, asthma, uveitis, myocarditis, allergy, atherosclerosis, brain inflammation including Alzheimer's disease and brain inflammatory reaction following traumatic brain injury, central nervous system disease including spinal cord injury or cerebral infarction, pathologic angiogenesis including as may occur in primary and metastatic tumor growth, rheumatoid arthritis, diabetic retinopathy and atherosclerosis, cancer, chronic pulmonary disease, acute lung injury, acute respiratory disease syndrome, sepsis and the like.

In one embodiment, inflammatory and autoimmune disorders include psoriasis, rheumatoid arthritis, Crohn's disease, transplant rejection, multiple sclerosis, systemic lupus erythematosus, ulcerative colitis, type 1 diabetes, and acne.

In some embodiments, the present invention is directed to methods for the treatment of an inflammatory disorder in an individual, comprising administering to the individual in need thereof; a therapeutically effective amount of a compound or a pharmaceutical composition as described herein.

In some embodiments, the present invention is directed to methods for the treatment of an autoimmune disorder in an individual, comprising administering to the individual in need thereof, a therapeutically effective amount of a compound or a pharmaceutical composition as described herein.

In some embodiments, the present invention is directed to methods for the treatment of psoriasis, rheumatoid arthritis, Crohn's disease, transplant rejection, multiple sclerosis, systemic lupus erythematosus, ulcerative colitis, type 1 diabetes, or acne in an individual, comprising administering to the individual in need thereof, a therapeutically effective amount of a compound or a pharmaceutical composition as described herein.

In some embodiments, the present invention is directed to the use of a compound described herein, in the manufacture of a medicament for the treatment of an inflammatory disorder.

In some embodiments, the present invention is directed to the use of a compound described herein, in the manufacture of a medicament for the treatment of an autoimmune disorder.

In some embodiments, the present invention is directed to the use of a compound described herein, in the manufacture of a medicament for the treatment of psoriasis, rheumatoid arthritis, Crohn's disease, transplant rejection, multiple sclerosis, systemic lupus erythematosus, ulcerative colitis, type 1 diabetes, or acne.

In some embodiments, the present invention is directed to the use of a compound described herein, in a method of treatment of an inflammatory disorder.

In some embodiments, the present invention is directed to the use of a compound described herein, in a method of treatment of an autoimmune disorder.

In some embodiments, the present invention is directed to the use of a compound described herein, in a method of treatment of psoriasis, rheumatoid arthritis, Crohn's disease, transplant rejection, multiple sclerosis, systemic lupus erythematosus, ulcerative colitis, type 1 diabetes, or acne.

Combination Therapy:

While the compounds of the present invention and described herein, can be administered as the sole active pharmaceutical agent (i.e., mono-therapy), they can also be used in combination with one or more pharmaceutical agents (i.e., combination-therapy), including for example, agents used in the treatment of diabetes, blood lipid disorders or obesity. Therefore, another aspect of the present invention includes methods of treatment of metabolic related diseases comprising administering to an individual in need of such treatment a therapeutically-effective amount of a compound of the present invention in combination with one or more additional pharmaceutical agent as described herein. For example, they can be used in combination with one or more agents belonging to the class of drugs known as α-glucosidase inhibitors, aldose reductase inhibitors, biguanides, thiazolidinediones, meglitinides, sulfonylureas, insulin, HMG-CoA reductase inhibitors, squalene synthesis inhibitors, fibrate compounds, LDL catabolism enhancers, angiotensin converting enzyme (ACE) inhibitors, lipase inhibitors, serotonin and/or noradrenaline releasers or reuptake inhibitors.

α-Glucosidase inhibitors belong to the class of drugs which competitively inhibit digestive enzymes such as α-amylase, maltase, α-dextrinase, sucrase, etc. in the pancreas and or small intestine. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3-dihydroxy-2-propyl)valiolamine (generic name: voglibose), miglitol, and α-glucosidase inhibitors known in the art.

The class of aldose reductase inhibitors is drugs which inhibit the first-stage, rate-limiting enzyme in the polyol pathway and thereby prevent or arrest diabetic complications. In the hyperglycemic state of diabetes, the utilization of glucose in the polyol pathway is increased and the excess sorbitol accumulated intracellularly as a consequence acts as a tissue toxin and hence evokes the onset of complications such as diabetic neuropathy, retinopathy, and nephropathy. Examples of the aldose reductase inhibitors include tolurestat; epalrestat; 3,4-dihydro-2,8-diisopropyl-3-thioxo-2H-1,4-benzoxazine-4-acetic acid; 2,7-difluorospiro(9H-fluorene-9,4'-imidazolidine)-2',5'-dione (generic name: imirestat); 3-[(4-bromo-2-fluorophenyl)methy]-7-chloro-3,4-dihydro-2,4-dioxo-1-(2H)-quinazoline acetic acid (generic name: zenarestat); 6-fluoro-2,3-dihydro-2',5'-dioxo-spiro[4H-1-benzopyran-4,4'-imidazolidine]-2-carboxamide (SNK-860); zopolrestat; sorbinil; and 1-[(3-bromo-2-benzofuranyl)sulfonyl]-2,4-imidazolidinedione (M-16209), and aldose reductase inhibitors known in the art.

The biguanides are a class of drugs that stimulate anaerobic glycolysis, increase the sensitivity to insulin in the peripheral tissues, inhibit glucose abroad sorption from the intestine, suppress hepatic gluconeogenesis, and inhibit fatty acid oxidation. Examples of biguanides include phenformin, metformin, buformin, and biguanides known in the art.

Insulin secretion enhancers belong to the class of drugs having the property to promote secretion of insulin from pancreatic O-cells. Examples of the insulin secretion enhancers include sulfonylureas (SU), which are drugs which promote secretion of insulin from pancreatic β-cells by transmitting signals of insulin secretion via SU receptors in the cell membranes. Examples of the sulfonylureas include tolbutamide, chlorpropamide, tolazamide, acetohexamide, 4-chloro-N-[(1-pyrrolidinylamino)carbonyl]-benzene-sulfonamide (generic name: glycopyramide) or its ammonium salt, glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, tolcyclamide, glimepiride and other insulin secretion enhancers known in the art. Other insulin secretion enhancers include N-[[4-(1-methylethyl)cyclohexyl)carbonyl]-D-phenylalanine (Nateglinide), calcium (2S)-2-benzyl-3-(cis-hexahydro-2-isoindolinylcarbonyl)propionate dihydrate (Mitiglinide, KAD-1229), and other insulin secretion enhancers known in the art.

Thiazolidinediones belong to the class of drugs more commonly known as TZDs. Thiazolidinediones are a class of drugs for type 2 diabetes that lower the blood sugar by increasing the sensitivity of cells to insulin. Insulin can then move glucose from the blood into cells for energy. These drugs can also increase HDL. Examples of thiazolidinediones include rosiglitazone, pioglitazone, and thiazolidinediones known in the art. Rezulin (troglitazone) was the first drug in this class in the U.S., but was taken off the market because of liver toxicity. Related compounds are now available with improved safety profiles and include, for example, Actos (pioglitazone) and Avandia (rosiglitazone). The main contraindications to the use of these medications include liver disease and heart failure. These drugs can also cause a significant increase in fluid retention and thereby increase the risk of heart failure.

Meglitinides are used to stop the rapid rise in blood sugar that can occur immediately after a person with type 2 diabetes eats a meal. These compounds, which include, for example, repaglinide (Prandin) and nateglinide (Starlix), work by increasing the amount of insulin produced by the pancreas similar to the way sulfonyurea medications work. Meglitinides are taken before eating a meal. Side effects associated with this class of drugs include low blood sugar, upper respiratory infections including sinus conditions, headache, joint and back pain, nausea, diarrhea and constipation.

The different types of insulin are categorized according to how fast they start to work (onset) and how long they continue to work (duration). The types now available include rapid-, short-, intermediate-, and long-acting insulin. There are premixed rapid- and intermediate-acting insulins available, including: 70% intermediate-acting (NPH) and 30% short-acting regular insulin, called 70/30 insulin; 50% intermediate-acting (NPH) and 50% short-acting regular insulin, called 50/50 insulin; 75% intermediate-acting (NPH) and 25% rapid-acting Humalog (lispro), called 75/25 insulin; 70% intermediate-acting (NPH); and 30% rapid-acting NovoLog (insulin aspart), called NovoLog Mix 70/30. Insulin usually is given as an injection into the tissues under the skin (subcutaneous). It can also be given through an insulin pump or jet injector, a device that sprays the medication into the skin.

Insulin lets glucose enter cells, where it is used for energy. Without insulin, the blood sugar level rises above what is safe for the body. Usually, a rapid- or short-acting and an intermediate- or long-acting insulin is taken to provide the constant and variable levels of insulin that the body needs. The short-acting insulin reduces blood sugar levels quickly and then wears off. Some long-acting insulins start taking effect when rapid- or short-acting insulins begin to wear off. The new long-acting insulin, Lantus, starts to work within a few minutes after it is given and continues to work at the same rate for about 24 hours.

The combination of a rapid- or short-acting and intermediate- or long-acting insulin helps keep blood sugar levels within a range that is safe for the body throughout the day. Thus insulin can be used to treat people with type 1 diabetes, people with type 2 diabetes whose pancreas produces little or no insulin or whose oral medications do not control their blood sugar. These people may take insulin either alone or along with oral medication, people with type 2 diabetes whose blood sugar levels are high because of a severe illness or major surgery, women with type 2 diabetes who are pregnant or breast-feeding who cannot keep their blood sugar levels within a safe range with diet and exercise. Only one oral diabetes medication (glyburide) has been studied for use during pregnancy.

The major side effect of insulin can be a dangerously low blood sugar level (severe hypoglycemia). A very low blood sugar level can develop within 10 to 15 minutes. Insulin can contribute to weight gain, especially in people with type 2 who already are overweight. Other possible side effects of long-term insulin use include the loss of fatty tissue (lipodystrophy) where the insulin is injected and, rarely, allergic reactions that include swelling (edema).

Statin compounds belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. A statin that inhibits this reductase lowers serum LDL concentrations by upregulating the activity of LDL receptors and responsible for clearing LDL from the blood. Examples of the statin compounds include rosuvastatin, pravastatin and its sodium salt, simvastatin, lovastatin, atorvastatin, fluvastatin, cerivastatin, and HMG-CoA reductase inhibitors known in the art.

Squalene synthesis inhibitors belong to a class of drugs that lower blood cholesterol levels by inhibiting synthesis of squalene. Examples of the squalene synthesis inhibitors include (S)-α-[bis[2,2-dimethyl-1-oxopropoxy)methoxy]phosphinyl]-3-phenoxybenzenebutanesulfonic acid, mono potassium salt (BMS-188494) and squalene synthesis inhibitors known in the art.

Fibrate compounds belong to a class of drugs that lower blood cholesterol levels by inhibiting synthesis and secretion of triglycerides in the liver and activating a lipoprotein lipase. Fibrates have been known to activate peroxisome proliferator-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

LDL (low-density lipoprotein) catabolism enhancers belong to a class of drugs that lower blood cholesterol levels by increasing the number of LDL receptors, examples include LDL catabolism enhancers known in the art.

Angiotensin converting enzyme (ACE) inhibitors belong to the class of drugs that partially lower blood glucose levels as well as lowering blood pressure by inhibiting angiotensin converting enzymes. Examples of angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Lipase inhibitors include, for example, anti-obesity compounds such as orlistat (Xenical™). Orlistat inhibits fat abroad sorption directly but also tends to produce a high incidence of unpleasant gastric side-effects such as diarrhea and flatulence.

Another class of anti-obesity drugs includes serotonin and/or noradrenaline releasers or reuptake inhibitors. For example, sibutramine (Meridia™) is a mixed 5-HT/noradrenaline reuptake inhibitor. The main side effect of sibutramine can be an increase in blood pressure and heart rate in some patients. The serotonin releaser/reuptake inhibitors fenfluramine (Pondimin™) and dexfenfluramine (Redux™) have been reported to decrease food intake and body weight over a prolonged period (greater than 6 months). However, both products were withdrawn from use after reports of preliminary evidence of heart valve abnormalities associated with their use.

Some embodiments of the invention include, a pharmaceutical composition comprising a compound of Formula (Ia) or a pharmaceutically acceptable salt thereof in combination with at least one pharmaceutical agent selected from the group consisting of α-glucosidase inhibitors, aldose reductase inhibitors, biguanides, HMG-CoA reductase inhibitors, squalene synthesis inhibitors, fibrate compounds, LDL catabolism enhancers and angiotensin converting enzyme inhibitors. In another embodiment, the pharmaceutical composition is a compound of Formula (Ia) or a pharmaceutically acceptable salt thereof in combination with a HMG-CoA reductase inhibitor. In still another embodiment, the HMG-CoA reductase inhibitor is selected from the group consisting of prevastatin, simvastatin, lovastatin, atorvastatin, fluvastatin and lipitor.

Other suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, $β_3$ adrenergic receptor agonists, dopamine agonists (for example, bromocriptine), melanocyte-stimulating hormone receptor analogs, cannabinoid 1 receptor antagonists [for example, SR141716: N-(piperidin-1-yl)-5-(4-chlorophenyl)-1-(2,4-dichlorophenyl)-4-methyl-1H-pyrazole-3-carboxamide], melanin concentrating hormone antagonists, leptin (the OB protein), leptin analogues, leptin receptor agonists, galanin antagonists, lipase inhibitors (such as tetrahydrolipstatin, i.e., orlistat), anorectic agents, such as a bombesin agonists, neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter and Gamble Company, Cincinnati, Ohio), human agouti-related proteins (AGRP), ghrelin receptor antagonists, histamine 3 (H3) receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

In some embodiments, the anti-obesity agents are selected from the group consisting of orlistat, sibutramine, bromocriptine, ephedrine, leptin, and pseudoephedrine. In a further embodiment, compounds of the present invention and combination therapies are administered in conjunction with exercise and/or a sensible diet.

It is understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

Other suitable pharmaceutical agents, in addition to anti-obesity agents, that can be used in combination with the compounds of the present invention include agents useful in the treatment of concomitant disorders. Treatment of such disorders include the use of one or more pharmaceutical agents known in the art that belong to the classes of drugs referred to, but not limited to, the following: sulfonylureas, meglitinides, biguanides, α-glucosidase inhibitors, peroxisome proliferators-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In accordance to one aspect of the present invention, a compound of the present can be used in combination with a pharmaceutical agent or agents belonging to one or more of the classes of drugs cited herein.

It is understood that the scope of combination-therapy of the compounds of the present invention with other pharmaceutical agents is not limited to those listed herein, supra or infra, but includes in principle any combination with any pharmaceutical agent or pharmaceutical composition useful for the treatment of diseases, conditions or disorders that are linked to metabolic-related disorders.

Some embodiments of the present invention include methods of treatment of a disease, disorder or condition as described herein comprising administering to an individual in need of such treatment a therapeutically effect amount or dose of a compound of the present invention in combination with at least one pharmaceutical agent selected from the group consisting of: sulfonylureas, meglitinides, biguanides, α-glucosidase inhibitors, peroxisome proliferator-activated receptor-γ (i.e., PPAR-γ) agonists, insulin, insulin analogues, HMG-CoA reductase inhibitors, cholesterol-lowering drugs (for example, fibrates that include: fenofibrate, bezafibrate, gemfibrozil, clofibrate and the like; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors, angiotensin II receptor antagonists and adiponectin. In some embodiments, the pharmaceutical composition further comprises one or more agents selected from the group consisting of α-glucosidase inhibitors, aldose reductase inhibitors, biguanides, HMG-CoA reductase inhibitors, squalene synthesis inhibitors, fibrates, LDL catabolism enhancers, angiotensin converting enzyme inhibitors, insulin secretion enhancers, thiazolidinediones and DP receptor antagonists.

One aspect of the present invention encompasses pharmaceutical compositions comprising at least one compound of the present invention, as described herein. In some embodiments, the pharmaceutical composition further comprises one or more agents selected from the group consisting of, for example, α-glucosidase inhibitors, aldose reductase inhibitors, biguanides, HMG-CoA reductase inhibitors, squalene synthesis inhibitors, fibrates, LDL catabolism enhancers, angiotensin converting enzyme inhibitors, insulin secretion enhancers and thiazolidinediones.

Suitable pharmaceutical agents that can be used in conjunction with compounds of the present invention include sulfonylureas. The sulfonylureas (SU) are drugs which promote secretion of insulin from pancreatic β cells by transmitting signals of insulin secretion via SU receptors in the cell membranes. Examples of the sulfonylureas include glyburide, glipizide, glimepiride and other sulfonylureas known in the art.

Suitable pharmaceutical agents that can be used in conjunction with compounds of the present invention include the meglitinides. The meglitinides are benzoic acid derivatives represent a novel class of insulin secretagogues. These agents target postprandial hyperglycemia and show comparable efficacy to that of sulfonylureas in reducing $HbA_{1c}$. Examples of meglitinides include repaglinide, nateglinide and other meglitinides known in the art.

Suitable pharmaceutical agents that can be used in conjunction with compounds of the present invention include the peroxisome proliferators-activated receptor-γ (i.e., PPAR-γ) agonists. The peroxisome proliferators-activated receptor-γ agonists represent a class of compounds that activates the nuclear receptor PPAR-γ and therefore regulate the transcription of insulin-responsive genes involved in the control of glucose production, transport and utilization. Agents in the class also facilitate the regulation of fatty acid metabolism. Examples of PPAR-γ agonists include rosiglitazone, pioglitazone, tesaglitazar, netoglitazone, GW-409544, GW-501516 and PPAR-γ agonists known in the art.

Suitable pharmaceutical agents that can be used in conjunction with compounds of the present invention include DP receptor antagonists. DP receptor antagonists include those described in WO01/79169, WO03/062200 WO01/66520, WO03/022814, WO03/078409, WO2004/103370, EP 1305286, WO02/094830, and the like. Other representative DP antagonist compounds can be found in WO04/103370.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

In some embodiments, the present invention is directed to processes for preparing a pharmaceutical composition comprising admixing a compound described herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically-acceptable carriers, outside those mentioned herein, are known in the art; for example, see Remington, *The Science and Practice of Pharmacy*, 20th Edition, 2000, Lippincott Williams and Wilkins, (Editors: Gennaro et al.)

While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for abroad sorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a solvate or physiologically functional derivative thereof can be used as active ingredients in pharmaceutical compositions, specifically as GPR81 receptor modulators. By the term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary within wide limits and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the present invention. Representative doses of the present invention include, but not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the present invention and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt, solvate or hydrate of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size. The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, abroad sorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like, such as those pharmaceutically acceptable salts listed in *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral abroad sorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

It is noted that when the GPR81 receptor agonists are utilized as active ingredients in a pharmaceutical composition, these are not intended for use only in humans, but in other non-human mammals as well. Indeed, recent advances in the area of animal health-care mandate that consideration be given for the use of active agents, such as GPR81 receptor agonists, for the treatment of an GPR81 receptor associated disease or disorder in companionship animals (e.g., cats, dogs, etc.) and in livestock animals (e.g., cows, chickens, fish, etc.) Those of ordinary skill in the art are readily credited with understanding the utility of such compounds in such settings.

Hydrates and Solvates

It is understood that when the phrase "pharmaceutically acceptable salts, solvates and hydrates" is used when referring to a particular formula herein, it is intended to embrace solvates and/or hydrates of compounds of the particular formula, pharmaceutically acceptable salts of compounds of the particular formula as well as solvates and/or hydrates of pharmaceutically acceptable salts of compounds of the particular formula.

The compounds of the present invention can be administrated in a wide variety of oral and parenteral dosage forms. It will be apparent to those skilled in the art that the following dosage forms may comprise, as the active component, either a compound of the invention or a pharmaceutically acceptable salt or as a solvate or hydrate thereof. Moreover, various hydrates and solvates of the compounds of the invention and their salts will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: *Polymorphism in Pharmaceutical Solids*, ed. Harry G. Brittan, Vol. 95, Marcel Dekker, Inc., New York, 1999, incorporated herein by reference in its entirety. Accordingly, one aspect of the present invention pertains to hydrates and solvates of compounds of Formula (Ia) and/or their pharmaceutical acceptable salts, as described herein, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Other Utilities

Another object of the present invention relates to radio-labeled compounds of the present invention that would be useful not only in radio-imaging but also in assays, both in vitro and in vivo, for localizing and quantitating the GPR81 receptor in tissue samples (including human) and for identifying GPR81 receptor ligands by inhibition binding of a radio-labeled compound. It is a further object of this invention to develop novel GPR81 receptor assays of which comprise such radio-labeled compounds.

The present invention embraces isotopically-labeled compounds of the present invention. Isotopically or radio-labeled compounds are those which are identical to compounds disclosed herein, but for the fact that one or more atoms are replaced or substituted by an atom having an atomic mass or mass number different from the atomic mass or mass number most commonly found in nature. Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{75}$Br, $^{76}$Br, $^{77}$Br, $^{82}$Br, $^{123}$I, $^{124}$I, $^{125}$I and $^{131}$I. The radionuclide that is incorporated in the instant radio-labeled compounds will depend on the specific application of that radio-labeled compound. For example, for in vitro GPR81 receptor labeling and competition assays, compounds that incorporate $^3$H, $^{14}$C, $^{82}$Br, $^{125}$I, $^{131}$I or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound of Formula (Ia), that has incorporated at least one radionuclide; in some embodiments the radionuclide is selected from the group consisting of $^3$H, $^{14}$C, $^{125}$I, $^{35}$S and $^{82}$Br.

Certain isotopically-labeled compounds of the present invention are useful in compound and/or substrate tissue distribution assays. In some embodiments the radionuclide $^3$H and/or $^{14}$C isotopes are useful in these studies. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3$H]: This procedure is rather inexpensive and requires precursors containing reducible functional groups such as aldehydes, ketones, lactones, esters and the like.

C. Reduction with Lithium Aluminum Hydride [$^3$H]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{125}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}$I at the ortho position of a phenol as reported by Collier, T. L. and co-workers in *J. Labelled Compd. Radiopharm.*, 1999, 42, S264-S266.

C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A representative procedure was reported by Le Bas, M.-D. and co-workers in *J. Labelled Compd. Radiopharm.* 2001, 44, S280-S282.

A radiolabeled GPR81 receptor compound of Formula (Ia) can be used in a screening assay to identify/evaluate compounds. In general terms, a newly synthesized or identified compound (i.e., test compound) can be evaluated for its ability to reduce binding of the "radio-labeled compound of Formula (Ia)" to the GPR81 receptor. Accordingly, the ability of a test compound to compete with the "radio-labeled compound of Formula (Ia)" for the binding to the GPR81 receptor directly correlates to its binding affinity.

The labeled compounds of the present invention bind to the GPR81 receptor. In one embodiment the labeled compound has an IC$_{50}$ less than about 500 µM, in another embodiment the labeled compound has an IC$_{50}$ less than about 100 µM, in yet another embodiment the labeled compound has an IC$_{50}$ less than about 10 µM, in yet another embodiment the labeled compound has an IC$_{50}$ less than about 1 µM and in still yet another embodiment the labeled inhibitor has an IC$_{50}$ less than about 0.1 µM.

Other uses of the disclosed receptors and methods will become apparent to those in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1

Syntheses of Compounds of the Present Invention

Figure 2:
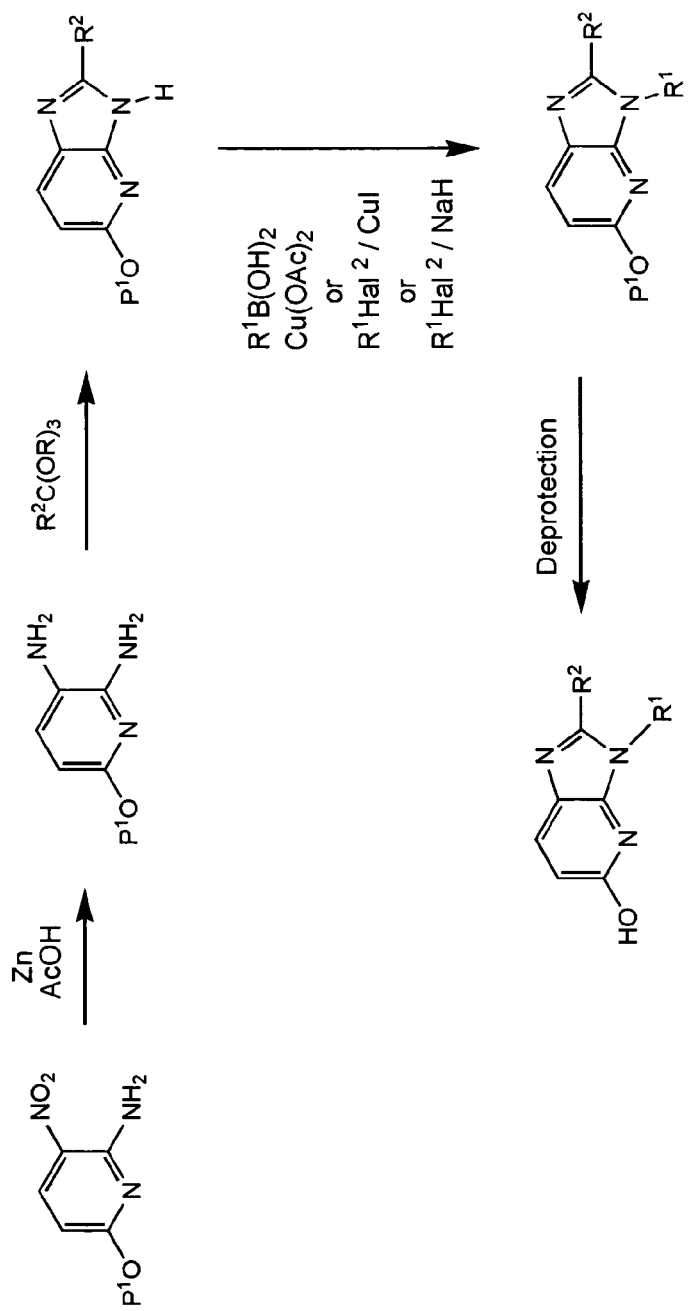
FIG. 2 shows a general method of preparing compounds of the present invention. The partially unsubstituted core structure of the present invention is obtained following the reduction of the nitro group of the starting material and ensuing condensation of the di-amino intermediate with the corresponding formates. The final compounds are prepared by introducing the $R^1$ group via a variety of methods. Subsequent deprotection affords compounds of the present invention of formula (Ia).
Figure 3:
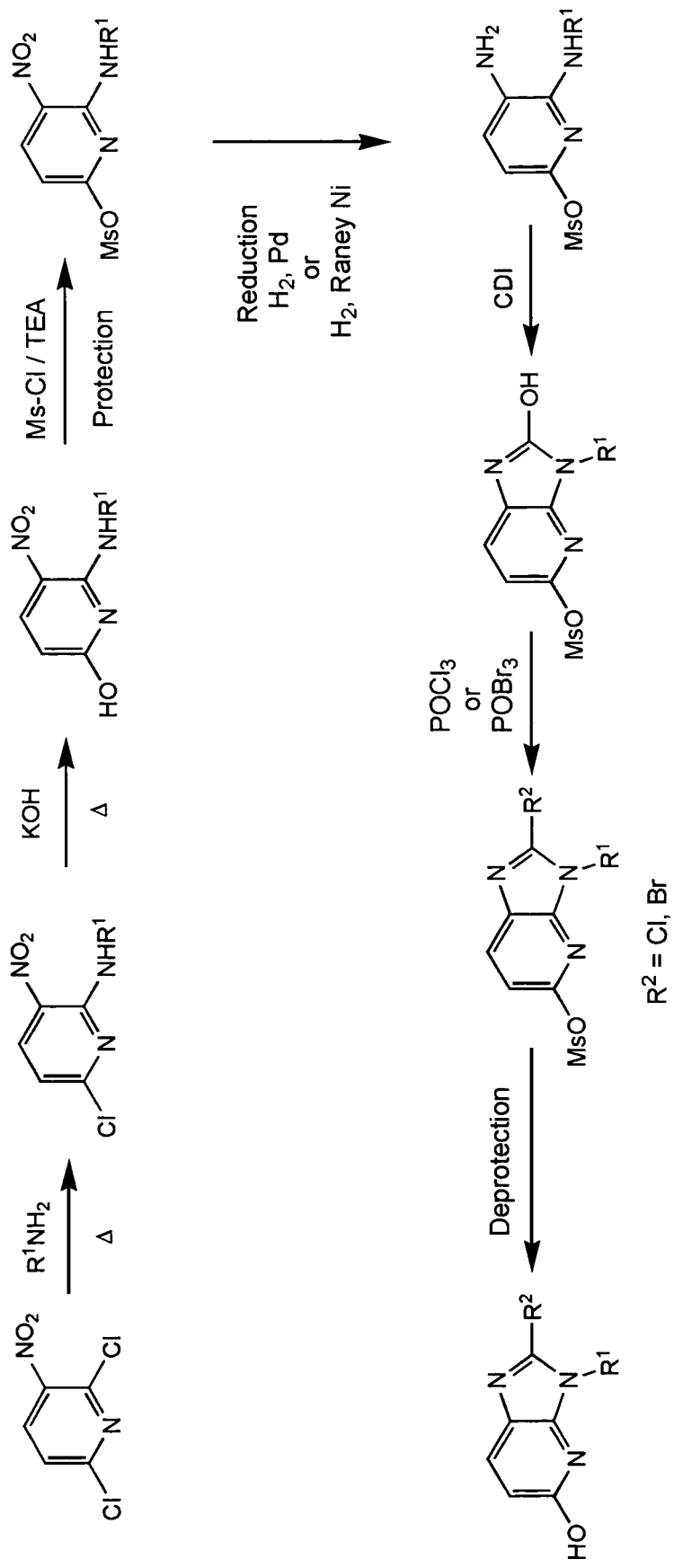
FIG. 3 shows general methods of preparing compounds of the present invention. The 2,6-dichloro-3-nitropyridine starting material undergoes one initial nucleophilic displacement with a primary amine, followed by a second nucleophilic substitution with potassium hydroxide. Following protection of the alcohol moiety and reduction of the nitro group, the di-amino intermediate is condensed with 1,1'-carbonyldiimidazole (CDI) and the resulting hydroxyl group is converted to the corresponding halogen. Subsequent deprotection affords compounds of the present invention of formula (Ia).
Figure 4:
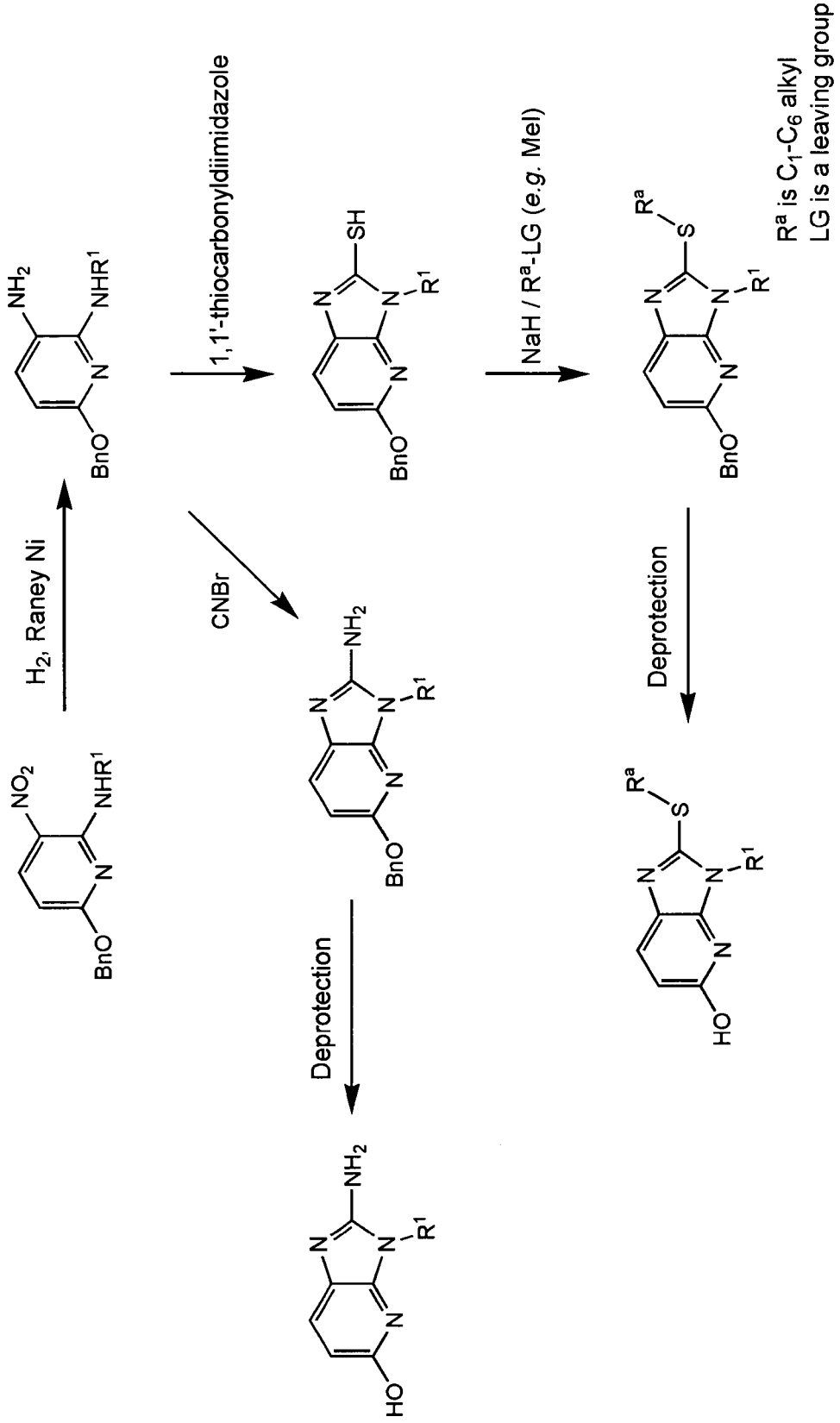
FIG. 4 shows general methods for preparing compounds of the present invention. Following the reduction of the nitro group, the di-amino intermediate is condensed with cyanogen bromide or 1,1'-thiocarbonyldiimidazole. In the former route, the final compounds are obtained after deprotection. In the latter, the final compounds are obtained following alkylation (e.g. methylation) and deprotection.
Figure 5:
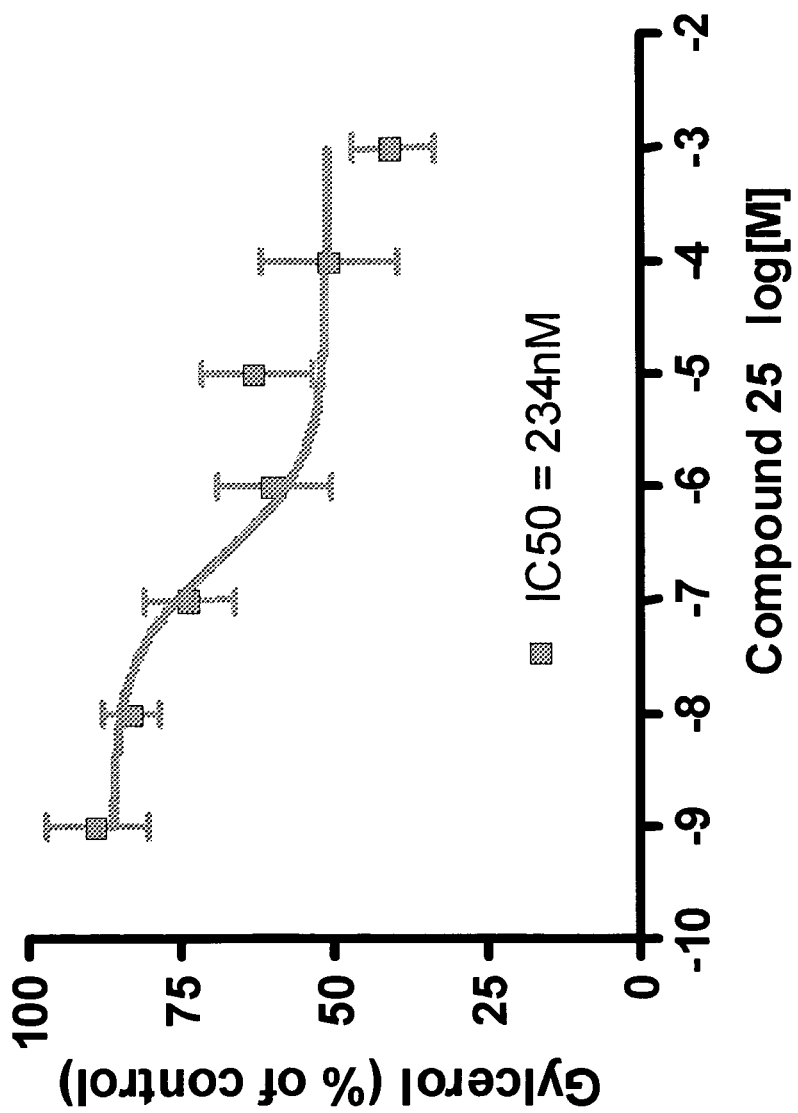
FIG. 5 shows inhibition of lipolysis in rat epididymal adipocytes in vitro by compound 25, a GPR81 agonist.
Figure 6:
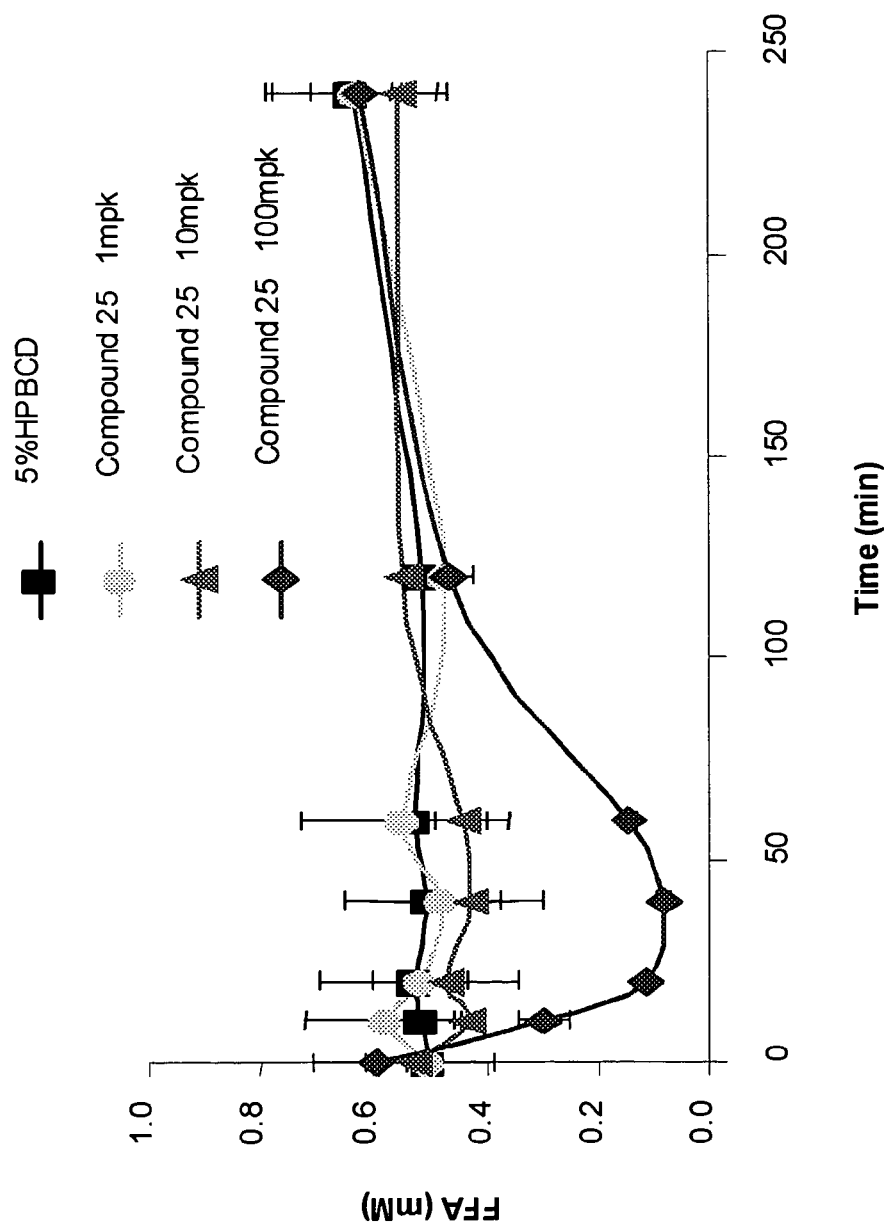
FIG. 6 shows a significant decrease of circulating free fatty acids in rats after injection of 100 mpk of compound 25, a GPR81 agonist.
Figure 7:
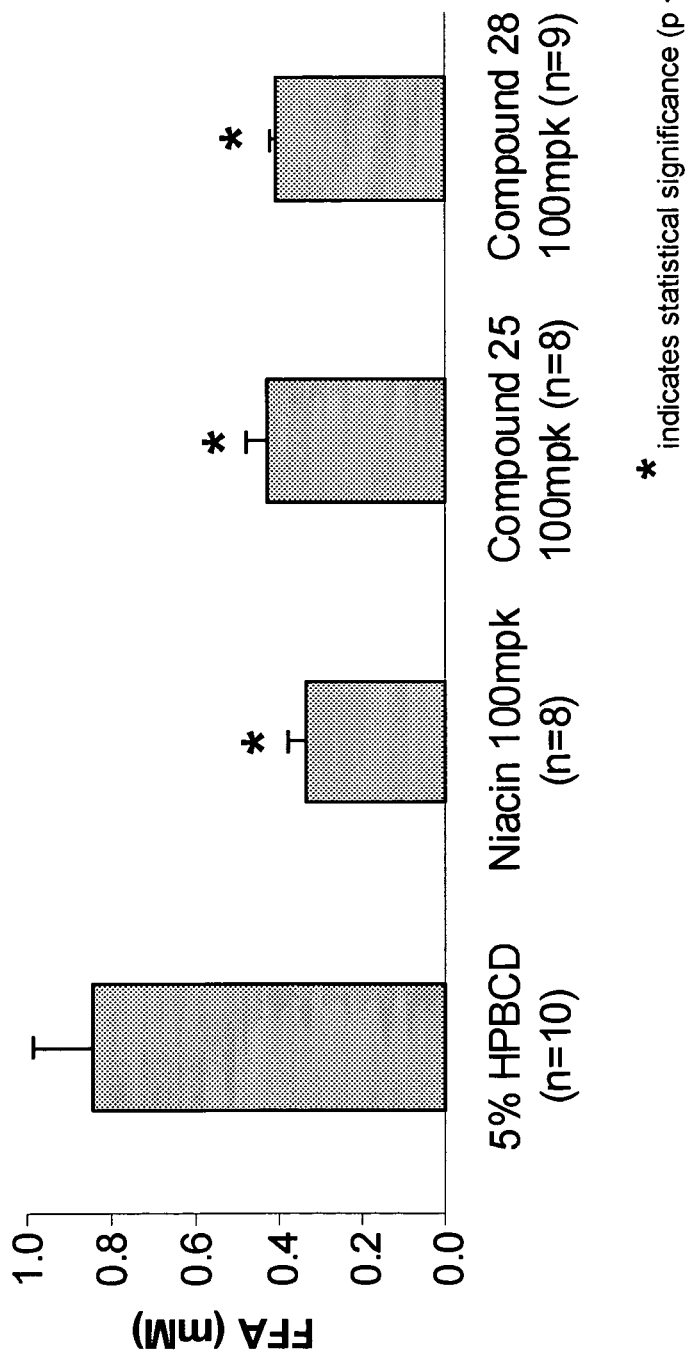
FIG. 7 shows a significant decrease of circulating free fatty acids in mice by compound 25 and compound 28, two GPR81 agonists. The drug Niacin is shown for comparison.

Illustrated syntheses for compounds of the present invention are shown in FIGS. 1 through 4 where the variables have the same definitions as used throughout this disclosure.

The compounds of the invention and their syntheses are further illustrated by the following examples. The following examples are provided to further define the invention without, however, limiting the invention to the particulars of these examples. The compounds described herein, supra and infra, are named according to the CS ChemDraw Ultra Version 7.0.1, AutoNom version 2.2, CS ChemDraw Ultra Version 9.0.3 or CS ChemDraw Ultra Version 9.0.7. In certain instances common names are used and it is understood that these common names would be recognized by those skilled in the art.

Chemistry:

Proton nuclear magnetic resonance ($^1$H NMR) spectra were recorded on a Bruker Avance-400 equipped with a QNP (Quad Nucleus Probe) or a BBI (Broad Band Inverse) and z-gradient. Proton nuclear magnetic resonance ($^1$H NMR) spectra were also recorded on a Bruker Avance-500 equipped a BBI (Broad Band Inverse) and z-gradient. Chemical shifts are given in parts per million (ppm) with the residual solvent signal used as reference. NMR abbreviations are used as follows: s=singlet, d=doublet, dd=doublet of doublets, ddd=doublet of doublet of doublets, dt=doublet of triplets, t=triplet, td=triplet of doublets, tt=triplet of triplets, q=quartet, qd=quartet of doublets, m=multiplet, broad s=broad singlet, bt=broad triplet. Microwave irradiations were carried out using a Smith Synthesizer™ or an Emrys Optimizer™ (Biotage). Thin-layer chromatography (TLC) was performed on silica gel 60 $F_{254}$ (Merck), preparatory thin-layer chromatography (prep TLC) was preformed on PK6F silica gel 60 A 1 mm plates (Whatman) and column chromatography was carried out on a silica gel column using Kieselgel 60, 0.063-0.200 mm (Merck). Evaporation was done under reduced pressure on a Büchi rotary evaporator.

LCMS spec: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2.

Example 1.1

Preparation of
3-Cycloheptyl-3H-imidazo[4,5-b]pyridin-5-ol
(Compound 48)

Step A. Preparation of
6-(benzyloxy)pyridine-2,3-diamine

To a solution of 6-(benzyloxy)-3-nitropyridin-2-amine (*J. Med. Chem.* 1997, 40, 1808) (22.67 g, 92.44 mmol) in AcOH (300 mL) was added zinc dust (24.18 g, 369.7 mmol) in four portions over 10 min while cooling in an ice bath. The mixture was then allowed to warm to room temperature and stirred for 2 h. The mixture was filtered and the solvent was removed under reduced pressure. The product was taken up in EtOAc and washed with saturated NaHCO$_3$ solution and brine. The organics were dried over MgSO$_4$, filtered and concentrated to yield the title compound as a black solid (19.31 g). $^1$H NMR (400 MHz, DMSO-d$_6$) δ ppm 4.13 (s, 2H), 5.14 (s, 2H), 5.39 (s, 2H), 5.86 (d, J=7.9 Hz, 1H), 6.77 (d, J=7.9 Hz, 1H), 7.28 (m, 1H), 7.34 (t, J=7.6 Hz, 2H), 7.40 (m, 2H).

Step B. Preparation of
5-(Benzyloxy)-3H-imidazo[4,5-b]pyridine

To a solution of 6-(benzyloxy)pyridine-2,3-diamine (19.31 g, 89.71 mmol) in THF (300 mL) was added trimethyl orthoformate 99% (99.16 ml, 897.1 mmol) and TFA (345 µL, 4.49 mmol) at room temperature. After stirring for 24 h the solvent was removed under reduced pressure. The residue was taken up in 2 M HCl and EtOAc. The two layers were separated. The organic layer was washed with 2 M HCl and the combined aqueous layers were then made basic by the careful addition of 2 N NaOH. The precipitate was collected by vacuum filtration to give the title compound as a white solid (16.39 g). LCMS m/z=226.3, [M+H]$^+$; $^1$H NMR (400 MHz, DMSO-d$_6$) δ ppm 5.40 (s, 2H), 6.91 (d, J=9.1 Hz, 1H), 7.32 (m, 1H), 7.38 (m, 2H), 7.48 (m, 2H), 8.09 (d, J=9.1 Hz, 1H), 8.79 (s, 1H).

Step C: Preparation of
3-Cycloheptyl-3H-imidazo[4,5-b]pyridin-5-ol
(Compound 48)

5-(Benzyloxy)-3H-imidazo[4,5-b]pyridine (2.00 g, 8.88 mmol) was dissolved in THF and NaH (0.18 g, 14.7 mmol) was added portionwise. The resulting mixture was heated in a sealed tube for 1 h and then cooled to room temperature. Bromocycloheptane (3.14 g, 17.8 mmol) was added and the reaction was heated to 70° C. overnight. The solution was then diluted with ether and washed with water. The aqueous layer was back extracted with additional ether and the combined organic portions were washed with brine, dried over MgSO$_4$ and purified by preparative HPLC. The resulting 5-(benzyloxy)-3-cycloheptyl-3H-imidazo[4,5-b]pyridine was then dissolved in MeOH with catalytic amount of 5% Pd/C and excess ammonium formate. The reaction mixture was heated to 80° C. until the reaction was complete. The solvent was removed under reduced pressure and the residue purified via preparative HPLC to give the title compound (0.356 g). LCMS m/z=232.1 [M+H]$^+$; $^1$H NMR (400 MHz, acetonitrile-d$_3$) δ ppm 1.55-1.80 (m, 6H), 1.80-1.90 (m, 2H), 2.05-2.20 (m, 4H), 4.50-4.60 (m, 1H), 6.57 (d, J=8.6 Hz, 1H), 7.85 (d, J=8.6 Hz, 1H), 7.96 (s, 1H).

Example 1.2

Preparation of
3-Cyclopentyl-3H-imidazo[4,5-b]pyridin-5-ol
(Compound 47)

5-(Benzyloxy)-3H-imidazo[4,5-b]pyridine (0.300 g, 1.33 mmol) was dissolved in THF and NaH (0.050 g, 2.0 mmol) was added portionwise. The resulting mixture was heated in a sealed tube for 1 h and then cooled to room temperature. Bromocyclopentane (0.20 g, 17.8 mmol) was added and the reaction was heated to 70° C. overnight. The solution was then diluted with ether and washed with water. The aqueous layer was back extracted with additional ether and the combined organic portions were washed with brine, dried over MgSO$_4$ and purified by preparative HPLC. The resulting 5-(benzyloxy)-3-cycloheptyl-3H-imidazo[4,5-b]pyridine was then dissolved in DCM and diluted with excess sulfuric acid. The resulting solution was stirred for 30 minutes at room temperature then acidified with the addition of 1 M aqueous hydrochloric acid. The solvent was removed from the organic layer and the residue was purified via preparative HPLC to give the title compound (0.0284 g). LCMS m/z=204.31 [M+H]$^+$; $^1$H NMR (400 MHz, DMSO-d$_6$) δ ppm 1.65-1.80 (m, 2H), 1.80-1.95 (m, 2H), 2.0-2.1 (m, 2H), 2.15-2.30 (m, 2H), 4.95-5.05 (m, 1H), 6.88 (d, J=8.8 Hz, 1H), 8.13 (d, J=8.8 Hz, 1H), 9.35 (s, 1H).

Example 1.3

Preparation of 3-(Tetrahydro-2H-pyran-4-yl)-3H-imidazo[4,5-b]pyridin-5-ol (Compound 68)

Step A: Preparation of 6-Chloro-3-nitro-N-(tetrahydro-2H-pyran-4-yl)pyridin-2-amine 2,6-Dichloro-3-nitropyridine (0.222 g, 1.15 mmol), 4-aminotetrahydropyran (0.109 g, 1.08 mmol) and DIEA (0.300 mL, 1.72 mmol) were taken up in ethanol (3.0 mL) and heated to 175° C. for 15 minutes in a heavy walled sealed tube under microwave irradiation. The solvent was removed under reduced pressure and the residual solid was purified by preparative HPLC to give the title compound (0.186 g). LCMS m/z=258.3 [M+H]$^+$; $^1$H NMR (400 MHz, CDCl$_3$) δ ppm 1.60-1.75 (m, 2H), 2.8 (d, J=12.4 Hz, 2H), 3.60 (t, J=11.4 Hz, 2H), 4.02 (d, J=11.8 Hz, 2H), 4.30-4.45 (m, 1H), 6.63 (d, J=8.6 Hz, 1H), 8.29 (d, J=5.8 Hz, 1H), 8.35 (d, J=8.6 Hz, 1H).

Step B: Preparation of 5-Nitro-6-(Tetrahydro-2H-pyran-4-ylamino)pyridin-2-ol 6-Chloro-3-nitro-N-(tetrahydro-2H-pyran-4-yl)pyridin-2-amine (0.186 g, 0.722 mmol), 1 M aqueous potassium hydroxide solution (8.0 mL, 16.0 mmol) and dioxane (20 mL) were heated to 100° C. for 4 h. After cooling, the pH was adjusted to ~7 and the mixture was extracted with EtOAc. The EtOAc extract was concentrated under reduced pressure to give the title compound (0.170 g). LCMS m/z=240.3 [M+H]$^+$; $^1$H NMR (400 MHz, methanol-d$_4$) δ ppm 1.65-1.80 (m, 2H), 2.05-2.15 (m, 2H), 3.60-3.70 (m, 2H), 4.00-4.10 (m, 2H), 4.20-4.30 (m, 1H), 5.92 (d, J=9.8 Hz, 1H), 8.32 (d, J=9.8 Hz, 1H).

Step C: Preparation of 3-(Tetrahydro-2H-pyran-4-yl)-3H-imidazo[4,5-b]pyridin-5-ol (Compound 68)

5-Nitro-6-(tetrahydro-2H-pyran-4-ylamino)pyridin-2-ol (0.173 g, 0.723 mmol) and methanol (160 mL) were stirred at 25° C. for 4 h with excess Raney nickel and under an atmosphere of hydrogen. After 4 h the solution was filtered by vacuum filtration through Celite® and the solvent was removed under reduced pressure. The intermediate 5-amino-6-(tetrahydro-2H-pyran-4-ylamino)pyridin-2-ol was then taken up in trimethyl orthoformate (20.0 mL, 183 mmol), and trifluoroacetic acid (0.05 ml, 0.649 mmol) was added. The solution was stirred at room temperature overnight. The solvent was removed under reduced pressure and the residue was purified by preparative HPLC to give the title compound (0.0246 g). LCMS m/z=220.0 [M+H]$^+$; $^1$H NMR (400 MHz, acetonitrile-d$_3$) δ ppm 2.10-2.20 (m, 2H), 2.31 (qd, J$_1$=12.4 Hz, J$_2$=4.7 Hz, 2H), 3.59 (td, J$_1$=12.0 Hz, J$_2$=1.9 Hz, 2H), 4.11 (dd, J$_1$=11.8 Hz, J$_2$=4.5 Hz, 2H), 4.80-4.90 (m, 1H), 6.98 (d, J=8.9 Hz, 1H), 8.18 (d, J=8.9 Hz, 1H), 8.56 (s, 1H).

Example 1.4

Preparation of 3-(Tetrahydro-2H-thiopyran-4-yl)-3H-imidazo[4,5-b]pyridin-5-ol (Compound 97)

Step A: Preparation of 6-Chloro-3-nitro-N-(tetrahydro-2H-thiopyran-4-yl)pyridin-2-amine 2,6-Dichloro-3-nitropyridine (0.500 g, 2.59 mmol), tetrahydro-2H-thiopyran-4-amine (0.304 g, 2.59 mmol) and DIEA (0.91 mL, 5.19 mmol) were taken up in ethanol (2.0 mL) and heated to 80° C. for 18 h in a sealed tube. The reaction solution was chilled to form a precipitate. The precipitate was collected by vacuum filtration to give the title compound (0.360 g) LCMS m/z=274.1 [M+H]$^+$; $^1$H NMR (400 MHz, methanol-d$_4$) δ ppm 1.70-1.85 (m, 2H), 2.20-2.35 (m, 2H), 2.60-2.90 (m, 4H), 3.90-4.10 (m, 1H), 5.84 (d, J=10.0 Hz, 1H), 8.24 (d, J=9.3 Hz, 1H).

Step B: Preparation of 5-Nitro-6-(tetrahydro-2H-thiopyran-4-ylamino)pyridin-2-ol From 6-chloro-3-nitro-N-(tetrahydro-2H-thiopyran-4-yl)pyridin-2-amine, prepared in a similar manner as the one described in Example 1.3, Step B, the title compound was obtained. LCMS m/z=256.1 [M+H]$^+$; $^1$H NMR (400 MHz, methanol-d$_4$) δ ppm 1.7-1.85 (m, 2H), 2.25-2.35 (m, 2H), 2.6-3.0 (m, 4H), 3.95-4.05 (m, 1H), 5.84 (d, J=9.8 Hz, 1H), 8.24 (d, J=9.8 Hz, 1H).

Step C: Preparation of 3-(Tetrahydro-2H-thiopyran-4-yl)-3H-imidazo[4,5-b]pyridin-5-ol (Compound 97)

From 5-nitro-6-(tetrahydro-2H-thiopyran-4-ylamino)pyridin-2-ol, prepared in a similar manner as the one described in Example 1.3, Step C, the title compound was obtained. LCMS m/z=235.8 [M+H]$^+$; $^1$H NMR (400 MHz, acetonitrile-d$_3$) δ ppm 2.30-2.50 (m, 4H), 2.80 (d, J=13.6 Hz, 2H), 2.90-3.0 (m, 2H), 4.50-4.60 (m, 1H), 6.85 (d, J=8.8 Hz, 1H), 8.09 (d, J=8.7 Hz, 1H), 8.57 (s, 1H).

Example 1.5

Preparation of 3-(Bicyclo [2.2.1]heptan-2-yl)-3H-imidazo[4,5-b]pyridin-5-ol (Compound 98)

From exo-2-aminonorbornane and 2,6-dichloro-3-nitropyridine, prepared in a similar manner as the one described in Example 1.3, the title compound was obtained. LCMS m/z=230.3 [M+H]$^+$; $^1$H NMR (400 MHz, acetonitrile-d$_3$) δ ppm 1.30-1.50 (m, 3H), 1.55-1.80 (m, 4H), 2.05-2.15 (m, 1H), 2.48 (s, 1H), 2.65 (s, 1H), 4.53-4.60 (m, 1H), 6.86 (d, J=8.7 Hz, 1H), 8.09 (d, J=8.8 Hz, 1H), 8.62 (s, 1H).

Example 1.6

Preparation of 3-Cyclohexyl-3H-imidazo[4,5-b]pyridin-5-ol (Compound 92)

From aminocyclohexane and 2,6-dichloro-3-nitropyridine, prepared in a similar manner as the one described in Example 1.4, the title compound was obtained. LCMS m/z=217.9 [M+H]$^+$; $^1$H NMR (400 MHz, acetonitrile-d$_3$) δ ppm 1.35 (tt, J$_1$=13.0 Hz, J$_2$=3.3 Hz, 2H), 1.45-1.60 (m, 4H), 1.75-1.85 (m, 2H), 2.15-2.25 (m, 2H), 4.50-4.65 (m, 1H), 6.95 (d, J=8.9 Hz, 1H), 8.15 (d, J=9.2 Hz, 1H), 8.78 (s, 1H).

Example 1.7

Preparation of 3-Cyclooctyl-3H-imidazo[4,5-b]pyridin-5-ol (Compound 94)

From aminocyclooctane and 2,6-dichloro-3-nitropyridine, prepared in a similar manner as the one described in Example 1.4, the title compound was obtained. LCMS m/z=246.1 [M+H]$^+$; $^1$H NMR (400 MHz, acetonitrile-d$_3$) δ ppm 1.60-1.80 (m, 8H), 1.80-1.90 (m, 2H), 2.00-2.10 (m, 2H), 2.20-2.30 (m, 2H), 4.75-4.85 (m, 1H), 6.87 (d, J=8.8 Hz, 1H), 8.11 (d, J=8.8 Hz, 1H), 8.64 (s, 1H).

Example 1.8

Preparation of 2-Amino-3-cycloheptyl-3H-imidazo[4,5-b]pyridin-5-ol (Compound 93)

5-Amino-6-(cycloheptylamino)pyridin-2-ol, prepared in a similar manner as the one described in Example 1.3 from 6-(cycloheptylamino)-5-nitropyridin-2-ol (0.225 g, 0.895 mmol), was taken up in ethanol (20 mL). Cyanogen bromide (0.153 g, 1.34 mmol) was then added. The resulting solution was stirred at room temperature overnight. The solvent was removed under reduced pressure. The residue was purified by preparative HPLC to give the title compound (0.004 g). LCMS m/z=247.0 [M+H]$^+$; $^1$H NMR (400 MHz, acetonitrile-d$_3$) δ ppm 1.50-1.80 (m, 6H), 1.80-2.05 (m, 4H), 2.45-2.55 (m, 2H), 4.25-4.35 (m, 1H), 6.55 (d, J=8.5 Hz, 1H), 7.59 (d, J=8.5 Hz, 1H).

Example 1.9

Preparation of 3-Cycloheptyl-2-methyl-3H-imidazo [4,5-b]pyridin-5-ol (Compound 95)

5-Amino-6-(cycloheptylamino)pyridin-2-ol, prepared in a similar manner as the one described in Example 1.3 from 6-(cycloheptylamino)-5-nitropyridin-2-ol, was taken up in trimethylorthoacetate and stirred at room temperature overnight. The solvent was removed under reduced pressure and the residue was purified by preparative HPLC to give the title compound. LCMS m/z=246.1 [M+H]$^+$; $^1$H NMR (400 MHz, acetonitrile-d$_3$) δ ppm 1.55-1.80 (m, 6H), 1.85-2.05 (m, 4H), 2.50-2.60 (m, 2H), 2.80 (s, 3H), 4.50-4.60 (m, 1H), 6.84 (d, J=8.8 Hz, 1H), 8.01 (d, J=8.8 Hz, 1H).

Example 1.10

Preparation of 3-(4-Hydroxycyclohexyl)-3H-imidazo [4,5-b]pyridin-5-ol (Compound 90)

Step A: Preparation of trans-4-(6-Chloro-3-nitropyridin-2-ylamino)cyclohexanol, trifluoroacetate 2,6-Dichloro-3-nitropyridine (0.500 g, 2.59 mmol), 4-aminocyclohexanol (0.298 g, 2.59 mmol), DIEA (1.00 ml, 5.73 mmol) and ethanol (2.0 ml) were heated to 80° C. for 18 h in a sealed flask. The solvent was removed under reduced pressure and the residual solid was purified by preparative HPLC to give the title compound (0.894 g). LCMS m/z=272.2 [M+H]$^+$; $^1$H NMR (400 MHz, acetonitrile-d$_3$) δ ppm 1.3-1.52 (m, 4H), 2.0-2.1 (m, 2H), 2.15-2.2 (m, 2H), 2.74 (br s, 1H), 6.67 (d, J=8.6 Hz, 1H), 8.16 (br s, 1H), 8.36 (d, J=8.6 Hz, 1H).

Step B: Preparation of trans 6-(4-Hydroxycyclohexylamino)-5-nitropyridin-2-ol

From trans-4-(6-chloro-3-nitropyridin-2-ylamino)cyclohexanol, trifluoroacetate, prepared in a similar manner as the one described in Example 1.3, Step B, the title compound was obtained. LCMS m/z=254.4 [M+H]$^+$.

Step C: Preparation of 3-(4-Hydroxycyclohexyl)-3H-imidazo[4,5-b]pyridin-5-ol (Compound 90)

From trans-6-(4-hydroxycyclohexylamino)-5-nitropyridin-2-ol, prepared in a similar manner as the one described in Example 1.3, Step C, the title compound was obtained. LCMS m/z=234.2 [M+H]$^+$; $^1$H NMR (400 MHz, acetonitrile-d$_3$) δ ppm 1.45-1.60 (m, 2H), 2.00-2.15 (m, 4H), 2.20-2.30 (m, 2H), 3.65-3.75 (m, 1H), 4.57-4.67 (m, 1H), 6.87 (d, J=8.9 Hz, 1H), 8.13 (d, J=8.9 Hz, 1H), 8.85 (s, 1H).

Example 1.11

Preparation of 2-(5-Hydroxy-3H-imidazo[4,5-b] pyridin-3-yl)cyclohexanone (Compound 91)

Step A: Preparation of 2-(5-(Benzyloxy)-3H-imidazo [4,5-b]pyridin-3-yl)cyclohexanone From 2-chlorocyclohexanone and 5-(benzyloxy)-3H-imidazo[4,5-b]pyridine, prepared in a similar manner as the one described in Example 1.1, Step C, the title compound was obtained. LCMS m/z=322.2 [M+H]$^+$.

Step B: Preparation of 2-(5-Hydroxy-3H-imidazo[4, 5-b]pyridin-3-yl)cyclohexanone (Compound 91)

2-(5-(Benzyloxy)-3H-imidazo[4,5-b]pyridin-3-yl)cyclohexanone (0.400 g, 1.25 mmol), was taken up in ethanol (5 mL). Catalytic palladium on carbon was added, and the solution was placed under an atmosphere of hydrogen and stirred at room temperature for 2 days. The solution was then filtered through Celite®. The solvent was removed under reduced pressure and the residue was purified by preparative HPLC to give the title compound. LCMS m/z=232.1 [M+H]$^+$; $^1$H NMR (400 MHz, CDCl$_3$) δ ppm 1.80-1.95 (m, 1H), 1.95-2.10 (m, 1H), 2.15-2.35 (m, 4H), 2.70-2.50 (m, 2H), 4.50 (dd, J$_1$=13.2 Hz, J$_2$=5.7 Hz, 1H), 6.89 (d, J=8.9 Hz, 1H), 8.16 (d, J=8.9 Hz, 1H), 8.74 (s, 1H).

Example 1.12

Preparation of 2-(5-Hydroxy-3H-imidazo[4,5-b] pyridin-3-yl)cycloheptanone (Compound 70)

From 2-chlorocycloheptanone and 5-(benzyloxy)-3H-imidazo[4,5-b]pyridine, prepared in a similar manner as the one described in Example 1.11, the title compound was obtained. LCMS m/z=246.1 [M+H]$^+$; $^1$H NMR (400 MHz, DMSO-d$_6$) δ ppm 1.40-1.50 (m, 1H), 1.70-2.10 (m, 5H), 2.25-2.40 (m, 2H), 2.55-2.65 (m, 1H), 2.75-2.85 (m, 1H), 5.67 (dd, J$_1$=9.5 Hz, J$_2$=4.3 Hz, 1H), 6.77 (d, J=8.7 Hz, 1H), 8.08 (d, J=8.7 Hz, 1H), 8.88 (s, 1H).

Example 1.13

Preparation of 3-(2-Hydroxycyclohexyl)-3H-imidazo [4,5-b]pyridin-5-ol (Compound 96)

2-(5-Hydroxy-3H-imidazo[4,5-b]pyridin-3-yl)cyclohexanone (0.200 g, 0.865 mmol) was taken up in ethanol (4 mL) and sodium borohydride (9.8 mg, 0.26 mmol) added. The reaction was stirred at room temperature overnight. The solvent was removed under reduced pressure. The residue was purified by preparative HPLC to give the title compound (0.135 g). LCMS m/z=234.2 [M+H]$^+$; $^1$H NMR (400 MHz, DMSO-d$_6$) δ ppm 1.35-1.60 (m, 4H), 1.75-1.95 (m, 2H), 2.00-2.15 (m, 2H), 4.00-4.10 (m, 1H), 4.38 (q, J=8.1 Hz, 1H), 6.92 (d, J=8.8 Hz, 1H), 8.18 (d, J=8.8 Hz, 1H), 9.52 (s, 1H).

Example 1.14

Preparation of 3-(2-Hydroxycycloheptyl)-3H-imidazo[4,5-b]pyridin-5-ol (Compound 71)

From 2-(5-hydroxy-3H-imidazo[4,5-b]pyridin-3-yl)cycloheptanone, prepared in a similar manner as the one described in Example 1.13, the title compound was obtained. LCMS m/z=248.2 [M+H]$^+$; $^1$H NMR (400 MHz, DMSO-d$_6$) δ ppm 1.40-1.75 (m, 4H), 1.75-1.95 (m, 5H), 2.35-2.45 (m, 1H), 4.05-4.10 (m, 1H), 4.71 (d, J=11.8 Hz, 1H), 6.85 (d, J=8.7 Hz, 1H), 8.12 (d, J=8.8 Hz, 1H), 9.13 (s, 1H).

Example 1.15

Preparation of tert-Butyl 4-(5-Hydroxy-3H-imidazo [4,5-b]pyridin-3-yl)azepane-1-carboxylate (Compound 104)

From tert-butyl 4-aminoazepane-1-carboxylate and 2,6-dichloro-3-nitropyridine, prepared in a similar manner as the one described in Example 1.4, the title compound was obtained. LCMS m/z=333.2 [M+H]+.

Example 1.16

Preparation of 3-(4-Fluoro-2-(trifluoromethyl)phenyl)-3H-imidazo[4,5-b]pyridin-5-ol (Compound 53)

Step A: Preparation of 6-Chloro-N-(4-fluoro-2-(trifluoromethyl)phenyl)-3-nitropyridin-2-amine Sodium hydride (0.124 g, 5.18 mmol) was added to a chilled (0° C.) solution of 4-fluoro-2-(trifluoromethyl)aniline (0.464 g, 2.59 mmol) in THF (1 mL) and stirred for 30 min. 2,6-Dichloro-3-nitropyridine (0.500 g, 2.59 mmol) was then added and the reaction mixture stirred at 80° C. for 18 h. Water was added to quench excess sodium hydride and volatile solvents were removed under reduced pressure. The product was then extracted into DCM, solvent removed under reduced pressure, and the residue purified by preparative HPLC to give the title compound (0.624 g). LCMS m/z=336.0 [M+H]+; $^1$H NMR (400 MHz, CDCl$_3$) δ ppm 6.87 (d, J=8.6 Hz, 1H), 7.34 (td, J$_1$=8.4 Hz, J$_2$=3.0 Hz, 1H), 7.43 (dd, J$_1$=8.4 Hz, J$_2$=3.0 Hz, 1H), 7.94 (dd, J$_1$=9.0 Hz, J$_2$=5.0 Hz, 1H), 8.49 (d, J=8.6 Hz, 1H), 10.26 (br s, 1H).

Step B: Preparation of 6-(4-Fluoro-2-(trifluoromethyl)phenylamino)-5-nitropyridin-2-ol From 6-chloro-N-(4-fluoro-2-(trifluoromethyl)phenyl)-3-nitropyridin-2-amine, prepared in a similar manner as the one described in Example 1.3, Step B, the title compound was obtained. LCMS m/z=317.8 [M+H]+.

Step C: Preparation of 3-(4-Fluoro-2-(trifluoromethyl)phenyl)-3H-imidazo[4,5-b]pyridin-5-ol (Compound 53)

From 6-(4-fluoro-2-(trifluoromethyl)phenylamino)-5-nitropyridin-2-ol, prepared in a similar manner as the one described in Example 1.3, Step C, the title compound was obtained. LCMS m/z=298.0 [M+H]+; $^1$H NMR (400 MHz, CDCl$_3$) δ ppm 6.70 (d, J=8.8 Hz, 1H), 7.45-7.50 (m, 2H), 7.65 (d, J=7.9 Hz, 1H), 8.04 (s, 1H), 8.17 (d, J=8.8 Hz, 1H).

Example 1.17

Preparation of 3-(4-Bromo-2-(trifluoromethyl)phenyl)-3H-imidazo[4,5-b]pyridin-5-ol (Compound 57)

From 4-bromo-2-(trifluoromethyl)aniline and 2,6-dichloro-3-nitropyridine, prepared in a similar manner as the one described in Example 1.16, the title compound was obtained. LCMS m/z=358.0 [M+H]+; $^1$H NMR (400 MHz, CDCl$_3$) δ ppm 6.70 (d, J=8.5 Hz, 1H), 7.35 (d, J=8.4 Hz, 1H), 7.93 (dd, J$_1$=8.4 Hz, J$_2$=2.1 Hz, 1H), 8.08 (d, J=1.9 Hz, 1H), 8.12 (s, 1H), 8.20 (d, J=8.8 Hz, 1H).

Example 1.18

Preparation of 3-(2,3,4-Trichlorophenyl)-3H-imidazo[4,5-b]pyridin-5-ol (Compound 54)

From 2,3,4-trichloroaniline and 2,6-dichloro-3-nitropyridine, prepared in a similar manner as the one described in Example 1.16, the title compound was obtained. LCMS m/z=314.0 [M+H]+; $^1$H NMR (400 MHz, CDCl$_3$) δ ppm 6.73 (d, J=8.0 Hz, 1H), 7.38 (d, J=8.6 Hz, 1H), 7.61 (d, J=8.6 Hz, 1H), 7.97 (s, 1H), 8.09 (d, J=8.6 Hz, 1H).

Example 1.19

Preparation of 3-(4-Chloro-2-(trifluoromethyl)phenyl)-3H-imidazo[4,5-b]pyridin-5-ol (Compound 56)

From 4-chloro-2-(trifluoromethyl)aniline and 2,6-dichloro-3-nitropyridine, prepared in a similar manner as the one described in Example 1.16, the title compound was obtained. LCMS m/z=314.0 [M+H]+; $^1$H NMR (400 MHz, CDCl$_3$) δ ppm 6.82 (d, J=9.1 Hz, 1H), 7.45 (d, J=8.5 Hz, 1H), 7.79 (dd, J$_1$=8.5 Hz, J$_2$=2.2 Hz, 1H), 7.94 (d, J=2.3 Hz, 1H), 8.20 (s, 1H), 8.27 (d, J=8.9 Hz, 1H).

Example 1.20

Preparation of 3-(2,4-Bis(trifluoromethyl)phenyl)-3H-imidazo[4,5-b]pyridin-5-ol (Compound 55)

From 2,4-bis(trifluoromethyl)aniline and 2,6-dichloro-3-nitropyridine, prepared in a similar manner as the one described in Example 1.16, the title compound was obtained. LCMS m/z=348.0 [M+H]+; $^1$H NMR (400 MHz, CDCl$_3$) δ ppm 6.67 (d, J=8.8 Hz, 1H), 7.66 (d, J=8.1 Hz, 1H), 8.05-8.10 (m, 2H), 8.15-8.20 (m, 2H).

Example 1.21

Preparation of 3-(2-Chlorophenyl)-3H-imidazo[4,5-b]pyridin-5-ol (Compound 25)

Step A: Preparation of 6-Chloro-N-(2-chlorophenyl)-3-nitropyridin-2-amine

2-Chloroaniline (1.32 mL, 10.4 mmol) was added to 2,6-dichloro-3-nitropyridine (1.00 g, 5.18 mmol) in ethanol (4 mL) and the solution was heated to 180° C. for 12 minutes under microwave irradiation in a heavy walled sealed tube. After cooling to room temperature, the resulting precipitate was collected by vacuum filtration, washed with cold ethanol and dried to give the title compound (0.8650 g). LCMS m/z=284.1 [M+H]+; $^1$H NMR (400 MHz, acetonitrile-d$_3$) δ ppm 6.97 (d, J=8.6 Hz, 1H), 7.23 (td, J$_1$=7.8 Hz, J$_2$=1.6 Hz, 1H), 7.41 (td, J$_1$=8.0 Hz, J$_2$=1.5 Hz, 1H), 7.55 (dd, J$_1$=8.0 Hz, J$_2$=1.5 Hz, 1H), 8.20 (dd, J$_1$=8.2 Hz, J$_2$=1.50 Hz, 1H), 8.54 (d, J=8.6 Hz, 1H), 10.36 (broad s, 1H).

Step B: Preparation of 6-(2-Chlorophenylamino)-5-nitropyridin-2-ol

From 6-chloro-N-(2-chlorophenyl)-3-nitropyridin-2-amine (0.146 g, 0.514 mmol), prepared in a similar manner as the one described in Example 1.3, Step B, the title compound was obtained. LCMS m/z=266.0 [M+H]+. $^1$H NMR (400 MHz, acetonitrile-d$_3$) δ ppm 5.97 (d, J=10.1 Hz, 1H), 7.45-7.55 (m, 3H), 7.6-7.7 (m, 1H), 8.27 (d, J=10.1 Hz, 1H), 10.83 (br s, 1H).

Step C: Preparation of 3-(2-Chlorophenyl)-3H-imidazo[4,5-b]pyridin-5-ol (Compound 25)

From 6-(2-chlorophenylamino)-5-nitropyridin-2-ol, prepared in a similar manner as the one described in Example 1.3, Step C, the title compound was obtained. LCMS m/z=246.1 [M+H]+; $^1$H NMR (400 MHz, acetonitrile-d$_3$) δ ppm 6.81 (d, J=8.7 Hz, 1H), 7.55-7.65 (m, 3H), 7.72 (dd, $J_1$=7.8 Hz, $J_2$=1.9 Hz, 1H), 8.10 (d, J=8.7 Hz, 1H), 8.39 (s, 1H).

Example 1.22

Preparation of 3-(2-(Trifluoromethyl)phenyl)-3H-imidazo[4,5-b]pyridin-5-ol (Compound 28)

From 2-(trifluoromethyl)aniline and 2,6-dichloro-3-nitropyridine, prepared in a similar manner as the one described in Example 1.21, the title compound was obtained. LCMS m/z=280.2 [M+H]$^+$; $^1$H NMR (400 MHz, acetonitrile-d$_3$) δ ppm 6.66 (d, J=8.6 Hz, 1H), 7.58 (d, J=7.8 Hz, 1H), 7.75 (t, J=7.7 Hz, 1H), 7.85 (t, J=7.6 Hz, 1H), 7.93-8.00 (m, 3H), 8.08 (broad s, 1H).

Example 1.23

Preparation of 2-Amino-3-(2-(trifluoromethyl)phenyl)-3H-imidazo[4,5-b]pyridin-5-ol (Compound 38)

From 5-amino-6-(2-(trifluoromethyl)phenylamino)pyridin-2-ol, prepared in a similar manner as the one described in Example 1.8, the title compound was obtained. LCMS m/z=294.8 [M+H]$^+$; $^1$H NMR (400 MHz, acetonitrile-d$_3$) δ ppm 4.94 (broad s, 2H), 6.40 (d, J=8.3 Hz, 1H), 7.49 (d, J=8.3 Hz, 1H), 7.51 (d, J=7.8 Hz, 1H), 7.77 (t, J=7.7 Hz, 1H), 7.86 (t, J=7.2 Hz, 1H), 7.97 (d, J=7.3 Hz, 1H).

Example 1.24

Preparation of 2-Methyl-3-(2-(trifluoromethyl)phenyl)-3H-imidazo[4,5-b]pyridin-5-ol (Compound 39)

From 5-amino-6-(2-(trifluoromethyl)phenylamino)pyridin-2-ol, prepared in a similar manner as the one described in Example 1.9, the title compound was obtained. LCMS m/z=294.0 [M+H]$^+$; $^1$H NMR (400 MHz, acetonitrile-d$_3$) δ ppm 2.40 (s, 3H), 6.76 (d, J=8.7 Hz, 1H), 7.60 (d, J=7.9 Hz, 1H), 7.86 (t, J=7.7 Hz, 1H), 7.93 (td, $J_1$=7.6 Hz, $J_2$=1.7 Hz, 1H), 8.00-8.07 (m, 2H).

Example 1.25

Preparation of 3-(4-Fluorophenyl)-3H-imidazo[4,5-b]pyridin-5-ol (Compound 10)

Step A. Preparation of 5-(Benzyloxy)-3-(4-fluorophenyl)-3H-imidazo[4,5-b]pyridine To a solution of 5-(benzyloxy)-3H-imidazo[4,5-b]pyridine (119 mg, 0.528 mmol) in DCM (10 mL) was added triethylamine (0.147 ml, 1.06 mmol), 4-fluoroboronic acid (148 mg, 1.06 mmol), copper (II) acetate (144 mg, 0.792 mmol) and molecular sieves (4 Å powder, 150 mg). The reaction mixture was stirred for 12 h, filtered, and concentrated in vacuo. The residue was purified by silica gel chromatography to give a mixture of 5-(benzyloxy)-3-(4-fluorophenyl)-3H-imidazo[4,5b]pyridine and 5-(benzyloxy)-3-(4-fluorophenyl)-1H-imidazo[4,5b]pyridine (132 mg). LCMS m/z=320.2, [M+H]$^+$.

Step B. Preparation of 3-(4-fluorophenyl)-3H-imidazo[4,5-b]pyridin-5-ol (Compound 10)

From the mixture of 5-(benzyloxy)-3-(4-fluorophenyl)-3H-imidazo[4,5-b]pyridine and 5-(benzyloxy)-3-(4-fluorophenyl)-1H-imidazo[4,5b]pyridine, the benzyl group was removed in a similar manner as the one described in Example 1.11, Step B. Purification by preparative HPLC gave the title compound as a white solid. $^1$H NMR (400 MHz, DMSO-d$_6$) δ ppm 6.69 (d, J=8.8 Hz, 1H), 7.46 (m, 2H), 7.90 (m, 2H), 8.05 (d, J=8.8 Hz, 1H), 8.73 (s, 1H).

Example 1.26

Preparation of 3-o-tolyl-3H-imidazo[4,5-b]pyridin-5-ol (Compound 18)

From 5-(benzyloxy)-3H-imidazo[4,5-b]pyridine and o-tolylboronic acid, prepared in a similar manner as the one described in Example 1.25, Step A, 5-(benzyloxy)-3-o-tolyl-3H-imidazo[4,5-b]pyridine and 5-(benzyloxy)-1-o-tolyl-1H-imidazo[4,5-b]pyridine were obtained, which was then dissolved in DCM and diluted with excess sulfuric acid. The resulting solution was stirred for 30 minutes at room temperature then acidified with the addition of 1 M aqueous hydrochloric acid. The solvent was removed from the organic layer and the residue was purified via preparative HPLC to give the title compound. LCMS m/z=225.9 [M+H]$^+$.

Example 1.27

Preparation of 3-(3,4-Dimethylphenyl)-3H-imidazo[4,5-b]pyridin-5-ol (Compound 19)

From 5-(benzyloxy)-3H-imidazo[4,5-b]pyridine and 3,4-dimethylphenylboronic acid, prepared in a similar manner as the one described in Example 1.26, the title compound was obtained. LCMS m/z=239.9 [M+H]$^+$.

Example 1.28

Preparation of 3-(3,5-Dimethylphenyl)-3H-imidazo[4,5-b]pyridin-5-ol (Compound 20)

From 5-(benzyloxy)-3H-imidazo[4,5-b]pyridine and 3,5-dimethylphenylboronic acid, prepared in a similar manner as the one described in Example 1.26, the title compound was obtained. LCMS m/z=239.9 [M+H]$^+$.

Example 1.29

Preparation of 3-(2,5-Dimethylphenyl)-3H-imidazo[4,5-b]pyridin-5-ol (Compound 21)

From 5-(benzyloxy)-3H-imidazo[4,5-b]pyridine and 2,5-dimethylphenylboronic acid, prepared in a similar manner as the one described in Example 1.26, the title compound was obtained. LCMS m/z=239.9 [M+H]$^+$.

Example 1.30

Preparation of 3-(Thiophen-3-yl)-3H-imidazo[4,5-b]pyridin-5-ol (Compound 24)

From 5-(benzyloxy)-3H-imidazo[4,5-b]pyridine and thiophen-3-ylboronic acid, prepared in a similar manner as

Example 1.31

Preparation of 3-(2-Methoxyphenyl)-3H-imidazo[4,5-b]pyridin-5-ol (Compound 26)

From 5-(benzyloxy)-3H-imidazo[4,5-b]pyridine and 2-methoxyphenylboronic acid, prepared in a similar manner as the one described in Example 1.26, the title compound was obtained. LCMS m/z=241.9 [M+H]$^+$.

Example 1.32

Preparation of 3-(4-Fluoro-2-methylphenyl)-3H-imidazo[4,5-b]pyridin-5-ol (Compound 27)

From 5-(benzyloxy)-3H-imidazo[4,5-b]pyridine and 4-fluoro-2-methylphenylboronic acid, prepared in a similar manner as the one described in Example 1.26, the title compound was obtained. LCMS m/z=244.0 [M+H]$^+$.

Example 1.33

Preparation of 3-(2-Fluorophenyl)-3H-imidazo[4,5-b]pyridin-5-ol (Compound 29)

From 5-(benzyloxy)-3H-imidazo[4,5-b]pyridine and 2-fluorophenylboronic acid, prepared in a similar manner as the one described in Example 1.26, the title compound was obtained. LCMS m/z=230.2 [M+H]$^+$.

Example 1.34

Preparation of 3-Cyclobutyl-3H-imidazo[4,5-b]pyridin-5-ol (Compound 32)

From 5-(benzyloxy)-3H-imidazo[4,5-b]pyridine and bromocyclobutane, prepared in a similar manner as the one described in Example 1.2, the title compound was obtained. LCMS m/z=190.0 [M+H]$^+$; $^1$H NMR (400 MHz, methanol-d$_4$) δ ppm 2.07 (m, 2H), 2.67 (m, 2H), 2.78 (m, 2H), 5.24 (m, 1H), 6.95 (d, J=8.9 Hz, 1H), 8.08 (d, J=8.9 Hz, 1H), 9.33 (s, 1H).

Example 1.35

Preparation of 3-(2,4-Dimethylphenyl)-3H-imidazo[4,5-b]pyridin-5-ol (Compound 33)

From 5-(benzyloxy)-3H-imidazo[4,5-b]pyridine and 2,4-dimethylphenylboronic acid, prepared in a similar manner as the one described in Example 1.26, the title compound was obtained. LCMS m/z=239.9 [M+H]$^+$.

Example 1.36

Preparation of 3-(2,6-Dimethylphenyl)-3H-imidazo[4,5-b]pyridin-5-ol (Compound 34)

From 5-(benzyloxy)-3H-imidazo[4,5-b]pyridine and 2,6-dimethylphenylboronic acid, prepared in a similar manner as the one described in Example 1.26, the title compound was obtained. LCMS m/z=239.9 [M+H]$^+$.

Example 1.37

Preparation of 3-(2-Isopropylphenyl)-3H-imidazo[4,5-b]pyridin-5-ol (Compound 35)

From 5-(benzyloxy)-3H-imidazo[4,5-b]pyridine and 2-isopropylphenylboronic acid, prepared in a similar manner as the one described in Example 1.26, the title compound was obtained. LCMS m/z=254.1 [M+H]$^+$.

Example 1.38

Preparation of 3-(2-Ethylphenyl)-3H-imidazo[4,5-b]pyridin-5-ol (Compound 36)

From 5-(benzyloxy)-3H-imidazo[4,5-b]pyridine and 2-ethylphenylboronic acid, prepared in a similar manner as the one described in Example 1.26, the title compound was obtained. LCMS m/z=239.9 [M+H]$^+$.

Example 1.39

Preparation of 3-(3-Chloropyridin-4-yl)-3H-imidazo[4,5-b]pyridin-5-ol (Compound 41)

From 5-(benzyloxy)-3H-imidazo[4,5-b]pyridine and 2-chloropyridin-4-ylboronic acid, prepared in a similar manner as the one described in Example 1.26, the title compound was obtained. LCMS m/z=246.9 [M+H]$^+$; $^1$H NMR (400 MHz, methanol-d$_4$) δ ppm 6.74 (d, J=8.7 Hz, 1H), 7.80 (d, J=5.2 Hz, 1H), 8.01 (d, J=8.7 Hz, 1H), 8.41 (s, 1H), 8.70 (d, J=5.2 Hz, 1H), 8.87 (s, 1H).

Example 1.40

Preparation of 3-(2-Nitrophenyl)-3H-imidazo[4,5-b]pyridin-5-ol (Compound 42)

From 5-(benzyloxy)-3H-imidazo[4,5-b]pyridine and 2-nitrophenylboronic acid, prepared in a similar manner as the one described in Example 1.26, the title compound was obtained. LCMS m/z=257.1 [M+H]$^+$.

Example 1.41

Preparation of 3-(2-Bromophenyl)-3H-imidazo[4,5-b]pyridin-5-ol (Compound 43)

From 5-(benzyloxy)-3H-imidazo[4,5-b]pyridine and 2-bromophenylboronic acid, prepared in a similar manner as the one described in Example 1.26, the title compound was obtained. LCMS m/z=289.9[M+H]$^+$; $^1$H NMR (400 MHz, DMSO-d$_6$) δ ppm 6.59 (d, J=8.6 Hz, 1H), 7.52 (td, J$_1$=7.9 Hz, J$_2$=1.8 Hz, 1H), 7.61 (td, J$_1$=7.5 Hz, J$_2$=1.4 Hz, 1H), 7.67 (dd, J$_1$=7.8, J$_2$=1.7 Hz, 1H), 7.89 (dd, J$_1$=8.0, J$_2$=1.3 Hz, 1H), 8.01 (d, J=8.6 Hz, 1H), 8.28 (s, 1H), 10.86 (s, 1H).

Example 1.42

Preparation of 3-(2,6-Dichlorophenyl)-3H-imidazo[4,5-b]pyridin-5-ol (Compound 44)

From 5-(benzyloxy)-3H-imidazo[4,5-b]pyridine and 2,6-dichlorophenylboronic acid, prepared in a similar manner as the one described in Example 1.26, the title compound was obtained. LCMS m/z=279.9 [M+H]$^+$.

Example 1.43

Preparation of 3-(2,4-Dichlorophenyl)-3H-imidazo[4,5-b]pyridin-5-ol (Compound 49)

From 5-(benzyloxy)-3H-imidazo[4,5-b]pyridine and 2,4-dichlorophenylboronic acid, prepared in a similar manner as the one described in Example 1.26, the title compound was obtained. LCMS m/z=279.9 [M+H]$^+$; $^1$H NMR (400 MHz, methanol-d$_4$) δ ppm 6.72 (d, J=8.7 Hz, 1H), 7.57 (dd, J$_1$=8.5 Hz, J$_2$=2.2 Hz, 1H), 7.63 (d, J=8.5 Hz, 1H), 7.79 (d, J=2.2 Hz, 1H), 7.99 (d, J=8.7 Hz, 1H), 8.34 (s, 1H).

Example 1.44

Preparation of 3-(3-Chloro-2-fluorophenyl)-3H-imidazo[4,5-b]pyridin-5-ol (Compound 50)

From 5-(benzyloxy)-3H-imidazo[4,5-b]pyridine and 3-chloro-2-fluorophenylboronic acid, prepared in a similar manner as the one described in Example 1.26, the title compound was obtained. LCMS m/z=263.9 [M+H]$^+$; $^1$H NMR (400 MHz, methanol-d$_4$) δ ppm 6.73 (d, J=8.7 Hz, 1H), 7.39 (td, J$_1$=8.2 Hz, J$_2$=1.5 Hz, 1H), 7.68 (m, 2H), 8.00 (d, J=8.7 Hz, 1H), 8.36 (s, 1H).

Example 1.45

Preparation of 3-(2-Fluoro-3-(trifluoromethyl)phenyl)-3H-imidazo[4,5-b]pyridin-5-ol (Compound 51)

From 5-(benzyloxy)-3H-imidazo[4,5-b]pyridine and 2-fluoro-3-(trifluoromethyl)phenylboronic acid, prepared in a similar manner as the one described in Example 1.26, the title compound was obtained. LCMS m/z=298.1 [M+H]$^+$.

Example 1.46

Preparation of 3-(2,3-Dichlorophenyl)-3H-imidazo[4,5-b]pyridin-5-ol (Compound 52)

From 5-(benzyloxy)-3H-imidazo[4,5-b]pyridine and 2,3-dichlorophenylboronic acid, prepared in a similar manner as the one described in Example 1.26, the title compound was obtained. LCMS m/z=280.0 [M+H]$^+$.

Example 1.47

Preparation of 3-(2-Fluoro-3-methylphenyl)-3H-imidazo[4,5-b]pyridin-5-ol (Compound 67)

From 5-(benzyloxy)-3H-imidazo[4,5-b]pyridine and 2-fluoro-3-methylphenylboronic acid, prepared in a similar manner as the one described in Example 1.26, the title compound was obtained. LCMS m/z=244.2 [M+H]$^+$.

Example 1.48

Preparation of 3-(2-(Trifluoromethoxy)phenyl)-3H-imidazo[4,5-b]pyridin-5-ol (Compound 107)

Step A: Preparation of 5-Nitro-6-(2-(trifluoromethoxy)phenylamino)pyridin-2-ol 2,6-Dichloro-3-nitropyridine (10.0 g, 51.8 mmol) and 2-(trifluoromethoxy)aniline (18.4 g, 104 mmol) were taken up in ethanol (50 mL) and heated to 100° C. for 48 h in a sealed tube. The reaction mixture was cooled in an ice bath, and the resulting precipitate was collected by vacuum filtration to give an intermediate 6-chloro-3-nitro-N-(2-(trifluoromethoxy)phenyl)pyridin-2-amine, which was dissolved in dioxane (65 mL) and H$_2$O (35 mL). Potassium hydroxide (2.90 g, 51.7 mmol) was added and the reaction mixture was heated to 100° C. for 16 h. After cooling, the pH was adjusted to less than 7 with 1 N HCl. The resulting precipitate was collected by vacuum filtration to give the title compound as a bright yellow solid (5.10 g). LCMS m/z=316.0 [M+H]$^+$; $^1$H NMR (400 MHz, CDCl$_3$) δ ppm 5.91 (d, J=10.1 Hz, 1H), 7.51 (m, 4H), 8.26 (d, J=10.1 Hz, 1H), 8.50-8.85 (broad s, 1H), 10.78 (broad s, 1H).

Step B: Preparation of 5-Amino-6-(2-(trifluoromethoxy)phenylamino)pyridin-2-ol

5-Nitro-6-(2-(trifluoromethoxy)phenylamino)pyridin-2-ol (400 mg, 1.27 mmol) and methanol (370 mL) were stirred at 25° C. for 4 h with excess Raney nickel under an atmosphere of hydrogen. After 4 h the solution was filtered by vacuum filtration through celite. The filtrate was concentrated under reduced pressure to give the title compound as a dark green solid (300 mg). LCMS m/z=286.2 [M+H]$^+$.

Step C: Preparation of 3-(2-(Trifluoromethoxy)phenyl)-3H-imidazo[4,5-b]pyridin-5-ol (Compound 107)

To a solution of 5-amino-6-(2-(trifluoromethoxy)phenylamino)pyridin-2-ol (75.0 mg, 0.26 mmol) dissolved in MeOH was added trimethyl orthoformate (1.0 mL, 9.05 mmol) and catalytical amount of trifluoroacetic acid. The solution was stirred at room temperature overnight and concentrated under reduced pressure. The residue was purified by preparative HPLC to give the title compound (78 mg). LCMS m/z=296.0 [M+H]$^+$, $^1$H NMR (400 MHz, DMSO-d$_6$) δ ppm 6.63 (d, J=8.6 Hz, 1H), 7.66 (m, 3H), 7.81 (d, J=7.6 Hz, 1H), 8.03 (d, J=8.6 Hz, 1H), 8.42 (s, 1H), 10.60-11.20 (broad s, 1H).

Example 1.49

Preparation of 2-Methyl-3-(2-(trifluoromethoxy)phenyl)-3H-imidazo[4,5-b]pyridin-5-ol (Compound 108)

From 5-amino-6-(2-(trifluoromethoxy)phenylamino)pyridin-2-ol, prepared in a similar manner as the one described in Example 1.9, the title compound was obtained. LCMS m/z=310.0 [M+H]$^+$.

Example 1.50

Preparation of 2-Amino-3-(2-(trifluoromethoxy)phenyl)-3H-imidazo[4,5-b]pyridin-5-ol (Compound 109)

From 5-amino-6-(2-(trifluoromethoxy)phenylamino)pyridin-2-ol, prepared in a similar manner as the one described in Example 1.8, the title compound was obtained. LCMS m/z=311.2 [M+H]$^+$.

Example 1.51

Preparation of 2-Chloro-3-(2-(trifluoromethoxy)phenyl)-3H-imidazo[4,5-b]pyridin-5-ol (Compound 125)

Step A: Preparation of 5-Nitro-6-(2-(trifluoromethoxy)phenylamino)pyridin-2-yl methanesulfonate 5-Nitro-6-(2-(trifluoromethoxy)phenylamino)pyridin-2-ol (1.5 g, 4.8 mmol) was taken up in $CH_2Cl_2$ (25 mL). TEA (1.3 ml, 9.5 mmol) was added followed by mesylchloride (0.45 ml, 5.7 mmol). The reaction mixture was stirred at ambient temperature for 1 hour and quenched with 1 N HCl. The layers were separated and the aqueous layer was back extracted with additional $CH_2Cl_2$. The combined organic portions were dried over $Na_2SO_4$ and concentrated under reduced pressure to give the title compound (1.8 g). $^1H$ NMR (400 MHz, $CDCl_3$) δ ppm 3.26 (s, 3H), 6.54 (d, J=8.8 Hz, 1H), 7.26 (m, 1H), 7.39 (m, 2H), 8.22 (m, 1H), 8.67 (d, J=8.8, 1H), 10.46 (s, 1H).

Step B: Preparation of 2-Hydroxy-3-(2-(trifluoromethoxy)phenyl)-3H-imidazo[4,5-b]pyridin-5-yl methanesulfonate 5-Nitro-6-(2-(trifluoromethoxy)phenylamino)pyridin-2-yl methanesulfonate (1.8 g, 4.58 mmol) was dissolved in MeOH (45 mL) and catalytic amount of 10% Pd/C was added. The reaction flask was purged with nitrogen and placed under an atmosphere of hydrogen for 2 h. The reaction mixture was filtered through Celite® and the solvent was removed under reduced pressure. The residue was immediately dissolved in THF (35 mL) and CDI (1.8 g, 11.0 mmol) added. The mixture was stirred overnight and concentrated under reduced pressure. The residue was added EtOAc, washed with water and 1 M HCl, dried over $MgSO_4$ and concentrated under reduced pressure. The residue was purified by silica gel column chromatography to give the title compound (1.1 g). LCMS m/z=390.3 $[M+H]^+$.

Step C: Preparation of 2-Chloro-3-(2-(trifluoromethoxy)phenyl)-3H-imidazo[4,5-b]pyridin-5-ol (Compound 125)

2-Hydroxy-3-(2-(trifluoromethoxy)phenyl)-3H-imidazo[4,5-b]pyridin-5-yl methanesulfonate (0.50 g, 1.3 mmol) taken up in phosphoryl trichloride (3.0 mL) was heated in a sealed tube to 80° C. for 48 h. The mixture was concentrated under reduced pressure and $NaHCO_3$ was added to the residue until it turned basic. The solution was further diluted with water and extracted with EtOAc (3×). The combined organic extracts were dried over $MgSO_4$ and concentrated under reduced pressure. The residue was purified column chromatography to give 2-chloro-3-(2-(trifluoromethoxy)phenyl)-3H-imidazo[4,5-b]pyridin-5-yl methanesulfonate, which was dissolved in a 1:4:1 solution of 1 M LiOH/THF/MeOH (10 mL) and stirred at room temperature for 1 hour. The mixture was concentrated under reduced pressure and the remaining was acidified with 1 N HCl. The resulting precipitate was collected by vacuum filtration and purified via preparative HPLC to give the title compound (0.11 g, 0.32 mmol, 25%). LCMS m/z=330.2 $[M+H]^+$, $^1H$ NMR (400 MHz, methanol-$d_4$) δ ppm 6.70 (d, J=8.7 Hz, 1H), 7.58-7.68 (m, 3H), 7.73 (m, 1H), 7.90 (d, J=8.7 Hz, 1H).

Example 1.52

Preparation of 2-Cyclopropyl-3-(2-(trifluoromethoxy)phenyl)-3H-imidazo[4,5-b]pyridin-5-ol (Compound 124)

5-Amino-6-(2-(trifluoromethoxy)phenylamino)pyridin-2-ol (0.10 g, 0.32 mmol) was dissolved in nitrobenzene (0.5 mL). Cyclopropanecarbaldehyde (0.044 g, 0.64 mmol) was added. The reaction mixture was heated to 120° C. overnight. After cooling, hexanes was added to the reaction mixture to form a precipitate. The precipitate was collected, washed with hexanes, and purified via HPLC to give the title compound (11 mg). LCMS m/z=336.2 $[M+H]^+$; $^1H$ NMR (400 MHz, methanol-$d_4$) δ ppm 1.35 (m, 4H), 2.03 (m, 1H), 6.86 (d, J=8.8 Hz, 1H), 7.71 (m, 2H), 7.83 (m, 2H), 7.83 (d, J=8.8 Hz, 1H).

Example 1.53

Preparation of 3-(2,3-Difluorophenyl)-3H-imidazo[4,5-b]pyridin-5-ol (Compound 59)

Step A: Preparation of 6-(2,3-Difluorophenylamino)-5-nitropyridin-2-ol 2,6-Dichloro-3-nitropyridine (2.0 g, 10.4 mmol) and 2,3-difluoroaniline (2.5 g, 20.7 mmol) were taken up in ethanol (10.0 mL) and heated to 120° C. for 18 hours in a sealed tube. The solution was cooled in an ice bath, and the resulting precipitate was collected by vacuum filtration. The solid intermediate was dissolved in dioxane (12 mL) and 2 M aqueous potassium hydroxide solution (6.0 mL, 12.0 mmol) was added. The reaction mixture was heated to 80° C. for 18 h. After cooling to ambient temperature the mixture was diluted with EtOAc and $H_2O$. The organic phase was discarded and the aqueous phase was acidified with 1 N HCl and extracted with EtOAc (2×). The organics were washed with brine, dried over $MgSO_4$, filtered, and concentrated to give the title compound (743 mg). $^1H$ NMR (400 MHz, $CDCl_3$) δ ppm 6.52 (d, J=9.2 Hz, 1H), 6.80 (m, 1H), 6.97 (q, J=8.2 Hz, 1H), 7.06 (d, J=8.1 Hz, 1H), 8.22 (d, J=9.2 Hz, 1H), 10.09 (s, 1H).

Step B: Preparation of 5-Amino-6-(2,3-difluorophenylamino)pyridin-2-ol

From 6-(2,3-difluorophenylamino)-5-nitropyridin-2-ol, prepared in a similar manner as the one described in Example 1.48, Step B, the title compound was obtained as a dark green solid. LCMS m/z=238.1 $[M+H]^+$.

Step C: Preparation of 3-(2,3-Difluorophenyl)-3H-imidazo[4,5-b]pyridin-5-ol (Compound 59)

From 5-amino-6-(2,3-difluorophenylamino)pyridin-2-ol, prepared in a similar manner as the one described in Example 1.48, Step C, the title compound was obtained. LCMS m/z=248.0 $[M+H]^+$.

Example 1.54

Preparation of 2-Amino-3-(2,3-difluorophenyl)-3H-imidazo[4,5-b]pyridin-5-ol (Compound 63)

From 5-amino-6-(2,3-difluorophenylamino)pyridin-2-ol, prepared in a similar manner as the one described in Example 1.8, the title compound was obtained. LCMS m/z=263.0 $[M+H]^+$.

Example 1.55

Preparation of 3-(3-Fluoro-2-methylphenyl)-3H-imidazo[4,5-b]pyridin-5-ol (Compound 60)

Step A: Preparation of 6-(3-Fluoro-2-methylphenylamino)-5-nitropyridin-2-ol

From 2,6-dichloro-3-nitropyridine and 3-fluoro-2-methylaniline, prepared in a similar manner as the one described in Example 1.53, Step A, the title compound was obtained.

Step B: Preparation of 5-Amino-6-(3-Fluoro-2-methylphenylamino)pyridin-2-ol

From 6-(3-fluoro-2-methylphenylamino)-5-nitropyridin-2-ol, prepared in a similar manner as the one described in Example 1.48, Step B, the title compound was obtained as a dark green solid.

Step C: Preparation of 3-(3-Fluoro-2-methylphenyl)-3H-imidazo[4,5-b]pyridin-5-ol (Compound 60)

From 5-amino-6-(3-fluoro-2-methylphenylamino)pyridin-2-ol, prepared in a similar manner as the one described in Example 1.48, Step C, the title compound was obtained. LCMS m/z=244.0 [M+H]$^+$.

Example 1.56

Preparation of 2-Amino-3-(3-Fluoro-2-methylphenyl)-3H-imidazo[4,5-b]pyridin-5-ol (Compound 64)

From 5-amino-6-(3-fluoro-2-methylphenylamino)pyridin-2-ol, prepared in a similar manner as the one described in Example 1.8, the title compound was obtained. LCMS m/z=259.0 [M+H]$^+$.

Example 1.57

Preparation of 3-(3-Chloro-2-methylphenyl)-3H-imidazo[4,5-b]pyridin-5-ol (Compound 61)

Step A: Preparation of 6-(3-Chloro-2-methylphenylamino)-5-nitropyridin-2-ol

From 2,6-dichloro-3-nitropyridine and 3-chloro-2-methylaniline, prepared in a similar manner as the one described in Example 1.53, Step A, the title compound was obtained.

Step B: Preparation of 5-Amino-6-(3-Chloro-2-methylphenylamino)pyridin-2-ol

From 6-(3-fluoro-2-methylphenylamino)-5-nitropyridin-2-ol, prepared in a similar manner as the one described in Example 1.48, Step B, the title compound was obtained as a dark green solid.

Step C: Preparation of 3-(3-Chloro-2-methylphenyl)-3H-imidazo[4,5-b]pyridin-5-ol (Compound 61)

From 5-amino-6-(3-chloro-2-methylphenylamino)pyridin-2-ol, prepared in a similar manner as the one described in Example 1.48, Step C, the title compound was obtained. LCMS m/z=260.1 [M+H]$^+$.

Example 1.58

Preparation of 2-Amino-3-(3-Chloro-2-methylphenyl)-3H-imidazo[4,5-b]pyridin-5-ol (Compound 65)

From 5-amino-6-(3-fluoro-2-methylphenylamino)pyridin-2-ol, prepared in a similar manner as the one described in Example 1.8, the title compound was obtained. LCMS m/z=275.1 [M+H]$^+$.

Example 1.59

Preparation of 3-(2-Chloro-3-fluorophenyl)-3H-imidazo[4,5-b]pyridin-5-ol (Compound 62)

Step A: Preparation of 6-(2-Chloro-3-fluorophenylamino)-5-nitropyridin-2-ol

From 2,6-dichloro-3-nitropyridine and 2-chloro-3-fluoroaniline, prepared in a similar manner as the one described in Example 1.53, Step A, the title compound was obtained.

Step B: Preparation of 5-Amino-6-(2-Chloro-3-fluorophenylamino)pyridin-2-ol

From 6-(2-chloro-3-fluorophenylamino)-5-nitropyridin-2-ol, prepared in a similar manner as the one described in Example 1.48, Step B, the title compound was obtained as a dark green solid.

Step C: Preparation of 3-(2-Chloro-3-fluorophenyl)-3H-imidazo[4,5-b]pyridin-5-ol (Compound 62)

From 5-amino-6-(2-chloro-3-fluorophenylamino)pyridin-2-ol, prepared in a similar manner as the one described in Example 1.48, Step C, the title compound was obtained. LCMS m/z=264.0 [M+H]$^+$.

Example 1.60

Preparation of 2-Amino-3-(2-Chloro-3-fluorophenyl)-3H-imidazo[4,5-b]pyridin-5-ol (Compound 66)

From 5-amino-6-(2-chloro-3-fluorophenylamino)pyridin-2-ol, prepared in a similar manner as the one described in Example 1.8, the title compound was obtained. LCMS m/z=279.0 [M+H]$^+$.

Example 1.61

Preparation of 3-(2,3-Dimethylphenyl)-3H-imidazo[4,5-b]pyridin-5-ol (Compound 78)

Step A: Preparation of 6-(2,3-Dimethylphenylamino)-5-nitropyridin-2-ol

From 2,6-dichloro-3-nitropyridine and 2,3-dimethylaniline, prepared in a similar manner as the one described in Example 1.53, Step A, the title compound was obtained. LCMS m/z=260.3 [M+H]$^+$.

Step B: Preparation of 5-Amino-6-(2,3-Dimethylphenylamino)pyridin-2-ol

From 6-(2,3-dimethylphenylamino)-5-nitropyridin-2-ol, prepared in a similar manner as the one described in Example

Step C: Preparation of 3-(2,3-Dimethylphenyl)-3H-imidazo[4,5-b]pyridin-5-ol (Compound 78)

From 5-amino-6-(2,3-dimethylphenylamino)pyridin-2-ol, prepared in a similar manner as the one described in Example 1.48, Step C, the title compound was obtained. LCMS m/z=239.9[M+H]$^+$.

Example 1.62

Preparation of 3-(2,3-Dimethylphenyl)-2-methyl-3H-imidazo[4,5-b]pyridin-5-ol (Compound 77)

From 5-amino-6-(2,3-dimethylphenylamino)pyridin-2-ol, prepared in a similar manner as the one described in Example 1.9, the title compound was obtained. LCMS m/z=254.1 [M+H]$^+$.

Example 1.63

Preparation of 3-(2-Bromo-3-methylphenyl)-3H-imidazo[4,5-b]pyridin-5-ol (Compound 80)

Step A: Preparation of 6-(2-Bromo-3-methylphenylamino)-5-nitropyridin-2-ol

From 2,6-dichloro-3-nitropyridine and 2-bromo-3-methylaniline, prepared in a similar manner as the one described in Example 1.53, Step A, the title compound was obtained. LCMS m/z=324.1 [M+H]$^+$.

Step B: Preparation of 5-Amino-6-(2-Bromo-3-methylphenylamino)pyridin-2-ol

From 6-(2-bromo-3-methylphenylamino)-5-nitropyridin-2-ol, prepared in a similar manner as the one described in Example 1.48, Step B, the title compound was obtained as a dark green solid. LCMS m/z=294.1 [M+H]$^+$.

Step C: Preparation of 3-(2-Bromo-3-methylphenyl)-3H-imidazo[4,5-b]pyridin-5-ol (Compound 80)

From 5-amino-6-(2-bromo-3-methylphenylamino)pyridin-2-ol, prepared in a similar manner as the one described in Example 1.48, Step C, the title compound was obtained. LCMS m/z=304.1 [M+H]$^+$.

Example 1.64

Preparation of 3-(2-Bromo-3-methylphenyl)-2-methyl-3H-imidazo[4,5-b]pyridin-5-ol (Compound 79)

From 5-amino-6-(2-bromo-3-methylphenylamino)pyridin-2-ol, prepared in a similar manner as the one described in Example 1.9, the title compound was obtained. LCMS m/z=318.0 [M+H]$^+$.

Example 1.65

Preparation of 3-(2,4,5-Trichlorophenyl)-3H-imidazo[4,5-b]pyridin-5-ol (Compound 74)

Step A: Preparation of 5-Nitro-6-(2,4,5-Trichlorophenylamino)pyridin-2-ol

From 2,6-dichloro-3-nitropyridine and 2,4,5-trichloroaniline, prepared in a similar manner as the one described in Example 1.53, Step A, the title compound was obtained. LCMS m/z=334.0 [M+H]$^+$.

Step B: Preparation of 5-Amino-6-(2,4,5-Trichlorophenylamino)pyridin-2-ol

From 5-nitro-6-(2,4,5-trichlorophenylamino)pyridin-2-ol, prepared in a similar manner as the one described in Example 1.48, Step B, the title compound was obtained as a dark green solid.

Step C: Preparation of 3-(2,4,5-Trichlorophenyl)-3H-imidazo[4,5-b]pyridin-5-ol (Compound 74)

From 5-amino-6-(2,4,5-trichlorophenylamino)pyridin-2-ol, prepared in a similar manner as the one described in Example 1.48, Step C, the title compound was obtained. LCMS m/z=314.0 [M+H]$^+$.

Example 1.66

Preparation of 2-Amino-3-(2,4,5-Trichlorophenyl)-3H-imidazo[4,5-b]pyridin-5-ol (Compound 72)

From 5-amino-6-(2,4,5-trichlorophenylamino)pyridin-2-ol, prepared in a similar manner as the one described in Example 1.8, the title compound was obtained. LCMS m/z=329.0 [M+H]$^+$.

Example 1.67

Preparation of 2-Methyl-3-(2,4,5-Trichlorophenyl)-3H-imidazo[4,5-b]pyridin-5-ol (Compound 73)

From 5-amino-6-(2,4,5-trichlorophenylamino)pyridin-2-ol, prepared in a similar manner as the one described in Example 1.9, the title compound was obtained. LCMS m/z=327.9 [M+H]$^+$.

Example 1.68

Preparation of 2-Amino-3-(2,3,4-Trichlorophenyl)-3H-imidazo[4,5-b]pyridin-5-ol (Compound 83)

From 5-amino-6-(2,3,4-trichlorophenylamino)pyridin-2-ol, prepared in a similar manner as the one described in Example 1.8, the title compound was obtained. LCMS m/z=328.0 [M+H]$^+$.

Example 1.69

Preparation of 2-Methyl-3-(2,3,4-Trichlorophenyl)-3H-imidazo[4,5-b]pyridin-5-ol (Compound 82)

From 5-amino-6-(2,3,4-trichlorophenylamino)pyridin-2-ol, prepared in a similar manner as the one described in Example 1.9, the title compound was obtained. LCMS m/z=328.1 [M+H]$^+$.

Example 1.70

Preparation of 3-(4-Chloronaphthalen-1-yl)-3H-imidazo[4,5-b]pyridin-5-ol (Compound 76)

Step A: Preparation of 5-Amino-6-(4-Chloronaphthalen-1-ylamino)pyridin-2-ol

From 2,6-dichloro-3-nitropyridine and 4-chloronaphthalen-1-amine, prepared in a similar manner as the one described in Example 1.48, Steps A and B, the title compound was obtained. LCMS m/z=286.0 [M+H]$^+$.

Step B: Preparation of 3-(4-Chloronaphthalen-1-yl)-3H-imidazo[4,5-b]pyridin-5-ol (Compound 76)

From 5-amino-6-(4-chloronaphthalen-1-ylamino)pyridin-2-ol, prepared in a similar manner as the one described in Example 1.48, Step C, the title compound was obtained. LCMS m/z=296.0 [M+H]$^+$.

Example 1.71

Preparation of 2-Amino-3-(4-Chloronaphthalen-1-yl)-3H-imidazo[4,5-b]pyridin-5-ol (Compound 87)

From 5-amino-6-(4-chloronaphthalen-1-ylamino)pyridin-2-ol, prepared in a similar manner as the one described in Example 1.8, the title compound was obtained. LCMS m/z=311.2 [M+H]$^+$.

Example 1.72

Preparation of 3-(4-Chloronaphthalen-1-yl)-2-methyl-3H-imidazo[4,5-b]pyridin-5-ol (Compound 75)

From 5-amino-6-(4-chloronaphthalen-1-ylamino)pyridin-2-ol, prepared in a similar manner as the one described in Example 1.9, the title compound was obtained. LCMS m/z=310.1 [M+H]$^+$.

Example 1.73

Preparation of 3-(Naphthalen-1-yl)-3H-imidazo[4,5-b]pyridin-5-ol (Compound 85)

Step A: Preparation of 5-Amino-6-(Naphthalen-1-ylamino)pyridin-2-ol

From 2,6-dichloro-3-nitropyridine and naphthalen-1-amine, prepared in a similar manner as the one described in Example 1.48, Steps A and B, the title compound was obtained. LCMS m/z=252.2 [M+H]$^+$.

Step B: Preparation of 3-(Naphthalen-1-yl)-3H-imidazo[4,5-b]pyridin-5-ol (Compound 85)

From 5-amino-6-(naphthalen-1-ylamino)pyridin-2-ol, prepared in a similar manner as the one described in Example 1.48, Step C, the title compound was obtained. LCMS m/z=262.1 [M+H]$^+$.

Example 1.74

Preparation of 2-Amino-3-(Naphthalen-1-yl)-3H-imidazo[4,5-b]pyridin-5-ol (Compound 86)

From 5-amino-6-(naphthalen-1-ylamino)pyridin-2-ol, prepared in a similar manner as the one described in Example 1.8, the title compound was obtained. LCMS m/z=277.2 [M+H]$^+$.

Example 1.75

Preparation of 2-Methyl-3-(Naphthalen-1-yl)-3H-imidazo[4,5-b]pyridin-5-ol (Compound 81)

From 5-amino-6-(naphthalen-1-ylamino)pyridin-2-ol, prepared in a similar manner as the one described in Example 1.9, the title compound was obtained. LCMS m/z=276.1 [M+H]$^+$.

Example 1.76

Preparation of 3-(2-Methylnaphthalen-1-yl)-3H-imidazo[4,5-b]pyridin-5-ol (Compound 84)

Step A: Preparation of 5-Amino-6-(2-methylnaphthalen-1-ylamino)pyridin-2-ol

From 2,6-dichloro-3-nitropyridine and 2-methylnaphthalen-1-amine, prepared in a similar manner as the one described in Example 1.48, Steps A and B, the title compound was obtained. LCMS m/z=266.2 [M+H]$^+$.

Step B: Preparation of 3-(2-Methylnaphthalen-1-yl)-3H-imidazo[4,5-b]pyridin-5-ol (Compound 84)

From 5-amino-6-(2-methylnaphthalen-1-ylamino)pyridin-2-ol, prepared in a similar manner as the one described in Example 1.48, Step C, the title compound was obtained. LCMS m/z=276.2 [M+H]$^+$.

Example 1.77

Preparation of 2-Amino-3-(2-Methylnaphthalen-1-yl)-3H-imidazo[4,5-b]pyridin-5-ol (Compound 88)

From 5-amino-6-(2-methylnaphthalen-1-ylamino)pyridin-2-ol, prepared in a similar manner as the one described in Example 1.8, the title compound was obtained. LCMS m/z=291.1 [M+H]$^+$.

Example 1.78

Preparation of 2-Methyl-3-(2-Methylnaphthalen-1-yl)-3H-imidazo[4,5-b]pyridin-5-ol (Compound 89)

From 5-amino-6-(2-methylnaphthalen-1-ylamino)pyridin-2-ol, prepared in a similar manner as the one described in Example 1.9, the title compound was obtained. LCMS m/z=290.1 [M+H]$^+$; $^1$H NMR (400 MHz, DMSO-$d_6$) δ ppm 2.12 (s, 3H), 2.24 (s, 3H), 6.64 (d, J=8.6 Hz, 1H), 7.01 (d, J=8.3 Hz, 1H), 7.49 (m, 1H), 7.58 (m, 1H), 7.66 (d, J=8.5 Hz, 1H), 8.06 (d, J=8.6 Hz, 1H), 8.10 (d, J=8.0 Hz, 1H), 8.14 (d, J=8.5 Hz, 1H) 10.95 (broad s, 1H).

Example 1.79

Preparation of 3-(2,3-Dihydro-1H-inden-4-yl)-3H-imidazo[4,5-b]pyridin-5-ol (Compound 99)

Step A: Preparation of 5-Amino-6-(2,3-Dihydro-1H-inden-4-ylamino)pyridin-2-ol

From 2,6-dichloro-3-nitropyridine and 2,3-dihydro-1H-inden-4-amine, prepared in a similar manner as the one described in Example 1.48, Steps A and B, the title compound was obtained. LCMS m/z=242.2 [M+H]+.

Step B: Preparation of 3-(2,3-Dihydro-1H-inden-4-yl)-3H-imidazo[4,5-b]pyridin-5-ol (Compound 99)

From 5-amino-6-(2,3-dihydro-1H-inden-4-ylamino)pyridin-2-ol, prepared in a similar manner as the one described in Example 1.48, Step C, the title compound was obtained. LCMS m/z=252.1 [M+H]+.

Example 1.80

Preparation of 2-Amino-3-(2,3-Dihydro-1H-inden-4-yl)-3H-imidazo[4,5-b]pyridin-5-ol (Compound 100)

From 5-amino-6-(2,3-dihydro-1H-inden-4-ylamino)pyridin-2-ol, prepared in a similar manner as the one described in Example 1.8, the title compound was obtained. LCMS m/z=267.0 [M+H]+.

Example 1.81

Preparation of 2-Amino-3-(2-Fluorophenyl)-3H-imidazo[4,5-b]pyridin-5-ol (Compound 58)

Step A: Preparation of 6-(2-Fluorophenylamino)-5-nitropyridin-2-ol

From 2,6-dichloro-3-nitropyridine and 2-fluoroaniline, prepared in a similar manner as the one described in Example 1.53, Step A, the title compound was obtained. $^1$H NMR (400 MHz, CDCl$_3$) δ ppm 6.85 (dd, J$_1$=8.6, J$_2$=1.0 Hz, 1H), 7.11-7.24 (m, 3H), 8.32 (t, J=7.8 Hz, 1H), 8.49 (dd, J$_1$=8.6, J$_2$=1.0 Hz, 1H), 10.40 (broad s, 1H).

Step B: Preparation of 2-Amino-3-(2-Fluorophenyl)-3H-imidazo[4,5-b]pyridin-5-ol (Compound 58)

6-(2-Fluorophenylamino)-5-nitropyridin-2-ol, was reduced and cyclized to the title compound as described in Example 1.48, Step B and Example 1.8 respectively. LCMS m/z=245.3[M+H]+; $^1$H NMR (400 MHz, methanol-d$_4$) δ ppm 6.65 (d, J=8.5 Hz, 1H), 7.48 (m, 2H), 7.64-7.75 (m, 3H).

Example 1.82

Preparation of 3-(2-Fluorophenyl)-2-methyl-3H-imidazo[4,5-b]pyridin-5-ol (Compound 117)

From 5-amino-6-(2-fluorophenylamino)pyridin-2-ol, prepared in a similar manner as the one described in Example 1.9, the title compound was obtained. LCMS m/z=244.0 [M+H]+.

Example 1.83

Preparation of 2-Methyl-3-(2-(Methylthio)phenyl)-3H-imidazo[4,5-b]pyridin-5-ol (Compound 110)

Step A: Preparation of 6-(2-(Methylthio)phenylamino)-5-nitropyridin-2-ol

From 2,6-dichloro-3-nitropyridine and 2-(methylthio) aniline, prepared in a similar manner as the one described in Example 1.48, Step A, the title compound was obtained. LCMS m/z=278.2 [M+H]+.

Step B: Preparation of 5-Amino-6-(2-(Methylthio)phenylamino)pyridin-2-ol

From 6-(2-(methylthio)phenylamino)-5-nitropyridin-2-ol, prepared in a similar manner as the one described in Example 1.48, Step B, the title compound was obtained. LCMS m/z=248.0 [M+H]+.

Step C: Preparation of 2-Methyl-3-(2-(Methylthio) phenyl)-3H-imidazo[4,5-b]pyridin-5-ol (Compound 110)

From 5-amino-6-(2-(methylthio)phenylamino)pyridin-2-ol, prepared in a similar manner as the one described in Example 1.9, the title compound was obtained. LCMS m/z=272.0 [M+H]+.

Example 1.84

Preparation of 3-(2-Chlorophenyl)-2-methyl-3H-imidazo[4,5-b]pyridin-5-ol (Compound 112)

From 5-amino-6-(2-chlorophenylamino)pyridin-2-ol), prepared in a similar manner as the one described in Example 1.9, the title compound was obtained. LCMS m/z=260.0 [M+H]+; $^1$H NMR (400 MHz, DMSO-d$_6$) δ ppm 2.25 (s, 3H), 6.51 (d, J=8.5 Hz, 1H), 7.61 (m, 2H), 7.68 (dd, J$_1$=7.0 Hz, J$_2$=2.1 Hz, 1H), 7.77 (dd, J$_1$=7.8 Hz, J$_2$=1.9 Hz, 1H), 7.87 (d, J=8.5 Hz, 1H), 10.69 (s, 1H).

Example 1.85

Preparation of 2-Amino-3-(2-Chlorophenyl)-3H-imidazo[4,5-b]pyridin-5-ol (Compound 113)

From 5-amino-6-(2-chlorophenylamino)pyridin-2-ol, prepared in a similar manner as the one described in Example 1.8, the title compound was obtained. LCMS m/z=261.0 (M+H+, $^{35}$Cl), 263.0 [M+H]+; $^1$H NMR (400 MHz, d6-DMSO) δ ppm 6.13 (broad s, 2H), 6.26 (d, J=8.2 Hz, 1H), 7.40 (d, J=8.2 Hz, 1H), 7.55 (m, 3H), 7.70 (d, J=7.0 Hz, 1H), 9.95 (s, 1H).

Example 1.86

Preparation of 3-(2-Cyclopropylphenyl)-3H-imidazo[4,5-b]pyridin-5-ol (Compound 106)

Step A: Preparation of 6-(2-Cyclopropylphenylamino)-5-nitropyridin-2-ol

From 2,6-Dichloro-3-nitropyridine and 2-cyclopropylaniline, prepared in a similar manner as the one described in Example 1.48, Step A, the title compound was obtained. LCMS m/z=272.3 [M+H]+.

Step B: Preparation of 5-Amino-6-(2-Cyclopropylphenylamino)pyridin-2-ol

From 6-(2-cyclopropylphenylamino)-5-nitropyridin-2-ol, prepared in a similar manner as the one described in Example 1.48, Step B, the title compound was obtained as a dark green solid. LCMS m/z=242.2 [M+H]$^+$.

Step C: Preparation of 3-(2-Cyclopropylphenyl)-3H-imidazo[4,5-b]pyridin-5-ol (Compound 106)

From 5-amino-6-(2-cyclopropylphenylamino)pyridin-2-ol, prepared in a similar manner as the one described in Example 1.48, Step C, the title compound was obtained. LCMS m/z=252.3 [M+H]$^+$.

Example 1.87

Preparation of 2-Chloro-3-(2-Cyclopropylphenyl)-3H-imidazo[4,5-b]pyridin-5-ol (Compound 133)

Step A: Preparation of 6-(2-Cyclopropylphenylamino)-5-nitropyridin-2-yl methanesulfonate From 6-(2-cyclopropylphenylamino)-5-nitropyridin-2-ol, prepared in a similar manner as the one described in Example 1.51, Step A, the title compound was obtained. LCMS m/z=350.4 [M+H]$^+$

Step B: Preparation of 3-(2-Cyclopropylphenyl)-2-hydroxy-3H-imidazo[4,5-b]pyridin-5-yl methanesulfonate From 6-(2-cyclopropylphenylamino)-5-nitropyridin-2-yl methanesulfonate, prepared in a similar manner as the one described in Example 1.51, Step B, the title compound was obtained (3.2 g). LCMS m/z=345.9 [M+H]$^+$; $^1$H NMR (400 MHz, methanol-d$_4$) δ ppm 0.53 (m, 1H), 0.62 (m, 1H), 0.73 (m, 2H), 1.72 (m, 1H), 3.31 (s, 3H), 6.94 (d, J=8.2 Hz, 1H), 7.34 (d, J=7.5 Hz, 1H), 7.37 (m, 2H), 7.44 (m, 1H), 7.46 (d, J=8.2 Hz, 1H).

Step C: Preparation of 2-Chloro-3-(2-cyclopropylphenyl)-3H-imidazo[4,5-b]pyridin-5-ol (Compound 133)

From 3-(2-cyclopropylphenyl)-2-hydroxy-3H-imidazo[4,5-b]pyridin-5-yl methanesulfonate, prepared in a similar manner as the one described in Example 1.51, step C, the title compound was obtained. LCMS m/z=286.0 [M+H]$^+$; $^1$H NMR (400 MHz, methanol-d$_4$) δ ppm 0.50-0.60 (m, 1H), 0.61-0.76 (m, 3H), 1.45 (m, 1H), 6.68 (d, J=8.6 Hz, 1H), 7.23 (d, J=7.7 Hz, 1H), 7.32 (dd, J$_1$=7.7, J$_2$=1.2 Hz, 1H), 7.39 (td, J$_1$=7.4 Hz, J$_2$=1.3 Hz, 1H), 7.51 (td, J$_1$=7.6 Hz, J$_2$=1.3 Hz, 1H), 7.89 (d, J=8.6 Hz, 1H).

Example 1.88

Preparation of 3-(2-(Trifluoromethylthio)phenyl)-3H-imidazo[4,5-b]pyridin-5-ol (Compound 121)

Step A: Preparation of 5-Nitro-6-(2-(Trifluoromethylthio)phenylamino)pyridin-2-ol From 2,6-dichloro-3-nitropyridine and 2-(trifluoromethylthio)aniline 2-(trifluoromethylthio)aniline, prepared in a similar manner as the one described in Example 1.48, Step A, the title compound was obtained. LCMS m/z=332.3 [M+H]$^+$.

Step B: Preparation of 5-Amino-6-(2-(Trifluoromethylthio)phenylamino)pyridin-2-ol From 5-nitro-6-(2-(trifluoromethylthio)phenylamino)pyridin-2-ol, prepared in a similar manner as the one described in Example 1.48, Step B, the title compound was obtained as dark green oil. LCMS m/z=302.0 [M+H]$^+$.

Step C: Preparation of 3-(2-(Trifluoromethylthio)phenyl)-3H-imidazo[4,5-b]pyridin-5-ol (Compound 121)

From 5-amino-6-(2-(trifluoromethylthio)phenylamino)pyridin-2-ol, prepared in a similar manner as the one described in Example 1.48, Step C, the title compound was obtained as a white solid. LCMS m/z=312.0 [M+H]$^+$.

Example 1.89

Preparation of 2-Amino-3-(2-(Trifluoromethylthio)phenyl)-3H-imidazo[4,5-b]pyridin-5-ol (Compound 123)

From 5-amino-6-(2-(trifluoromethylthio)phenylamino)pyridin-2-ol, prepared in a similar manner as the one described in Example 1.8, the title compound was obtained as a white solid. LCMS m/z=326.9 [M+H]$^+$.

Example 1.90

Preparation of 2-Methyl-3-(2-(Trifluoromethylthio)phenyl)-3H-imidazo[4,5-b]pyridin-5-ol (Compound 122)

From 5-amino-6-(2-(trifluoromethylthio)phenylamino)pyridin-2-ol, prepared in a similar manner as the one described in Example 1.9, the title compound was obtained. LCMS m/z=326.2 [M+H]$^+$.

Example 1.91

Preparation of 2-Chloro-3-(2-(Trifluoromethylthio)phenyl)-3H-imidazo[4,5-b]pyridin-5-ol (Compound 132)

From 5-nitro-6-(2-(trifluoromethylthio)phenylamino)pyridin-2-ol, prepared in a similar manner as the one described in Example 1.51, the title compound was obtained. LCMS m/z=346.2 [M+H]$^+$; $^1$H NMR (400 MHz, methanol-d$_4$) δ ppm 6.70 (d, J=8.7 Hz, 1H), 7.70 (dd, J$_1$=7.8, J$_2$=1.4 Hz, 1H), 7.75 (td, J$_1$=7.8 Hz, J$_2$=1.5 Hz, 1H), 7.85 (td, J$_1$=7.7 Hz, J$_2$=1.5 Hz, 1H), 7.92 (d, J=8.6 Hz, 1H), 8.04 (d, J=7.6 Hz, 1H).

Example 1.92

Preparation of 2-Chloro-3-(2-(Trifluoromethyl)phenyl)-3H-imidazo[4,5-b]pyridin-5-ol (Compound 131)

From 5-nitro-6-(2-(trifluoromethyl)phenylamino)pyridin-2-ol, prepared in a similar manner as the one described in Example 1.51, the title compound was obtained. LCMS m/z=314.1 [M+H]$^+$; (400 MHz, DMSO-d$_6$) δ ppm 6.61 (d, J=8.6 Hz, 1H), 7.82-7.91 (m, 2H), 7.97 (m, 1H), 7.98 (d, J=8.6 Hz, 1H), 8.05 (d, J=7.8 Hz, 1H), 11.09 (broad s, 1H).

Example 1.93

Preparation of 3-(Adamant-1-yl)-3H-imidazo[4,5-b]pyridin-5-ol (Compound 114)

Step A: Preparation of 5-Amino-6-(1-Adamantylamino)pyridin-2-ol

From 2,6-dichloro-3-nitropyridine and prepared in a similar manner as the one described in Example 1.48, Steps A and B, the title compound was obtained. LCMS m/z=260.3 [M+H]$^+$.

Step B: Preparation of 3-(Adamant-1-yl)-3H-imidazo[4,5-b]pyridin-5-ol (Compound 114)

From N-(1-adamantyl)-6-chloro-3-nitropyridin-2-amine, prepared in a similar manner as the one described in Example 1.48, step C, the title compound was obtained. LCMS m/z=270.1 [M+H]$^+$.

Example 1.94

Preparation of 3-(Adamant-1-yl)-2-amino-3H-imidazo[4,5-b]pyridin-5-ol (Compound 116)

From 5-amino-6-(1-adamantylamino)pyridin-2-ol, prepared in a similar manner as the one described in Example 1.8, the title compound was obtained. LCMS m/z=285.1 [M+H]$^+$.

Example 1.95

Preparation of 3-(Adamant-1-yl)-2-methyl-3H-imidazo[4,5-b]pyridin-5-ol (Compound 115)

From 5-amino-6-(1-adamantylamino)pyridin-2-ol, prepared in a similar manner as the one described in Example 1.9, the title compound was obtained. CMS m/z=284.4 [M+H]$^+$.

Example 1.96

Preparation of 3-(3-fluoro-2-(trifluoromethyl)phenyl)-3H imidazo[4,5-b]pyridin-5-ol (Compound 111)

Step A: Preparation of 5-(benzyloxy)-3-(3-fluoro-2-(trifluoromethyl)phenyl)-3H-imidazo[4,5-b]pyridine 5-(Benzyloxy)-3H-imidazo[4,5-b]pyridine (0.10 g, 0.44 mmol) and 1,3-difluoro-2-(trifluoromethyl)benzene (0.12 g, 0.67 mmol) were dissolved in DMF (1.0 mL) and Cs$_2$CO$_3$ (0.29 g, 0.89 mmol) was added. The reaction mixture was heated to 80° C. overnight. The solution was then diluted with ether and washed with water. The aqueous layer was back extracted with additional ether. The combined organic portions were washed with brine, dried over MgSO$_4$ and concentrated under reduced pressure to give the title compound.

Step B: Preparation of 3-(3-Fluoro-2-(trifluoromethyl)phenyl)-3H imidazo[4,5-b]pyridin-5-ol (Compound 111)

From 5-(benzyloxy)-3-(3-fluoro-2-(trifluoromethyl)phenyl)-3H-imidazo[4,5-b]pyridine, prepared in a similar manner as the one described in Example 1.2, the title compound was obtained. LCMS m/z=298.0 [M+H]$^+$.

Example 1.97

Preparation of 3-(3-Bromo-2-(trifluoromethyl)phenyl)-3H-imidazo[4,5-b]pyridin-5-ol (Compound 101)

From 5-(Benzyloxy)-3H-imidazo[4,5-b]pyridine and 1-bromo-3-fluoro-2-(trifluoromethyl)benzene, prepared in a similar manner as the one described in Example 1.96, the title compound was obtained. LCMS m/z=358.0 [M+H]$^+$.

Example 1.98

Preparation of 3-(2,2-difluorocycloheptyl)-3H-imidazo[4,5-b]pyridin-5-ol (Compound 118)

Step A: Preparation of 5-(Benzyloxy)-3-(2,2-difluorocycloheptyl)-3H-imidazo[4,5-b]pyridine 2-(5-(Benzyloxy)-3H-imidazo[4,5-b]pyridin-3-yl)cycloheptanone (0.15 g, 0.45 mmol), was taken up DCM (4.5 mL) and cooled to 0° C. DAST (0.21 mL, 1.4 mmol) was added and the mixture was allowed to warm to room temperature and then heated to 40° C. overnight. The reaction mixture was washed with water, dried over Na$_2$SO$_4$, and the solvent was removed under reduced pressure to give the title compound.

Step B: Preparation of 3-(2,2-Difluorocycloheptyl)-3H-imidazo[4,5-b]pyridin-5-ol (Compound 118)

5-(Benzyloxy)-3-(2,2-difluorocycloheptyl)-3H-imidazo[4,5-b]pyridine was dissolved in DCM and diluted with excess sulfuric acid. The resulting solution was stirred overnight at room temperature then acidified with the addition of 1 M aqueous hydrochloric acid. The solvent was removed from the organic layer and the residue was purified via preparative HPLC to give the title compound. LCMS m/z=267.9 [M+H]$^+$.

Example 1.99

Preparation of 2-Amino-3-(4-Ethylphenyl)-3H-imidazo[4,5-b]pyridin-5-ol (Compound 13)

Step A: Preparation of 6-Chloro-N-(4-ethylphenyl)-3-nitropyridin-2-amine

From 2,6-dichloro-3-nitropyridine and 4-ethylaniline, prepared in a similar manner as the one described in Example 1.21 with the exception that the reaction was performed at 65° C., the title compound was obtained.

Step B: Preparation of 6-(Benzyloxy)-N-(4-ethylphenyl)-3-nitropyridin-2-amine

To a solution of benzyl alcohol (1.32 g, 12.2 mmol) in THF (15 mL) at room temperature was added sodium hydride (60% dispersion in mineral oil, 488 mg, 12.2 mmol). The mixture was stirred at room temperature for 0.5 h at which time 6-chloro-N-(4-ethylphenyl)-3-nitropyridin-2-amine (1.21 g, 4.03 mmol) was added. The mixture was heated in a sealed tube overnight at 65° C. The reaction vessel was cooled to room temperature and the mixture was quenched with saturated NaHCO$_3$. The mixture was extracted with EtOAc and the organics were dried over MgSO$_4$, filtered, and concentrated. Purification by silica gel chromatography (2% EtOAc in hexanes gradient to 15% EtOAc in hexanes) gave the title compound (987 mg) as a yellow solid. NMR (400 MHz, CDCl$_3$) δ ppm 1.26 (t, J=7.6 Hz, 3H), 2.66 (q, J=7.6 Hz, 2H), 5.34 (s, 2H), 6.25 (d, J=9.1 Hz, 1H), 7.20 (d, J=8.4 Hz, 2H), 7.41-7.28 (m, 5H), 7.45 (d, J=8.4 Hz, 2H), 8.40 (d, J=9.1 Hz, 1H), 10.51 (broad s, 1H).

Step C: Preparation of 6-(Benzyloxy)-N$^2$-(4-ethylphenyl)pyridine-2,3-diamine

To a solution of 6-(benzyloxy)-N-(4-ethylphenyl)-3-nitropyridin-2-amine (987 mg, 2.82 mmol in AcOH (6.0 mL) was added zinc dust (737 mg, 11.2 mmol). The mixture was stirred overnight at room temperature, filtered through Celite®, and concentrated. The crude residue was dissolved in EtOAc and washed with saturated NaHCO$_3$. The organics were dried over MgSO$_4$, filtered, and concentrated to give the title compound as a dark brown oil (716 mg). $^1$H NMR (400 MHz, CDCl$_3$) δ ppm 1.23 (t, J=7.6 Hz, 3H), 2.62 (q, J=7.6 Hz, 2H), 2.95 (broad s, 2H), 5.32 (s, 2H), 6.20 (d, J=8.1 Hz, 1H), 6.65 (broad s, 1H), 7.05 (d, J=8.1 Hz, 1H), 7.11 (d, J=8.4 Hz, 2H), 7.28-7.41 (m, 8H).

Step D: Preparation of 2-Amino-3-(4-Ethylphenyl)-3H-imidazo[4,5-b]pyridin-5-ol (Compound 13)

To 6-(benzyloxy)-N$^2$-(4-ethylphenyl)pyridine-2,3-diamine (358 mg, 1.12 mmol) was added H$_2$O (3.0 mL) and cyanogen bromide (178 mg, 1.68 mmol). The mixture was stirred vigorously at room temperature overnight. Saturated NaHCO$_3$ was added and the mixture was extracted with EtOAc. After concentration in vacuo, the crude material was dissolved in MeOH (5 mL) and ammonium formate (353 mg, 5.6 mmol) was added. Pd/C (10% by wt., 100 mg) was added and the mixture was stirred in a sealed vial at 60° C. overnight. The reaction mixture was cooled to room temperature, filtered through celite, and concentrated. The residue was purified by preparative HPLC to give the title compound (14.4 mg) as a white solid. LCMS m/z=255.3, [M+H]$^+$; $^1$H NMR (400 MHz, DMSO-d$_6$) δ ppm 1.26 (t, J=7.6 Hz, 3H), 2.73 (q, J=7.6 Hz, 2H), 6.54 (d, J=8.5 Hz, 1H), 7.49 (d, J=8.5 Hz, 2H), 7.53 (d, J=8.5 Hz, 2H), 7.71 (d, J=8.5 Hz, 1H), 8.32 (broad s, 2H), 10.91 (broad s, 1H).

Example 1.100

Preparation of 2-Chloro-3-(2-Chlorophenyl)-3H-imidazo[4,5-b]pyridin-5-ol (Compound 69)

Step A: Preparation of 6-(Benzyloxy)-N-(2-chlorophenyl)-3-nitropyridin-2-amine

From 2,6-dichloro-3-nitropyridine and 2-chloroaniline, prepared in a similar manner as the one described in Example 1.99, Steps A and B, the title compound was obtained. $^1$H NMR (400 MHz, CDCl$_3$) δ ppm 5.37 (s, 2H), 6.34 (d, J=9.1 Hz, 1H), 7.12 (td, J$_1$=8.0, J$_2$=1.4 Hz, 1H), 7.24 (td, J$_2$=1.3 Hz, 1H), 7.35 (m, 5H), 7.49 (dd, J$_1$=8.0, J$_2$=1.4 Hz, 1H), 8.12 (dd, J$_1$=8.2, J$_2$=1.3 Hz, 1H), 8.47 (d, J=9.1 Hz, 1H), 10.84 (broad s, 1H).

Step B: Preparation of 5-(Benzyloxy)-3-(2-chlorophenyl)-1H-imidazo[4,5-b]pyridin-2(3H)-one To a solution of 6-(benzyloxy)-N-(2-chlorophenyl)-3-nitropyridin-2-amine (750 mg, 2.11 mmol) in MeOH (20 mL) was added Raney nickel (300 mg). The reaction mixture was stirred overnight under H$_2$ (1 atm), filtered through Celite® and concentrated. The residue was dissolved in DCM (40 mL) and CDI (410 mg, 2.53 mmol) was added. The mixture was stirred at room temperature for 4 h, washed with saturated NaHCO$_3$ and water, dried over MgSO$_4$ and concentrated to give the title compound (905 mg). LCMS m/z=352.3, [M+H]$^+$.

Step C: Preparation of 2-Chloro-3-(2-Chlorophenyl)-3H-imidazo[4,5-b]pyridin-5-ol (Compound 69)

5-(Benzyloxy)-3-(2-chlorophenyl)-1H-imidazo[4,5-b]pyridin-2(3H)-one (905 mg, 2.58 mmol) and POCl$_3$ (1965 µl, 21.08 mmol) was heated in microwave at 100° C. for 1 h. The mixture was concentrated. The residue was dissolved in EtOAc and saturated NaHCO$_3$. The organics were separated, washed with brine, dried over MgSO$_4$, filtered, and concentrated. The residue was dissolved in DCM (2.5 mL) and H$_2$SO$_4$ (6 drops) was added. The mixture was stirred vigorously for 15 minutes. DCM was removed by gentle heating. The residue was dissolved in MeOH and purified by preparative HPLC to give the title compound (5.0 mg). LCMS m/z=280.2, [M+H]$^+$; $^1$H NMR (400 MHz, DMSO-d$_6$) δ ppm 6.63 (d, J=8.6 Hz, 1H), 7.63 (dd, J$_1$=7.6, J$_2$=1.6 Hz, 1H), 7.66 (td, J$_1$=7.6, J$_2$=1.8 Hz, 1H), 7.79 (m, 2H), 7.98 (d, J=8.6 Hz, 1H), 11.10 (broad s, 1H).

Example 1.101

Preparation of 2-Amino-3-p-tolyl-3H-imidazo[4,5-b]pyridin-5-ol (Compound 14)

From 2,6-dichloro-3-nitropyridine and 4-methylaniline, prepared in a similar manner as the one described in Example 1.99, the title compound was obtained. LCMS m/z=241.3, [M+H]$^+$.

Example 1.102

Preparation of 3-(4-Ethylphenyl)-2-methyl-3H-imidazo[4,5-b]pyridin-5-ol (Compound 15)

6-(Benzyloxy)-N$^2$-(4-ethylphenyl)pyridine-2,3-diamine (358 mg, 1.12 mmol) was dissolved in THF (1.0 mL). Trimethyl orthoacetate (1.0 mL) was added followed by TFA (10 µL). The mixture was stirred at room temperature overnight and concentrated in vacuo. The benzyl group was then removed as described in Example 1.98, Step B to give the title compound as a white solid (55.3 mg). LCMS m/z=254.3 [M+H]$^+$.

Example 1.103

Preparation of 2-Methyl-3-p-tolyl-3H-imidazo[4,5-b]pyridin-5-ol (Compound 16)

From 6-(benzyloxy)-N$^2$-p-tolylpyridine-2,3-diamine, prepared in a similar manner as the one described in Example 1.102, the title compound was obtained. LCMS m/z=240.3 [M+H]$^+$; $^1$H NMR (400 MHz, DMSO-d$_6$) δ ppm 2.43 (s, 3H), 2.47 (s, 3H), 6.70 (d, J=8.6 Hz, 1H), 7.45 (m, 4H), 8.03 (d, J=8.6 Hz, 1H), 11.17 (broad s, 1H).

Example 1.104

Preparation of 3-(4-Bromophenyl)-2-methyl-3H-imidazo[4,5-b]pyridin-5-ol (Compound 22)

Step A: Preparation of 6-(benzyloxy)-N-(4-bromophenyl)-3-nitropyridin-2-amine From 2,6-dichloro-3-nitropyridine and 4-bromoaniline, prepared in a similar manner as the one described in Example 1.99, Steps A and B, the title compound was obtained as a yellow solid. $^1$H NMR (400 MHz, CDCl$_3$) δ ppm 5.36 (s, 2H), 6.33 (d, J=9.1 Hz, 1H), 7.30-7.44 (m, 9H), 8.45 (d, J=9.1 Hz, 1H), 10.51 (broad s, 1H).

Step B: Preparation of 6-(Benzyloxy)-N$^2$-(4-bromophenyl)pyridine-2,3-diamine From 6-(benzyloxy)-N-(4-bromophenyl)-3-nitropyridin-2-amine, prepared in a similar manner as the one described in Example 1.100, Step B, the title compound was obtained as a dark brown oil. $^1$H NMR (400 MHz, CDCl$_3$) δ ppm 2.92 (broad s, 2H), 5.31 (s, 2H), 6.26 (d, J=8.1 Hz, 1H), 6.76 (broad s, 1H), 7.09 (d, J=8.1 Hz, 1H), 7.30-7.45 (m, 9H).

Step C: Preparation of 3-(4-Bromophenyl)-2-methyl-3H-imidazo[4,5-b]pyridin-5-ol (Compound 22)

From 6-(benzyloxy)-N$^2$-(4-bromophenyl)pyridine-2,3-diamine, prepared in a similar manner as the one described in Example 1.102, the title compound was obtained. LCMS m/z=304.2 [M+H]$^+$.

Example 1.105

Preparation of 2-Amino-3-(4-Bromophenyl)-3H-imidazo[4,5-b]pyridin-5-ol (Compound 23)

To a suspension of 6-(benzyloxy)-N$^2$-(4-bromophenyl)pyridine-2,3-diamine (3.86 g, 10.4 mmol) in H$_2$O was added cyanogen bromide (1.44 g, 13.5 mmol) and TFA (200 μL). The reaction mixture was stirred at room temperature for 2.5 h, added 2 M aqueous Na$_2$CO$_3$ and extracted with DCM. The organic extract was dried over MgSO$_4$, filtered, and concentrated. The residue was purified by column chromatography to give 5-(benzyloxy)-3-(4-bromophenyl)-3H-imidazo[4,5-b]pyridin-2-amine intermediate. The benzyl group was removed in a similar manner as the one described in Example 1.102 to give the title compound. LCMS m/z=305.1 [M+H]$^+$; $^1$H NMR (400 MHz, DMSO-d$_6$) δ ppm 6.22 (broad s, 2H), 6.29 (d, J=8.2 Hz, 1H), 7.39-7.46 (m, 3H), 7.77 (m, 2H), 9.96 (s, 1H).

Example 1.106

Preparation of 2-Amino-3-o-tolyl-3H-imidazo[4,5-b]pyridin-5-ol (Compound 30)

From 2,6-dichloro-3-nitropyridine and o-toluidine, prepared in a similar manner as the one described in Example 1.99, the title compound was obtained. LCMS m/z=241.0 [M+H]$^+$; $^1$H NMR (400 MHz, CDCl$_3$) δ ppm 2.03 (s, 3H), 4.65-4.86 (broad s, 2H), 6.49 (d, J=8.4 Hz, 1H), 7.21 (m, 1H), 7.28 (m, 2H), 7.33 (m, 1H), 7.61 (d, J=8.4 Hz, 1H).

Example 1.107

Preparation of 3-(4-Bromo-2-methylphenyl)-3H-imidazo[4,5-b]pyridin-5-ol (Compound 37)

Step A: Preparation of 6-(4-Bromo-2-methylphenylamino)-5-nitropyridin-2-ol

From 2,6-dichloro-3-nitropyridine and 4-bromo-2-methylaniline, prepared in a similar manner as the one described in Example 1.48, Step A, the title compound was obtained. $^1$H NMR (400 MHz, CDCl$_3$) δ ppm 2.29 (s, 3H), 5.83 (d, J=10.1 Hz, 1H), 7.14 (d, J=8.4 Hz, 1H), 7.48 (dd, J$_1$=8.4, J$_2$=2.1 Hz, 1H), 7.57 (d, J=2.0 Hz, 1H), 8.30 (d, J=10.1 Hz, 1H), 10.60 (broad s, 1H).

Step B: Preparation of 3-(4-bromo-2-methylphenyl)-3H-imidazo[4,5-b]pyridin-5-ol (Compound 37)

To a solution of 6-(4-bromo-2-methylphenylamino)-5-nitropyridin-2-ol (4.50 g, 13.9 mmol) in MeOH (30 mL) was added Raney Ni (1.00 g). The mixture was stirred vigorously under H$_2$ atmosphere overnight at which time additional Raney nickel (500 mg) was added. After stirring for an additional 45 h under H$_2$ atmosphere, the mixture was filtered through Celite® and concentrated. The residue was dissolved in THF (20 mL) and trimethoxymethane (25 mL) and trifluoroacetic acid (100 μL) was added. The mixture was heated at 50° C. for 12 h followed by additional heating at 80° C. for 4 h. After cooling to room temperature, the solution was concentrated in vacuo. The residue was purified by HPLC to give the title compound as a white solid (442 mg). LCMS m/z=304.1 [M+H]$^+$; $^1$H NMR (400 MHz, CDCl$_3$) δ ppm 2.07 (s, 3H), 6.61 (d, J=8.6 Hz, 1H), 7.15 (d, J=8.3 Hz, 1H), 7.48 (dd, J$_1$=8.3, J$_2$=1.9 Hz, 1H), 7.55 (s, 1H), 7.82 (s, 1H), 8.04 (d, J=8.6 Hz, 1H).

Example 1.108

Preparation of 3-(4-Bromo-5-chloro-2-methylphenyl)-3H-imidazo[4,5-b]pyridin-5-ol (Compound 45)

From 2,6-dichloro-3-nitropyridine and 4-bromo-5-chloro-2-methylaniline, prepared in a similar manner as the one described in Example 1.107, the title compound was obtained. LCMS m/z=338.3 [M+H]$^+$; $^1$H NMR (400 MHz, CDCl$_3$) δ ppm 2.07 (s, 3H), 6.68 (d, J=8.8 Hz, 1H), 7.43 (s, 1H), 7.70 (s, 1H), 7.98 (s, 1H), 8.11 (d, J=8.8 Hz, 1H).

Example 1.109

Preparation of 3-(5-Chloro-2-methylphenyl)-3H-imidazo[4,5-b]pyridin-5-ol (Compound 46)

To a solution of 3-(4-bromo-5-chloro-2-methylphenyl)-3H-imidazo[4,5-b]pyridin-5-ol (320 mg, 0.95 mmol) in MeOH (8.0 mL) was added palladium hydroxide (20% on carbon, 65 mg). The mixture was placed in a Parr shaker under H$_2$ (30 psi) for 12 h, filtered through Celite® and concentrated. The residue was purified by preparative HPLC to give the title compound as a white solid. LCMS m/z=260.1, [M+H]$^+$.

Example 1.110

Preparation of 3-(2-Chlorophenyl)-2-cyclopropyl-3H-imidazo[4,5-b]pyridin-5-ol (Compound 120)

Step A: Preparation of 5-Amino-6-(2-Chlorophenylamino)pyridin-2-ol

From 6-(2-chlorophenylamino)-5-nitropyridin-2-ol, prepared in a similar manner as the one described in Example 1.48 Step B, the title compound was obtained. LCMS m/z=236.2 [M+H]$^+$.

Step B: Preparation of 5-Amino-6-(2-chlorophenylamino)pyridin-2-ol

From 5-amino-6-(2-chlorophenylamino)pyridin-2-ol, prepared in a similar manner as the one described in Example 1.52, the title compound was obtained. LCMS m/z=286.3 [M+H]$^+$; $^1$H NMR (400 MHz, DMSO-d$_6$) δ ppm 0.96 (m, 2H), 1.17 (m, 2H), 1.61 (m, 1H), 6.54 (d, J=8.6 Hz, 1H), 7.63 (m, 2H), 7.75 (dd, J$_1$=6.8, J$_2$=2.3 Hz, 1H), 7.80 (dd, J$_1$=7.1, J$_2$=2.1 Hz, 1H), 7.86 (d, J=8.6 Hz, 1H), 10.81 (broad s, 1H).

Example 1.111

Preparation of 3-Phenyl-3H-imidazo[4,5-b]pyridin-5-ol (Compound 1)

Step A: Preparation of 6-(Benzyloxy)-3-nitro-N-phenylpyridin-2-amine

From 2,6-dichloro-3-nitropyridine and aniline, prepared in a similar manner as the one described in Example 1.99, Steps A and B, the title compound was obtained as an orange solid. $^1$H NMR (400 MHz, CDCl$_3$) δ ppm 5.36 (s, 2H), 6.29 (d, J=9.1 Hz, 1H), 7.20 (m, 1H), 7.29-7.41 (m, 7H), 7.55 (m, 2H), 8.40 (d, J=9.1 Hz, 1H), 10.56 (broad s, 1H).

Step B: Preparation of 6-(Benzyloxy)-N$^2$-phenylpyridine-2,3-diamine

From 6-(benzyloxy)-3-nitro-N-phenylpyridin-2-amine, prepared in a similar manner as the one described in Example 1.99, Step C, the title compound was obtained as dark brown oil. LCMS m/z=292.2, [M+H]$^+$.

Step C: Preparation of 5-(Benzyloxy)-3-phenyl-3H-imidazo[4,5-b]pyridine 6-(Benzyloxy)-N$^2$-phenylpyridine-2,3-diamine (60 mg, 0.21 mmol) was dissolved in trimethyl orthformate (5.0 mL), and TFA (10 μL) was added. The mixture was stirred at room temperature overnight and concentrated in vacuo. The residue was purified by preparative HPLC to give the title compound as a red solid (58 mg). $^1$H NMR (500 MHz, CDCl$_3$) δ ppm 5.40 (s, 2H), 7.15 (d, J=9.0 Hz, 1H), 7.31-7.42 (m, 5H), 7.62-7.72 (m, 5H), 8.32 (d, J=9.0 Hz, 1H), 9.25 (s, 1H).

Step D: Preparation of 3-Phenyl-3H-imidazo[4,5-b]pyridin-5-ol (Compound 1)

From 5-(benzyloxy)-3-phenyl-3H-imidazo[4,5-b]pyridine, prepared in a similar manner as the one described in Example 1.11, Step B, the title compound was obtained as a white solid. $^1$H NMR (400 MHz, DMSO-d$_6$) δ ppm 6.64 (d, J=8.6 Hz, 1H), 7.45 (t, J=7.6 Hz, 1H), 7.59 (t, J=7.6 Hz, 2H), 7.88 (d, J=7.3 Hz, 2H), 8.02 (d, J=8.6 Hz, 1H), 8.57 (broad s, 1H), 10.8 (s, 1H).

Example 1.112

Preparation of 3-(3-Chlorophenyl)-3H-imidazo[4,5-b]pyridin-5-ol (Compound 2)

From 2,6-dichloro-3-nitropyridine and 3-chloroaniline, prepared in a similar manner as the one described in Example 1.111, the title compound was obtained as a white solid. $^1$H NMR (400 MHz, methanol-d$_4$) δ ppm 6.83 (d, J=8.9 Hz, 1H), 7.51 (d, J=7.8 Hz, 1H), 7.59 (t, J=8.1 Hz, 1H), 7.82 (d, J=7.8 Hz, 1H), 8.04 (d, 2H), 8.90 (s, 1H).

Example 1.113

Preparation of 3-(Benzo[d][1,3]dioxol-5-yl)-3H-imidazo[4,5-b]pyridin-5-ol (Compound 3)

From 2,6-dichloro-3-nitropyridine and 3,4-(methylenedioxy)aniline, prepared in a similar manner as the one described in Example 1.111, the title compound was obtained as a white solid. $^1$H NMR (400 MHz, DMSO-d$_6$) δ ppm 6.14 (s, 1H), 6.61 (d, J=8.6 Hz, 1H), 7.11 (d, J=8.3 Hz, 1H), 7.28 (dd, J$_1$=8.3 Hz, J$_2$=2.3 Hz, 1H), 7.46 (s, 1H), 7.99 (d, J=8.6 Hz, 1H), 8.43 (s, 1H), 10.86 (broad s, 1H).

Example 1.114

Preparation of 3-(4-Benzylphenyl)-3H-imidazo[4,5-b]pyridin-5-ol (Compound 4)

From 2,6-dichloro-3-nitropyridine and 4-benzylaniline, prepared in a similar manner as the one described in Example 1.111, the title compound was obtained. $^1$H NMR (400 MHz, DMSO-d$_6$) δ ppm 4.03 (m, 2H), 6.6 (d, 1H), 7.17-7.24 (m, 1H), 7.30 (m, 4H), 7.44 (m, 2H), 7.73 (m, 2H), 8.0 (d, J=8.6 Hz, 1H), 8.5 (s, 1H), 10.8 (s, 1H).

Example 1.115

Preparation of 3-(2,3-Dihydro-1H-inden-5-yl)-3H-imidazo[4,5-b]pyridin-5-ol (Compound 5)

Step A: Preparation of 6-(Benzyloxy)-N-(2,3-dihydro-1H-inden-5-yl)-3-nitropyridin-2-amine From 2,6-dichloro-3-nitropyridine (660 mg, 3.42 mmol) and 5-aminoindan, prepared in a similar manner as the one described in Example 1.99, Steps A and B, the title compound was obtained.

Step B: Preparation of 6-(Benzyloxy)-N$^2$-(2,3-dihydro-1H-inden-5-yl)pyridine-2,3-diamine From 6-(benzyloxy)-N-(2,3-dihydro-1H-inden-5-yl)-3-nitropyridin-2-amine, prepared in a similar manner as the one described in Example 1.99, Step C the title compound was obtained as purple solid (568 mg). LCMS m/z=332.4 [M+H]$^+$.

Step C: Preparation of 5-(Benzyloxy)-3-(2,3-dihydro-1H-inden-5-yl)-3H-imidazo[4,5-b]pyridine From 6-(benzyloxy)-N$^2$-(2,3-dihydro-1H-inden-5-yl)pyridine-2,3-diamine, prepared in a similar manner as the one described in Example 1.111, Step C the title compound was obtained (185 mg). $^1$H NMR (400 MHz, CDCl$_3$) δ ppm 2.18 (quintet, J=7.3 Hz 2H), 3.01 (quartet, J=8.1 Hz, 4H), 5.39 (s, 2H), 6.84 (d, J=8.6 Hz, 1H), 7.28-7.33 (m, 1H), 7.37 (t, J=7.32, 3H), 7.41-7.48 (m, 3H), 7.53 (s, 1H), 8.03 (d, J=8.6 Hz, 1H), 8.22 (s, 1H).

Step D: Preparation of 3-(2,3-Dihydro-1H-inden-5-yl)-3H-imidazo[4,5-b]pyridin-5-ol (Compound 5)

From 5-(benzyloxy)-3-(2,3-dihydro-1H-inden-5-yl)-3H-imidazo[4,5-b]pyridine, prepared in a similar manner as the one described in Example 1.11, Step B, the title compound was obtained. $^1$H NMR (400 MHz, DMSO-d$_6$) δ ppm 2.09 (q, J=7.4 Hz, 2H), 2.93 (q, J=6.8 Hz, 4H), 6.61 (d, J=8.6 Hz, 1H), 7.41 (d, J=8.3 Hz, 1H), 7.55 (dd, J$_1$=8.0 Hz, J$_2$=1.93 Hz, 1H), 7.66 (s, 1H), 7.99 (d, J=8.6 Hz, 1H), 8.45 (s, 1H), 10.81 (s, 1H).

Example 1.116

Preparation of 2-Methyl-3-phenyl-3H-imidazo[4,5-b]pyridin-5-ol (Compound 6)

6-(Benzyloxy)-N$^2$-phenylpyridine-2,3-diamine (68 mg, 0.23 mmol) was dissolved in trimethyl orthoacetate (5.0 mL) and TFA (10 μL) was added. The mixture was stirred at room temperature for 2 h and concentrated in vacuo. The benzyl group of the residue was then removed as described in Example 1.11, Step B to give the title compound as a white solid (15 mg). $^1$H NMR (400 MHz, DMSO-d$_6$) δ ppm 2.35 (s, 1H), 6.51 (d, J=8.6 Hz, 1H), 7.48-7.55 (m, 3H), 7.57-7.63 (m, 2H), 7.84 (d, J=8.6 Hz, 1H).

Example 1.117

Preparation of 3-Phenyl-2-propyl-3H-imidazo[4,5-b]pyridin-5-ol (Compound 7)

A mixture of 6-(benzyloxy)-N$^2$-phenylpyridine-2,3-diamine (90 mg, 0.31 mmol), trimethyl orthobutyrate (5 mL), and TFA (20 μL) was stirred at room temperature for 2 h. The mixture was concentrated in vacuo and the residue dissolved in MeOH (5 mL). Palladium on carbon (20% wt./wt., 15 mg,) was added and the mixture was stirred vigorously under H$_2$ (1 atm) for 1 h. The mixture was filtered through Celite® and concentrated to give the title compound as a white solid (26 mg). $^1$H NMR (400 MHz, DMSO-d$_6$) δ ppm 0.85 (t, J=7.6 Hz, 3H), 1.65 (s, J=7.3 Hz, 2H), 2.62 (t, J=7.6 Hz, 2H), 6.51 (d, J=8.6 Hz, 1H), 7.45-7.56 (m, 3H), 7.60 (t, J=7.6 Hz, 2H), 7.87 (d, J=8.3 Hz, 1H), 10.75 (br s, 1H).

Example 1.118

Preparation of 2,3-Diphenyl-3H-imidazo[4,5-b]pyridin-5-ol (Compound 8)

From 6-(benzyloxy)-N$^2$-phenylpyridine-2,3-diamine and trimethyl orthobenzoate, prepared in a similar manner as the one described in Example 1.117, the title compound was obtained as a white solid. $^1$H NMR (400 MHz, DMSO-d$_6$) δ ppm 6.61 (d, J=8.3 Hz, 1H), 7.29-7.57 (m, 10H), 8.00 (d, J=8.6 Hz, 1H), 11.07 (broad s, 1H).

Example 1.119

Preparation of 2-Amino-3-phenyl-3H-imidazo[4,5-b]pyridin-5-ol (Compound 9)

Step A. Preparation of 5-(Benzyloxy)-3-phenyl-3H-imidazo[4,5-b]pyridin-2-amine A solution of 6-(benzyloxy)-N$^2$-phenylpyridine-2,3-diamine (3.106 g, 10.66 mmol), and cyanogen bromide (1.694 g, 15.99 mmol) in EtOH (50 mL) was stirred overnight at room temperature. The mixture was diluted with EtOAc and saturated NaHCO$_3$. The layers were separated and the aqueous phase was back-extracted with EtOAc. The organics were dried over MgSO$_4$, filtered, and concentrated in vacuo. The residue was purified by silica gel chromatography to give the title compound (446 mg). LCMS m/z=317.1 [M+H]$^+$.

Step B. Preparation of 2-Amino-3-phenyl-3H-imidazo[4,5-b]pyridin-5-ol (Compound 9)

From 5-(benzyloxy)-3-phenyl-3H-imidazo[4,5-b]pyridin-2-amine, prepared in a similar manner as the one described in Example 1.99, Step D, the title compound was obtained as a white solid. LCMS m/z=227.3, [M+H]$^+$. $^1$H NMR (400 MHz, methanol-d$_4$) δ ppm 0.10 (broad s, 1H), 6.46 (d, J=8.3 Hz, 1H), 7.47-7.64 (m, 6H).

Example 1.120

Preparation of 3-(4-Methoxyphenyl)-3H-imidazo[4,5-b]pyridin-5-ol (Compound 11)

From 5-(benzyloxy)-3H-imidazo[4,5-b]pyridine and 4-methoxyphenylboronic acid, prepared in a similar manner as the one described in Example 1.25, Steps A and B, the title compound was obtained as a white solid. $^1$H NMR (400 MHz, methanol-d$_4$) δ ppm 3.9 (s, 3H), 6.92 (d, J=8.8 Hz, 1H), 7.16 (d, J=8.8 Hz, 2H), 7.73 (d, J=8.8 Hz, 2H), 8.10 (d, J=8.8 Hz, 1H), 9.20 (s, 1H).

Example 1.121

Preparation of 3-p-Tolyl-3H-imidazo[4,5-b]pyridin-5-ol (Compound 12)

Step A: Preparation of 5-(Benzyloxy)-3-p-tolyl-3H-imidazo[4,5-b]pyridine 5-(Benzyloxy)-3H-imidazo[4,5-b]pyridine (0.204 g, 0.906 mmol), 4-bromotoluene (0.123 mL, 0.996 mmol), potassium carbonate (263 mg, 1.90 mmol), copper(1) iodide (8.6 mg, 0.045 mmol) and NMP (3 mL) were heated at 210° C. for 1 h under microwave irradiation in a heavy walled sealed tube. The mixture was cooled to room temperature and diluted with EtOAc. The solution was washed with water and the organics were dried over MgSO$_4$, filtered, and concentrated. The residue was purified by column chromatography to give a mixture of the title compound and its regioisomer 5-(benzyloxy)-1-p-tolyl-1H-imidazo[4,5-b]pyridine (154 mg). LCMS m/z=316.3 [M+H]⁺.

Step B: Preparation of
3-p-Tolyl-3H-imidazo[4,5-b]pyridin-5-ol
(Compound 12)

From the mixture of 5-(benzyloxy)-3-p-tolyl-3H-imidazo [4,5-b]pyridine and 5-(benzyloxy)-1-p-tolyl-1H-imidazo[4,5-b]pyridine, the benzyl group was removed as described in Example 1.11, Step B. Purification by preparative HPLC gave the title compound as a white solid. $^1$H NMR (400 MHz, methanol-d$_4$) δ ppm 2.41 (s, 3H), 6.70 (d, J=8.8 Hz, 1H), 7.36 (d, J=8.3 Hz, 2H), 7.67 (d, J=8.3 Hz, 2H), 7.95 (d, J=8.6 Hz, 1H), 8.43 (s, 1H).

Example 1.122

Preparation of 2-(Methylthio)-3-phenyl-3H-imidazo [4,5-b]pyridin-5-ol (Compound 17)

Step A: Preparation of 5-(Benzyloxy)-3-phenyl-1H-imidazo[4,5b]pyridine-2(3H)-thione 6-(Benzyloxy)-N²-phenylpyridine-2,3-diamine (487 mg, 1.67 mmol) was taken up in DCM (12 mL) and 1,1'-thiocarbonyldiimidazole (328 mg, 1.84 mmol) was added. The mixture was stirred for 12 h at room temperature and concentrated in vacuo. The residue was purified by column chromatography to give the title compound (392 mg). $^1$H NMR (400 MHz, DMSO-d$_6$) δ ppm 5.13 (s, 1H), 6.73 (d, J=8.3 Hz, 1H), 7.31 (m, 5H), 7.5-7.56 (m, 3H), 7.57-7.64 (m, 3H).

Step B: Preparation of 5-(Benzyloxy)-2-(methylthio)-3-phenyl-3H-imidazo[4,5b]pyridine To a solution of 5-(benzyloxy)-3-phenyl-1H-imidazo[4,5b]pyridine-2(3H)-thione (132 mg, 0.396 mmol) in DMF/H₂O (1:1, 10 mL) was added 0.1 M sodium hydroxide (3.96 ml, 0.396 mmol) and iodomethane (0.0493 mL, 0.793 mmol). The reaction mixture was stirred for 12 h at room temperature. Water (50 mL) was added and the mixture was extracted with EtOAc. The organics were dried over MgSO₄, filtered, and concentrated. The residue was purified by column chromatography to give the title compound (95 mg). LCMS m/z=348.3 [M+H]⁺.

Step C: Preparation of 2-(Methylthio)-3-phenyl-3H-imidazo[4,5-b]pyridin-5-ol (Compound 17)

From 5-(benzyloxy)-2-(methylthio)-3-phenyl-3H-imidazo[4,5b]pyridine, the benzyl group was removed as described in Example 1.98, Step B to give the title compound. $^1$H NMR (400 MHz, methanol-d$_4$) δ ppm 2.67 (s, 3H), 6.59 (d, J=8.6 Hz, 1H), 7.46-7.62 (m, 5H), 7.83 (d, J=8.6 Hz, 1H).

Example 1.123

Preparation of
2-Chloro-3-phenyl-3H-imidazo[4,5-b]pyridin-5-ol
(Compound 31)

Step A. Preparation of 5-(Benzyloxy)-3-phenyl-1H-imidazo[4,5b]pyridine-2(3H)-one 6-(Benzyloxy)-N²-phenylpyridine-2,3-diamine (2.74 g, 9.39 mmol) was taken up in DCM (20 mL) and 1,1'-carbonyldiimidazole (CDI) (1.676 g, 10.33 mmol) was added. The reaction mixture was stirred for 12 h at room temperature and concentrated in vacuo. The residue was purified by column chromatography to give the title compound (2.49 g). LCMS m/z=318.3 [M+H]⁺.

Step B. Preparation of
2-Chloro-3-phenyl-3H-imidazo[4,5-b]pyridin-5-ol
(Compound 31)

A solution of 5-(benzyloxy)-3-phenyl-1H-imidazo[4,5b] pyridine-2(3H)-one (2.11 g, 6.65 mmol) in POCl₃ (5 mL) was heated at 80° C. for 1 h. The mixture was cooled to room temperature and carefully poured into a saturated solution of NaHCO₃ (20 mL). The mixture was extracted with EtOAc and the organics were dried over MgSO₄, filtered and concentrated. The residue was purified by HPLC to give the title compound as a white solid (9.9 mg). $^1$H NMR (400 MHz, DMSO-d$_6$) δ ppm 6.62 (d, J=8.6 Hz, 1H), 7.54-7.65, (m, 5H), 7.96 (d, J=8.6 Hz, 1H).

Example 1.124

Preparation of 2-Chloro-3-(2-fluorophenyl)-3H-imidazo[4,5-b]pyridin-5-ol (Compound 102)

Step A. Preparation of 5-(Benzyloxy)-3-(2-fluorophenyl)-1H-imidazo[4,5b]pyridine-2(3H)-one To a solution of 6-(benzyloxy)-N-(2-fluorophenyl)-3-nitropyridin-2-amine (2.00 g, 5.89 mmol) in dioxane (100 mL) was added Raney nickel (346 mg, 5.89 mmol). The mixture was stirred under hydrogen at room temperature for 12 h, filtered through Celite® and concentrated to give 6-(benzyloxy)-N²-(2-fluorophenyl)pyridin-2,3-diamine as an oil. The residual oil was dissolved in DCM (50 mL) and CDI (629 mg, 3.88 mmol) was added. After stirring at room temperature for 12 h the mixture was concentrated and purified by column chromatography to give the title compound (643 mg). LCMS m/z=336.4 [M+H]⁺.

Step B. Preparation of 5-(benzyloxy)-2-chloro-3-(2-fluorophenyl)-3H-imidazo[4,5b]pyridine A solution of 5-(benzyloxy)-3-(2-fluorophenyl)-1H-imidazo[4,5b]pyridine-2(3H)-one (244 mg, 0.728 mmol) in POCl₃ (5 mL) was heated at 80° C. for 5 h. After cooling to room temperature, saturated NaHCO₃ (100 mL) was added the mixture was extracted with EtOAc. The organics were dried over MgSO₄, filtered and concentrated to give the title compound as a brown waxy solid (271 mg). LCMS m/z=354.0 [M+H]⁺.

Step C. Preparation of 2-Chloro-3-(2-fluorophenyl)-3H-imidazo[4,5-b]pyridin-5-ol (Compound 102)

From 5-(benzyloxy)-2-chloro-3-(2-fluorophenyl)-3H-imidazo[4,5b]pyridine, the benzyl group was removed as described in Example 1.98, Step B to give the title compound as a purple solid. LCMS m/z=263.8, [M+H]⁺; $^1$H NMR (400 MHz, DMSO-d$_6$) δ ppm 6.64 (d, J=8.3 Hz, 1H), 7.47 (t, J=7.6 Hz, 1H), 7.58 (t, J=9.1 Hz, 1H), 7.64-7.78 (m, 1H), 7.99 (d, J=8.6 Hz, 1H), 11.1 (s, 1H).

Example 1.125

Preparation of 2-Bromo-3-(2-fluorophenyl)-3H-imidazo[4,5-b]pyridin-5-ol (Compound 103)

Step A. Preparation of 5-(Benzyloxy)-2-bromo-3-(2-fluorophenyl)-3H-imidazo[4,5-b]pyridine A solution of 5-(benzyloxy)-3-(2-fluorophenyl)-1H-imidazo[4,5-b]pyridin-2(3H)-one (244 mg, 0.728 mmol) and POBr$_3$ (2.086 g, 7.28 mmol) in toluene (30 mL) was heated to 100° C. for 72 h in a 40 mL sealed scintillation vial. After cooling to room temperature, the reaction mixture was poured into saturated aqueous NaHCO$_3$ (200 mL) and the mixture was extracted with EtOAc. The organics were washed with brine, dried over MgSO$_4$, filtered, and concentrated to give the title compound (148 mg). LCMS m/z=398.0 [M+H]$^+$.

Step B. Preparation of 2-Bromo-3-(2-fluorophenyl)-3H-imidazo[4,5-b]pyridin-5-ol (Compound 103)

From 5-(benzyloxy)-2-bromo-3-(2-fluorophenyl)-3H-imidazo[4,5-b]pyridine, the benzyl group was removed as described in Example 1.98, Step B to give the title compound. LCMS m/z=308.2 [M+H]$^+$; $^1$H NMR (400 MHz, DMSO-d$_6$) δ ppm 6.61 (d, J=8.8 Hz, 1H), 7.46 (t, J=7.6 Hz, 1H), 7.57 (t, J=9.2 Hz, 1H), 7.63-7.76 (m, 2H), 7.99 (d, J=8.6 Hz, 1H), 11.09 (s, 1H).

Example 1.126

Preparation of 2-Bromo-3-(2-chlorophenyl)-3H-imidazo[4,5-b]pyridin-5-ol (Compound 105)

From 6-(benzyloxy)-N-(2-chlorophenyl)-3-nitropyridin-2-amine, prepared in a similar manner as the one described in Example 1.125, the title compound was obtained. LCMS m/z=326.0 [M+H]$^+$.

Example 1.127

Preparation of 3-cyclohexyl-2-methyl-3H-imidazo[4,5-b]pyridin-5-ol (Compound 126)

Step A: Preparation of 6-Chloro-N-cyclohexyl-3-nitropyridin-2-amine 2,6-Dichloro-3-nitropyridine (5 g, 25.9 mmol) and cyclohexanamine (5.14 g, 51.8 mmol) were added to ethanol (17.5 mL). The reaction mixture was heated at 140° C. by microwave irradiation for 3 h. A yellow solid precipitated out. The solid was filtered, washed with cold ethanol, and dried under vacuum to afford the title compound (2.162 g) without further purification. LCMS m/z=256.40 [M+H]$^+$.

Step B: Preparation of 6-(Cyclohexylamino)-5-nitropyridin-2-ol

To a solution of 6-chloro-N-cyclohexyl-3-nitropyridin-2-amine (2.16 g, 8.45 mmol) dissolved in dioxane (845 mL) was added 3 M aqueous potassium hydroxide (8.5 mL). The reaction mixture was heated at 100° C. until LCMS showed the starting material was entirely consumed. The reaction mixture was cooled to room temperature and then diluted with water. 1 N HCl was added until the solution turned acidic and a solid was formed. The solid was filtered, washed with water, and dried under vacuum to afford the title compound as a yellow solid (1.58 g). LCMS m/z=238.30 [M+H]$^+$.

Step C: Preparation of 5-Amino-6-(cyclohexylamino)pyridin-2-ol 6-(Cyclohexylamino)-5-nitropyridin-2-ol (0.2 g, 0.843 mmol) was dissolved in methanol (168 mL). Palladium (5% Pd/C, 145 mg, 0.0063 mmol) was added. The reaction was flushed with nitrogen and stirred under a balloon filled with hydrogen for 3 h at room temperature. The reaction was monitored by TLC until the starting materials were consumed. The mixture was filtered through Celite® and concentrated to give the title compound as a dark green solid which was used immediately in next step without further purification.

Step D: Preparation of 3-Cyclohexyl-2-methyl-3H-imidazo[4,5-b]pyridin-5-ol (Compound 126)

5-Amino-6-(cyclohexylamino) pyridin-2-ol (0.1 g, 0.482 mmol) was dissolved in trimethyl orthoacetate (3.0 mL, 27.4 mmol). Several drops of TFA were added and the reaction mixture was stirred at room temperature overnight. The reaction mixture was concentrated and the residues were diluted with water/acetonitrile (1:1). The mixture was purified via HPLC to give the title compound (0.006 g). LCMS m/z=232.30 [M+H]$^+$; $^1$H NMR (400 MHz, methanol-d$_4$) δ ppm 1.43-1.5 (m, 1H), 1.53-1.63 (m, 2H), 1.83 (d, J=11.87 Hz, 1H), 2.01 (d, J=10.99 Hz, 4H), 2.64-2.74 (m, 2H), 2.89 (s, 3H), 4.51-4.57 (m, 1H), 6.90 (d, J=8.8 Hz, 1H), 8.0 (d, J=8.8 Hz, 1H).

Example 1.128

Preparation of 3-(2-Bromophenyl)-2-methyl-3H-imidazo[4,5-b]pyridin-5-ol (Compound 128)

From 2,6-dichloro-3-nitropyridine and 2-bromoaniline, prepared in a similar manner as the one described in Example 1.127, the title compound was obtained. LCMS m/z=304.20 [M+H]$^+$, $^1$H NMR (400 MHz, methanol-d$_4$) δ ppm 2.64 (m, 3H), 6.92 (d, J=8.8 Hz, 1H), 7.64-7.72 (m, 3H), 7.99 (d, J=8.0 Hz, 1H), 8.10 (d, J=8.8 Hz, 1H).

Example 1.129

Preparation of 3-(1-Ethylcyclohexyl)-2-methyl-3H-imidazo[4,5-b]pyridin-5-ol (Compound 139)

From 2,6-dichloro-3-nitropyridine and 1-ethylcyclohexanamine, prepared in a similar manner as the one described in Example 1.127, the title compound was obtained. LCMS m/z=260.30 [M+H]$^+$. $^1$H NMR (400 MHz, methanol-d$_4$) δ ppm 0.64 (t, J=7.5 Hz, 3H), 1.51-1.68 (m, 4H), 1.72-1.80 (m, 2H), 2.28-2.36 (m, 2H), 2.39 (q, J=7.5 Hz, 2H), 2.68-2.74 (m, 2H), 4.04 (s, 3H), 7.13 (d, J=8.9 Hz, 1H), 8.18 (d, J=8.9 Hz, 1H).

Example 1.130

Preparation of 3-(biphenyl-2-yl)-3H-imidazo[4,5-b]pyridin-5-ol (Compound 40)

From 5-(benzyloxy)-3H-imidazo[4,5-b]pyridine and biphenyl-2-ylboronic acid, prepared in a similar manner as the one described in Example 1.26, the title compound was obtained. LCMS m/z=288.0 [M+H]+.

Example 1.131

Preparation of 2-Methyl-3-(1-methylcyclohexyl)-3H-imidazo[4,5-b]pyridin-5-ol (Compound 140)

Step A: Preparation of Intermediate 5-Amino-6-(1-methylcyclohexylamino) pyridin-2-ol From 2,6-dichloro-3-nitropyridine and 1-methylcyclohexanamine, prepared in a similar manner as the one described in Example 1.127, Step A, B, and C, the title compound was obtained.

Step B: Preparation of 2-Methyl-3-(1-methylcyclohexyl)-3H-imidazo[4,5-b]pyridin-5-ol (Compound 140)

From 5-amino-6-(1-methylcyclohexylamino)pyridin-2-ol and trimethyl orthoacetate, prepared in a similar manner as the one described in Example 1.127, Step D, the title compound was obtained. LCMS m/z=246.10 [M+H]+. 1H NMR (400 MHz, methanol-$d_4$) δ ppm 1.52-1.58 (m, 1H), 1.67-1.78 (m, 5H), 1.90 (s, 3H), 2.48-2.52 (m, 2H), 2.75-2.82 (m, 2H), 3.02 (s, 3H), 6.91 (d, J=8.8 Hz, 1H), 7.98 (d, J=8.8 Hz, 1H).

Example 1.132

Preparation of 3-(2-Methylcyclohexyl)-3H-imidazo [4,5-b]pyridin-5-ol (Compound 119)

Step A: Preparation of 5-Amino-6-(2-methylcyclohexylamino)pyridin-2-ol

From 2,6-dichloro-3-nitropyridine and 2-methylcyclohexanamine, prepared in a similar manner as the one described in Example 1.131, Step A, the title compound was obtained.

Step B: Preparation of 3-(2-Methylcyclohexyl)-3H-imidazo[4,5-b]pyridin-5-ol (Compound 119)

6-(2-Methylcyclohexylamino)-5-nitropyridin-2-ol (100 mg, 0.398 mmol) and nickel (11.68 mg, 0.199 mmol) in MeOH (10 mL) were stirred at 22° C. for 24 hr under $H_2$. After filtration through Celite®, the solution was concentrated in the presence of a few drops of TFA. The residue was dissolved in trimethoxymethane (2112 mg, 19.90 mmol) and stirred overnight with a drop of TFA. The mixture was concentrated. The residue was diluted with water, neutralized with $NaHCO_3$ solution and extracted with EtOAC. The EtOAc extract was concentrated and the residue was purified by column chromatography to give the title compound as a brown oil (37 mg). LCMS m/z=232.10 [M+H]+, 1H NMR (400 MHz, $CDCl_3$) major isomer; δ ppm 0.75 (d, J=6.3 Hz, 3H), 1.22-2.20 (m, 9H), 4.18-4.27 (m, 1H), 6.89 (d, J=8.9 Hz, 1H), 8.17 (d, J=8.9 Hz, 1H), 8.52 (s, 1H).

Example 1.133

Preparation of 3-(1-Methylcyclohexyl)-3H-imidazo [4,5-b]pyridin-5-ol (Compound 137)

From 5-amino-6-(1-methylcyclohexylamino)pyridin-2-ol and trimethyl orthoformate, prepared in a similar manner as the one described in Example 1.127, Step D, the title compound was obtained. LCMS m/z=232.20 [M+H]+. 1H NMR (400 MHz, methanol-$d_4$) δ ppm 1.54-1.67 (m, 4H), 1.68-1.76 (m, 2H), 1.83 (s, 3H), 2.22-2.30 (m, 2H), 2.59-2.68 (m, 2H), 6.94 (d, J=8.8 Hz, 1H), 8.07 (d, J=8.8 Hz, 1H), 9.17 (s, 1H).

Example 1.134

Preparation of 3-Cyclohexyl-2-hydroxy-3H-imidazo [4,5-b]pyridin-5-yl methanesulfonate Step A: Preparation of 6-(Cyclohexylamino)-5-nitropyridin-2-yl methanesulfonate 6-(Cyclohexylamino)-5-nitropyridin-2-ol (1.35 g, 5.69 mmol) was dissolved in DCM (1150 mL). Methanesulfonyl chloride (0.782 g, 6.83 mmol) and triethylamine (1.152 g, 11.38 mmol) was added. The reaction mixture was stirred at room temperature for 2 h, acidified with 1 M HCl and extracted with DCM. The organic layers were combined, washed with water, dried over $Na_2SO_4$, and concentrated under reduced pressure to give the title compound without further purification. LCMS m/z=316.30 [M+H]+.

Step B: Preparation of 5-Amino-6-(cyclohexylamino)pyridin-2-yl Methanesulfonate 6-(Cyclohexylamino)-5-nitropyridin-2-yl methanesulfonate (1.58 g, 5.01 mmol) was dissolved in methanol (1000 mL). Palladium (5% Pd/C, 1.72 g, 0.075 mmol) was added. The reaction was flushed with nitrogen and stirred under a balloon filled with hydrogen over 3 h at room temperature. The mixture was filtered through Celite® and concentrated to give the title compound as a dark green solid which was used immediately in next step without further purification.

Step C: Preparation of 3-Cyclohexyl-2-hydroxy-3H-imidazo[4,5-b]pyridin-5-yl Methanesulfonate 5-Amino-6-(cyclohexylamino)pyridin-2-yl methanesulfonate (1.44 g, 5.05 mmol) was dissolved in THF (30 mL) and CDI (2.455 g, 15.14 mmol) was added. The mixture was heated at 70° C. for 3 h. THF was removed and the residue was dissolved in EtOAc. The resulting solution was washed with water followed by 1 M HCl, dried over $MgSO_4$ and concentrated under reduced pressure to give the title compound (0.96 g) without further purification. LCMS m/z=312.50 [M+H]+.

Example 1.135

Preparation of 3-(2-Bromophenyl)-2-hydroxy-3H-imidazo[4,5-b]pyridin-5-yl Methanesulfonate From 6-(2-bromophenylamino)-5-nitropyridin-2-ol, prepared in a similar manner as the one described in Example 1.134, the title compound was obtained. LCMS m/z=384.2 [M+H]+.

Example 1.136

Preparation of 2-Chloro-3-cyclohexyl-3H-imidazo[4,5-b]pyridin-5-ol (Compound 127)

Step A: Preparation of 2-Chloro-3-cyclohexyl-3H-imidazo[4,5-b]pyridin-5-yl methanesulfonate 3-Cyclohexyl-2-hydroxy-3H-imidazo[4,5-b]pyridin-5-yl methanesulfonate (0.4 g, 1.285 mmol) and $POCl_3$ (2.395 ml, 25.7 mmol) were placed in a sealed tube and heated to 80° C. for 48 h. The volatiles were removed under reduced pressure. The residue was dissolved in aqueous NaHCO$_3$ giving a basic solution. The solution was further diluted with water and extracted with EtOAc. The combined organics was dried over MgSO$_4$ and concentrated to give the title compound without further purification. LCMS m/z=330.30 [M+H]$^+$.

Step B: Preparation of 2-Chloro-3-cyclohexyl-3H-imidazo[4,5-b]pyridin-5-ol (Compound 127)

2-Chloro-3-cyclohexyl-3H-imidazo[4,5-b]pyridin-5-yl methanesulfonate (0.25 g, 0.758 mmol) was dissolved in 10 mL of a 1:4:1 of 1 M LiOH/THF/MeOH and stirred at room temperature for 1 h. The organic solvents were removed under reduced pressure and the remaining mixture was acidified with 1 M HCl to form a precipitate. The precipitate was collected, washed with water, and purified by HPLC to give the title compound (0.01 g). LCMS m/z=252.30 [M+H]$^+$, $^1$H NMR (400 MHz, methanol-d$_4$) δ ppm 1.39-1.43 (m, 1H), 1.45-1.54 (m, 2H), 1.8 (d, J=11.33 Hz, 1H), 1.88 (d, J=11.69 Hz, 2H), 1.98 (d, J=11.59 Hz, 2H), 2.59-2.69 (m, 2H), 4.52-4.59 (m, 1H), 6.64 (d, J=8.6 Hz, 1H), 7.79 (d, J=8.6 Hz, 1H).

Example 1.137

Preparation of 3-(2-Bromophenyl)-2-chloro-3H-imidazo[4,5-b]pyridin-5-ol (Compound 129)

From 3-(2-bromophenyl)-2-hydroxy-3H-imidazo[4,5-b]pyridin-5-yl methanesulfonate and POCl$_3$, prepared in a similar manner as the one described in Example 1.136, the title compound was obtained. LCMS m/z=323.90 [M+H]$^+$, $^1$H NMR (400 MHz, methanol-d$_4$) δ ppm 6.72 (d, J=8.6 Hz, 1H), 7.57-7.65 (m, 3H), 7.90 (dd, J$_1$=8.1 Hz, J$_2$=1.2 Hz, 1H), 7.93 (d, J=8.6 Hz, 1H).

Example 1.138

Preparation of 2-Bromo-3-(2-bromophenyl)-3H-imidazo[4,5-b]pyridin-5-ol (Compound 130)

From 3-(2-bromophenyl)-2-hydroxy-3H-imidazo[4,5-b]pyridin-5-yl methanesulfonate and phosphoryl tribromide, prepared in a similar manner as the one described in Example 1.136, the title compound was obtained. LCMS m/z=368.10 [M+H]$^+$, $^1$H NMR (400 MHz, methanol-d$_4$) δ ppm 6.70 (d, J=8.6 Hz, 1H), 7.57-7.64 (m, 3H), 7.90 (d, J=8.0, 1H), 7.94 (d, J=8.6 Hz, 1H).

Example 1.139

Preparation of 2-Chloro-3-o-tolyl-3H-imidazo[4,5-b]pyridin-5-ol (Compound 134)

Step A: Preparation of 6-Chloro-3-nitro-N-o-tolylpyridin-2-amine

From 2,6-dichloro-3-nitropyridine and o-toluidine, prepared in a similar manner as the one described in Example 1.127, Step A, the title compound was obtained. LCMS m/z=264.30 [M+H]$^+$.

Step B: Preparation of 5-Nitro-6-(o-tolylamino)pyridin-2-ol

From 6-chloro-3-nitro-N-o-tolylpyridin-2-amine, prepared in a similar manner as the one described in Example 1.127, Step B, the title compound was obtained. LCMS m/z=246.20 [M+H]$^+$.

Step C: Preparation of 2-Hydroxy-3-o-tolyl-3H-imidazo[4,5-b]pyridin-5-yl Methanesulfonate From 5-nitro-6-(o-tolylamino) pyridin-2-ol and methanesulfonyl chloride, prepared in a similar manner as the one described in Example 1.134, the title compound was obtained. LCMS m/z=320.30 [M+H]$^+$.

Step D: Preparation of 2-Chloro-3-o-tolyl-3H-imidazo[4,5-b]pyridin-5-ol (Compound 134)

From 2-hydroxy-3-o-tolyl-3H-imidazo[4,5-b]pyridin-5-yl, methanesulfonate and POCl$_3$, prepared in a similar manner as the one described in Example 1.136, the title compound was obtained. LCMS m/z=260.20 [M+H]$^+$, $^1$H NMR (400 MHz, methanol-d$_4$) δ ppm 2.18 (s, 3H), 7.17 (d, J=8.1, 1H), 7.34 (d, J=7.8, 1H), 7.38-7.43 (m, 1H), 7.44-7.48 (m, 3H).

Example 1.140

Preparation of 2-Bromo-3-o-tolyl-3H-imidazo[4,5-b]pyridin-5-ol (Compound 135)

From 2-hydroxy-3-o-tolyl-3H-imidazo[4,5-b]pyridin-5-yl methanesulfonate and phosphoryl tribromide, prepared in a similar manner as the one described in Example 1.136, the title compound was obtained. LCMS m/z=304.20 [M+H]$^+$, $^1$H NMR (400 MHz, methanol-d$_4$) δ ppm 2.05 (s, 3H), 6.7 (d, J=8.6 Hz, 1H), 7.33 (d, J=7.8, 1H), 7.42-7.47 (m, 1H), 7.48-7.53 (m, 2H), 7.94 (d, J=8.7, 1H).

Example 1.141

Preparation of 3-(Bicyclo[2.2.1]heptan-2-yl)-2-chloro-3H-imidazo[4,5-b]pyridin-5-ol (Compound 136)

From 2,6-dichloro-3-nitropyridine and bicyclo[2.2.1]heptan-2-amine, prepared in a similar manner as the one described in Example 1.139, the title compound was obtained. LCMS m/z=264.20 [M+H]$^+$, $^1$H NMR (400 MHz, methanol-d$_4$) δ ppm 1.37 (d, J=8.1 Hz, 2H), 1.43-1.49 (m, 1H), 1.67-1.72 (m, 2H), 1.85-1.91 (m, 1H), 2.55-2.60 (m, 3H), 3.08-3.13 (m, 1H), 4.52-4.56 (m, 1H), 6.63 (d, J=8.6 Hz, 1H), 7.78 (d, J=8.6 Hz, 1H).

Example 1.142

Preparation of 2-Chloro-3-(2-methylcyclohexyl)-3H-imidazo[4,5-b]pyridin-5-ol (Compound 138)

From 2,6-dichloro-3-nitropyridine and 2-methylcyclohexanamine, prepared in a similar manner as the one described in Example 1.139, the title compound was obtained. LCMS m/z=266.2 [M+H]$^+$.

Example 2

In-Vitro Biological Assays

Example 2.1

GPR81 [$^{35}$S]GTPγS Binding Assay

Compounds were screened for agonism of GPR81 (e.g. human GPR81) using a GTPγS binding assay and CHO-K1 cells stably transfected with GPR81.

GPR81 stably transfected CHO-K1 cells were grown in F-12 Kaighn's Modified Cell Culture Medium with 10% FBS, 2 mM L-glutamine, 1 mM sodium pyruvate and 400 μg/ml G418. For 15 cm$^2$ plates, cells were rinsed with 5 mL cold PBS and aspirated. Cold membrane scrape buffer (20 mM HEPES, 10 mM EDTA, pH 7.4) was added and cells were scraped off the plate and transferred to a 50 mL centrifuge tube. Cells were spun at 20,000 rpm for 17 minutes at 4° C. The supernatant was aspirated and the pellet was re-suspended in cold membrane wash buffer (30 mL, 20 mM HEPES, 0.1 mM EDTA, pH 7.4). Cells were spun at 20,000 rpm for 17 minutes at 4° C. The supernatant was aspirated away from the membrane pellet. The pellet may be frozen at −80° C. for later use or may be used immediately.

The membrane pellet was thawed (if frozen) on ice and homogenized briefly until in suspension using a polytron mixer (POLYTRON PT3100, probe PT-DA 3007/2 at setting of 7000 rpm). The membrane protein concentration was determined using a Bradford assay. The membrane protein was diluted to a protein concentration of 0.20 mg/mL in binding buffer (20 mM HEPES, pH 7.4, 100 mM NaCl, 10 mM MgCl$_2$) for a final assay concentration of 5 μg/well. Compound plates to be screened were thawed (daughter plates with 5 μL compound@2 mM in 100% DMSO). The 2 mM compounds were diluted 1:50 with 245 μL GDP buffer (binding buffer plus GDP, Sigma-Aldrich Catalog #87127, ranging from 0.4 to 40 μM, made fresh before assay) to 40 μM in 2% DMSO. Compounds in GDP buffer (25 were added per well of a Scintistrip plate (Wallac Catalog #1450-501) and then 50 μL of membrane preparation (0.4 mg protein/mL) was added to each well. The plates were then covered with foil and incubated for 5-10 minutes at room temperature. Subsequently, 25 μL of diluted [$^{35}$S]GTPγS (Amersham Biosciences Catalog #SJ1320, about 2000 Ci/mmol (made by adding 5 μL [$^{35}$S]GTPγS stock into 10 ml binding buffer) was added to the wells. The plates were covered with foil and incubated on a shaker (Lab-Line model #1314, at setting of 4) for 60 minutes at room temperature. The assay was stopped by sealing the plates with plate covers and spinning the plates at 4000 rpm for 15 minutes at 22° C. The supernatant of each well was apirated using an eight-channel manifold and the plate was read in a Wallac Microbeta counter 1450 set up to detect $^{35}$S.

Certain compounds of the present invention and their corresponding activity values are shown in TABLE B.

TABLE B

| Compound No. | EC$_{50}$ GPR81 (GTPγS) |
|---|---|
| 114 | 30.34 nM |
| 127 | 75.34 nM |
| 133 | 81.47 nM |
| 56 | 1.39 μM |

Certain other compounds of the invention had activity values ranging from about 14 nM to about 34.5 μM in this assay.

Example 2.2

Homogeneous Time-Resolved Fluorescence (HTRF®) Assay for Direct cAMP Measurement Compounds were screened for agonists of GPR81 (e.g., human GPR81) using an HTRF® assay for direct cAMP measurement (Gabriel et al, *ASSAY and Drug Development Technologies*, 1:291-303, 2003) and recombinant CHO-K1 cells stably transfected with GPR81. CHO-K1 cells were obtained from ATCC® (Manassas, Va.; Catalog #CCL-61). An agonist of GPR81 was detected in the HTRF® assay for direct cAMP measurement as a compound which decreased cAMP concentration. The HTRF® assay also was used to determine EC$_{50}$ values for GPR81 agonists.

The HTRF® assay kit was purchased from Cisbio-US, Inc. (Bedford, Mass.; Catalog #62AM4PEC). The HTRF® assay supported by the kit is a competitive immunoassay between endogenous cAMP produced by the CHO-K1 cells and tracer cAMP labeled with the dye d2. The tracer binding is visualized by a monoclonal anti-cAMP antibody labeled with Cryptate. The specific signal (i.e., fluorescence resonance energy transfer, FRET) is inversely proportional to the concentration of unlabeled cAMP in the standard or sample.

The fluorescence ratio (665 nm/620 nm) of the standards (0.17 to 712 nM cAMP) included in the assay was calculated and used to generate a cAMP standard curve according to the kit manufacturer's instructions. The fluorescence ratio of the samples (test compound or compound buffer) was calculated and used to deduce respective cAMP concentrations by reference to the cAMP standard curve.

The HTRF® assay was carried out using a two-step protocol essentially according to the kit manufacturer's instructions, in 20 μL total volume per well in 384-well plate format (ProxiPlates; PerkinElmer, Fremont, Calif.; catalog #6008280). To each of the experimental wells was transferred 1000 recombinant CHO-K1 cells in 5 μL phosphate buffered saline containing calcium chloride and magnesium chloride ("PBS+"; Invitrogen, Carlsbad, Calif.; catalog #14040) supplemented with IBMX (100 μM) (phosphodiesterase inhibitors; Sigma-Aldrich, St. Louis, Mo.; catalog #I-5879), followed by test compound in 5 μL compound buffer (PBS+ supplemented with 10 μM forskolin (Sigma-Aldrich, St. Louis, Mo.; catalog #F-6886)). The plate was then incubated at room temperature for 1 hour. To each well was then added 5 μl cAMP-d2 conjugate in lysis buffer and 5 μL Cryptate conjugate in lysis buffer according to the kit manufacturer's instructions. The plate was then further incubated at room temperature for 1 hour, after which the assay plate was read.

HTRF® readout was accomplished using a PHERAstar (BMG LABTECH Inc., Durham, N.C.) or EnVision™ (PerkinElmer, Fremont Calif.) microplate reader.

Certain compounds of the present invention and their corresponding activity values are shown in TABLE C.

TABLE C

| Compound No. | EC$_{50}$ GPR81 (HTRF) |
|---|---|
| 48 | 0.35 μM |
| 9 | 1.05 μM |
| 64 | 2.33 μM |
| 50 | 2.76 μM |

Certain other compounds of the invention had activity values ranging from about 0.23 μM to about 6.04 μM in this assay.

Example 3

In-Vivo Biological Assays

Example 3.1

Glycerol Assay (Rat Adipocyte Lipolysis)

Free glycerol was determined using a free glycerol reagent, Reagent A (Sigma). Adipocyte media (10 µL) was removed and replated in a flat-bottom 96-well plate. Reagent A (100 µL) was then added to each well. After 10-15 minutes, abroad sorbance was read at $OD_{540}$ on a Spectramax 340PC microplate reader (Molecular Devices). The amount of glycerol released was calculated based on regression analysis of known glycerol concentrations using a glycerol standard (Sigma).

Epididymal fat pads were surgically removed from $CO_2$-anesthetized male Sprague Dawley rats, weighing 300-500 g. The adipose tissue was minced and suspended in Krebroad s-Ringer bicarbonate HEPES buffer (containing 12 mM NaCl, 400 nM $KH_2PO_4$ (monobasic), 100 nM $MgSO_4.7H_2O$, 100 nM $CaCl_2$, 1 mM $NaHCO_3$, 3 mM HEPES, 200 nM adenosine, and 1% BSA) with 2.5 mg of collagenase (Sigma) per gram of tissue. The suspension was incubated in an orbital shaker at 37° C. for 40 minutes with constant agitation. Cells were then filtered through a 500 µm mesh filter. For each filter used, 10 mL of buffer was added to the cell suspension to aid with the filtration. Cells were spun at 1000 rpm for 1 minute. A glass Pasteur pipette was then used to remove all buffer remaining below the floating adipocyte layer. Approximately 30 mL of new buffer was then added to the adipocytes and they were incubated for 5 minutes at 37° C. All buffer remaining below the adipocyte layer was removed, 30 mL of new buffer was added, and cells were washed once more in this manner. After the final wash, adipocytes were plated in round-bottom 96-well plates at a density of approximately 5 g of starting tissue per plate.

Compound dilution series were prepared in Krebroad s buffer at two times the final concentration. Cells were incubated with compounds for 10 minutes at 37° C. prior to the addition of theophylline at a final concentration of 1.5 mM. Adipocytes were then incubated for 3 hours in a humidified incubator at 37° C. before performing the lipolysis assay.

For experiments involving the use of pertussis toxin (PTX), PTX was added directly to the cell suspension at a concentration of 100 ng/mL immediately before plating. For these experiments, cells were incubated with PTX alone for 2 hrs, followed by compound and theophylline addition (in the presence of PTX) for an additional 2 hrs.

Example 3.2

NEFA Assay

The NEFA assay was done as per manufacturer suggested protocol (Wako; NEFA-C). The supplied standard was diluted with DI water to 1, 0.5, 0.25, 0.125, 0.0625, 0.03125. A water blank was also prepared. Serum samples and standards were dispensed (5 µl/well) to wells of a 96-well plate. Reagent A (100 µL) was added to each well and incubated for 10 minutes at 37° C. Reagent B (200 µL) was then added to each well and incubated for another 10 minutes at 37° C. After equilibration for 5 minutes at room temperature (about 25° C.), the abroad sorbance was measured on a plate reader at 550 nm.

Male Sprague Dawley rats (10-12 weeks old) were obtained from Charles River Labroad s pre-cannulated with right jugular catheters for sample collection. Rats were food deprived overnight (by removing food pellets from the cage) for approximately 16 hours with ad libitum access to water. Canulae were flushed with saline to remove heparin and to clear the catheter line 30 minutes prior to the first (basal) sample collection. Basal samples were collected in a staggered dose manner (e.g. vehicle, high dose, low dose, low dose, high dose, and vehicle). Rats were injected per oral (PO), 2 mL/kg with 5% HPBCD (Hydroxypropyl-β-cyclodextrin) or with drug in 5% HPBCD. Blood (500-700 µl) was drawn via catheter at 10, 20, 40, 60, 120, and 240 minutes post dosing, and saline (about 200 µl) was infused into the catheter to ensure patency. Samples were stored at room temperature for 0.5 to 1 hour and were then spun down in a centrifuge at 10000 rpm for 4 minutes at room temperature, and serum was removed and placed in a 200 µL Eppendorf tube on ice. The serum was then spun again at 4° C., 4000 rpm for 10 minutes. Serum samples were dispensed (5 µL/well) to wells of a 96-well plate.

Male C57/B16 mice (8-10 weeks old; about 23 g) were food deprived (by removing food pellets from the cage) for 5 hours with ad libitum access to water. Animals were then dosed with vehicle (5% HPBCD) or drug via intraperitoneal (IP) injection at the desired concentration in a volume of 10 mL/kg. After 30 minutes, mice were euthanized via $CO_2$ asphyxiation and about 300 µl of blood were immediately collected by cardiac puncture. The blood was transferred to an Eppendorf tube and capped on ice. The blood was then centrifuged on a table top centrifuge (4000 rpm at 4° C. for 10 minutes). Serum was collected in a new microfuge tube and re-centrifuged (4000 rpm at 4° C. for 10 minutes). Serum samples were dispensed (5 µl/well) to wells of a 96-well plate.

Those skilled in the art will recognize that various modifications, additions, substitutions and variations to the illustrative examples set forth herein can be made without departing from the spirit of the invention and are, therefore, considered within the scope of the invention. All documents referenced above, including, but not limited to, printed publications and provisional and regular patent applications, are incorporated herein by reference in their entirety.

What is claimed is:

1. A compound selected from compounds of Formula (Ia) and pharmaceutically acceptable salts, solvates and hydrates thereof:

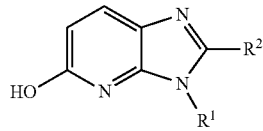

(Ia)

wherein:

$R^1$ is aryl, heteroaryl, $C_3$-$C_{10}$ cycloalkyl, or heterocyclyl, each optionally substituted with 1, 2, or 3 substitutents independently selected from the group consisting of $C_1$-$C_6$ alkoxy, $C_1$-$C_6$ alkoxycarbonyl, $C_1$-$C_6$ alkyl, $C_1$-$C_6$ alkylthio, aryl, $C_3$-$C_6$ cycloalkyl, halogen, $C_1$-$C_6$ haloalkoxy, $C_1$-$C_6$ haloalkyl, $C_1$-$C_6$ haloalkylthio, hydroxyl, nitro, and oxo, wherein $C_1$-$C_6$ alkyl is optionally substituted with aryl; or two adjacent substitutents together with the atoms to which they are both bonded form a five-membered cycloalkyl or a five-membered heterocyclyl; and $R^2$ is H, $C_1$-$C_6$ alkyl, $C_1$-$C_6$ alkylthio, amino, aryl, $C_3$-$C_6$ cycloalkyl, or halogen.

2. The compound according to claim 1, wherein $R^1$ is phenyl or naphthalenyl, each optionally substituted with 1, 2, or 3 substitutents independently selected from the group consisting of $C_1$-$C_6$ alkoxy, $C_1$-$C_6$ alkyl, $C_1$-$C_6$ alkylthio, aryl, $C_3$-$C_6$ cycloalkyl, halogen, $C_1$-$C_6$ haloalkoxy, $C_1$-$C_6$ haloalkyl, $C_1$-$C_6$ haloalkylthio, and nitro, and wherein $C_1$-$C_6$ alkyl is optionally substituted with aryl, or two adjacent substitutents together with the atoms to which they are both bonded form a five-membered cycloalkyl or a five-membered heterocyclyl.

3. The compound according to claim 1, wherein $R^1$ is phenyl or naphthalenyl, each optionally substituted with 1, 2, or 3 substitutents independently selected from the group consisting of methoxy, methyl, ethyl, isopropyl, cyclopropyl, methylthio, phenyl, bromo, chloro, fluoro, iodo, trifluoromethoxy, trifluoromethyl, trifluoromethylthio, and nitro.

4. The compound according to claim 1, wherein $R^1$ is selected from the group consisting of 2-(methylthio)phenyl, 2-(trifluoromethoxy)phenyl, 2-(trifluoromethylthio)phenyl, 2,3,4-trichlorophenyl, 2,3-dichlorophenyl, 2,3-difluorophenyl, 2,3-dihydro-1H-inden-4-yl, 2,3-dihydro-1H-inden-5-yl, 2,3-dimethylphenyl, 2,4,5-trichlorophenyl, 2,4-bis(trifluoromethyl)phenyl, 2,4-dichlorophenyl, 2,4-dimethylphenyl, 2,5-dimethylphenyl, 2,6-dichlorophenyl, 2-bromo-3-methylphenyl, 2-bromophenyl, 2-chloro-3-fluorophenyl, 2-chlorophenyl, 2-cyclopropylphenyl, 2-ethylphenyl, 2-fluoro-3-(trifluoromethyl)phenyl, 2-fluoro-3-methylphenyl, 2-fluorophenyl, 2-isopropylphenyl, 2-methoxyphenyl, 2-nitrophenyl, 3,4-dimethylphenyl, 3,5-dimethylphenyl, 3-bromo-2-(trifluoromethyl)phenyl, 3-chloro-2-fluorophenyl, 3-chloro-2-methylphenyl, 3-chlorophenyl, 3-fluoro-2-(trifluoromethyl)phenyl, 3-fluoro-2-methylphenyl, 4-benzylphenyl, 4-bromo-2-(trifluoromethyl)phenyl, 4-bromo-2-methylphenyl, 4-bromo-5-chloro-2-methylphenyl, 4-bromophenyl, 4-chloro-2-(trifluoromethyl)phenyl, 4-ethylphenyl, 4-fluoro-2-(trifluoromethyl)phenyl, 4-fluoro-2-methylphenyl, 4-fluorophenyl, 4-methoxyphenyl, 5-chloro-2-methylphenyl, benzo[d][1,3]dioxol-5-yl, biphenyl-2-yl, o-tolyl, phenyl, and p-tolyl.

5. The compound according to claim 1, wherein $R^1$ is selected from the group consisting of 2-methylnaphthalen-1-yl, 4-chloronaphthalen-1-yl, and naphthalen-1-yl.

6. The compound according to claim 1, wherein $R^1$ is heteroaryl, optionally substituted with halogen.

7. The compound according to claim 1, wherein $R^1$ is pyridinyl or thienyl, each optionally substituted with halogen.

8. The compound according to claim 1, wherein $R^1$ is 3-chloropyridin-4-yl or thiophen-3-yl.

9. The compound according to claim 1, wherein $R^1$ is $C_3$-$C_{10}$ cycloalkyl, optionally substituted with 1 or 2 substitutents independently selected from the group consisting of $C_1$-$C_6$ alkyl, halogen, hydroxyl, and oxo.

10. The compound according to claim 1, wherein $R^1$ is selected from the group consisting of 1-ethylcyclohexyl, 1-methylcyclohexyl, 2,2-difluorocycloheptyl, 2-hydroxycycloheptyl, 2-methylcyclohexyl, 2-oxocyclohexyl, 4-hydroxycyclohexyl, adamant-1-yl, bicyclo[2.2.1]heptan-2-yl, cyclobutyl, cycloheptanon-2-yl, cycloheptyl, cyclohexyl, cyclooctyl, and cyclopentyl.

11. The compound according to claim 1, wherein $R^1$ is heterocyclyl optionally substituted with $C_1$-$C_6$ alkoxycarbonyl.

12. The compound according to claim 1, wherein $R^1$ is selected from the group consisting of 1-(tert-butoxycarbonyl)azepan-4-yl, tetrahydro-2H-pyran-4-yl, and tetrahydro-2H-thiopyran-4-yl.

13. The compound according to claim 1, wherein $R^2$ is selected from the group consisting of H, amino, bromo, chloro, cyclopropyl, methyl, methylthio, phenyl, and n-propyl.

14. The compound according to claim 1, wherein $R^2$ is H.

15. The compound according to claim 1, wherein $R^2$ is methyl.

16. The compound according to claim 1, wherein $R^2$ is amino.

17. The compound according to claim 1, selected from compounds of Formula (Ia) and pharmaceutically acceptable salts, solvates and hydrates thereof:

wherein:

$R^1$ is aryl, optionally substituted with 1, 2, or 3 substitutents independently selected from the group consisting of $C_1$-$C_6$ alkoxy, $C_1$-$C_6$ alkyl, $C_1$-$C_6$ alkylthio, aryl, $C_3$-$C_6$ cycloalkyl, halogen, $C_1$-$C_6$ haloalkoxy, $C_1$-$C_6$ haloalkyl, $C_1$-$C_6$ haloalkylthio, and nitro, and wherein $C_1$-$C_6$ alkyl is optionally substituted with aryl, or two adjacent substitutents together with the atoms to which they are both bonded form a five-membered cycloalkyl or a five-membered heterocyclyl, $R^2$ is H, $C_1$-$C_6$ alkyl, $C_1$-$C_6$ alkylthio, amino, aryl, $C_3$-$C_6$ cycloalkyl, or halogen.

18. The compound according to claim 1, selected from compounds of Formula (Ia) and pharmaceutically acceptable salts, solvates and hydrates thereof:

wherein:

$R^1$ is selected from the group consisting of phenyl, naphthalenyl, pyridinyl, thienyl, adamantyl, cyclobutyl, cycloheptyl, cyclohexyl, cyclooctyl, cyclopentyl, azepanyl, tetrahydro-2H-pyranyl, and tetrahydro-2H-thiopyranyl, each optionally substituted with 1, 2, or 3 substitutents independently selected from the group consisting of tert-butoxycarbonyl, methoxy, methyl, ethyl, isopropyl, cyclopropyl, methylthio, phenyl, bromo, chloro, fluoro, hydroxyl, iodo, oxo, trifluoromethoxy, trifluoromethyl, trifluoromethylthio, and nitro; and $R^2$ is selected from the group consisting of H, amino, bromo, chloro, cyclopropyl, methyl, methylthio, phenyl, and n-propyl.

19. The compound according to claim 1, selected from compounds of Formula (Ia) and pharmaceutically acceptable salts, solvates and hydrates thereof:

wherein:

$R^1$ is selected from the group consisting of 2-(methylthio)phenyl, 2-(trifluoromethoxy)phenyl, 2-(trifluoromethylthio)phenyl, 2,3,4-trichlorophenyl, 2,3-dichlorophenyl, 2,3-difluorophenyl, 2,3-dihydro-1H-inden-4-yl, 2,3-dihydro-1H-inden-5-yl, 2,3-dimethylphenyl, 2,4,5-trichlorophenyl, 2,4-bis(trifluoromethyl)phenyl, 2,4-dichlorophenyl, 2,4-dimethylphenyl, 2,5-dimethylphenyl, 2,6-dichlorophenyl, 2-bromo-3-methylphenyl, 2-bromophenyl, 2-chloro-3-fluorophenyl, 2-chlorophenyl, 2-cyclopropylphenyl, 2-ethylphenyl, 2-fluoro-3-(trifluoromethyl)phenyl, 2-fluoro-3-methylphenyl, 2-fluorophenyl, 2-isopropylphenyl, 2-methoxyphenyl, 2-nitrophenyl, 3,4-dimethylphenyl, 3,5-dimethylphenyl, 3-bromo-2-(trifluoromethyl)phenyl, 3-chloro-2-fluorophenyl, 3-chloro-2-methylphenyl, 3-chlorophenyl, 3-fluoro-2-(trifluoromethyl)phenyl, 3-fluoro-2-methylphenyl, 4-benzylphenyl, 4-bromo-2-

(trifluoromethyl)phenyl, 4-bromo-2-methylphenyl, 4-bromo-5-chloro-2-methylphenyl, 4-bromophenyl, 4-chloro-2-(trifluoromethyl)phenyl, 4-ethylphenyl, 4-fluoro-2-(trifluoromethyl)phenyl, 4-fluoro-2-methylphenyl, 4-fluorophenyl, 4-methoxyphenyl, 5-chloro-2-methylphenyl, benzo[d][1,3]dioxol-5-yl, biphenyl-2-yl, o-tolyl, phenyl, and p-tolyl; and R² is selected from the group consisting of H, amino, bromo, chloro, cyclopropyl, methyl, methylthio, phenyl, and n-propyl.

20. The compound according to claim 1, selected from compounds of Formula (Ia) and pharmaceutically acceptable salts, solvates and hydrates thereof:
wherein:
R¹ is selected from the group consisting of 2-methylnaphthalen-1-yl, 4-chloronaphthalen-1-yl, and naphthalen-1-yl; and
R² is selected from the group consisting of H, amino, bromo, chloro, cyclopropyl, methyl, methylthio, phenyl, and n-propyl.

21. The compound according to claim 1, selected from compounds of Formula (Ia) and pharmaceutically acceptable salts, solvates and hydrates thereof:
wherein:
R¹ is selected from the group consisting of 1-ethylcyclohexyl, 1-methylcyclohexyl, 2,2-difluorocycloheptyl, 2-hydroxycycloheptyl, 2-methylcyclohexyl, cycloheptanon-2-yl, 2-oxocyclohexyl, 4-hydroxycyclohexyl, adamant-1-yl, bicyclo[2.2.1]heptan-2-yl, cyclobutyl, cycloheptanon-2-yl, cycloheptyl, cyclohexyl, cyclooctyl, and cyclopentyl; and
R² is selected from the group consisting of H, amino, bromo, chloro, cyclopropyl, methyl, methylthio, phenyl, and n-propyl.

22. The compound according to claim 1, selected from compounds of Formula (Ia) and pharmaceutically acceptable salts, solvates and hydrates thereof:
wherein:
R¹ is 3-chloropyridin-4-yl or thiophen-3-yl; and
R² is selected from the group consisting of H, amino, bromo, chloro, cyclopropyl, methyl, methylthio, phenyl, and n-propyl.

23. The compound according to claim 1, selected from compounds of Formula (Ia) and pharmaceutically acceptable salts, solvates and hydrates thereof:
wherein:
R¹ is selected from the group consisting of azepanyl, tetrahydro-2H-pyranyl, and tetrahydro-2H-thiopyranyl; and
R² is selected from the group consisting of H, amino, bromo, chloro, cyclopropyl, methyl, methylthio, phenyl, and n-propyl.

24. The compound according to claim 1, selected from the following compounds and pharmaceutically acceptable salts, solvates and hydrates thereof:
3-phenyl-3H-imidazo[4,5-b]pyridin-5-ol;
3-(3-chlorophenyl)-3H-imidazo[4,5-b]pyridin-5-ol;
3-(benzo[d][1,3]dioxol-5-yl)-3H-imidazo[4,5-b]pyridin-5-ol;
3-(4-benzylphenyl)-3H-imidazo[4,5-b]pyridin-5-ol;
3-(2,3-dihydro-1H-inden-5-yl)-3H-imidazo[4,5-b]pyridin-5-ol;
2-methyl-3-phenyl-3H-imidazo[4,5-b]pyridin-5-ol;
3-phenyl-2-propyl-3H-imidazo[4,5-b]pyridin-5-ol;
2,3-diphenyl-3H-imidazo[4,5-b]pyridin-5-ol;
2-amino-3-phenyl-3H-imidazo[4,5-b]pyridin-5-ol;
3-(4-fluorophenyl)-3H-imidazo[4,5-b]pyridin-5-ol;
3-(4-methoxyphenyl)-3H-imidazo[4,5-b]pyridin-5-ol;
3-p-tolyl-3H-imidazo[4,5-b]pyridin-5-ol;
2-amino-3-(4-ethylphenyl)-3H-imidazo[4,5-b]pyridin-5-ol;
2-amino-3-p-tolyl-3H-imidazo[4,5-b]pyridin-5-ol;
3-(4-ethylphenyl)-2-methyl-3H-imidazo[4,5-b]pyridin-5-ol;
2-methyl-3-p-tolyl-3H-imidazo[4,5-b]pyridin-5-ol;
2-(methylthio)-3-phenyl-3H-imidazo[4,5-b]pyridin-5-ol;
3-o-tolyl-3H-imidazo[4,5-b]pyridin-5-ol;
3-(3,4-dimethylphenyl)-3H-imidazo[4,5-b]pyridin-5-ol;
3-(3,5-dimethylphenyl)-3H-imidazo[4,5-b]pyridin-5-ol;
3-(2,5-dimethylphenyl)-3H-imidazo[4,5-b]pyridin-5-ol;
3-(4-bromophenyl)-2-methyl-3H-imidazo[4,5-b]pyridin-5-ol;
2-amino-3-(4-bromophenyl)-3H-imidazo[4,5-b]pyridin-5-ol;
3-(thiophen-3-yl)-3H-imidazo[4,5-b]pyridin-5-ol;
3-(2-chlorophenyl)-3H-imidazo[4,5-b]pyridin-5-ol;
3-(2-methoxyphenyl)-3H-imidazo[4,5-b]pyridin-5-ol;
3-(4-fluoro-2-methylphenyl)-3H-imidazo[4,5-b]pyridin-5-ol;
3-(2-(trifluoromethyl)phenyl)-3H-imidazo[4,5-b]pyridin-5-ol;
3-(2-fluorophenyl)-3H-imidazo[4,5-b]pyridin-5-ol;
2-amino-3-o-tolyl-3H-imidazo[4,5-b]pyridin-5-ol;
2-chloro-3-phenyl-3H-imidazo[4,5-b]pyridin-5-ol;
3-cyclobutyl-3H-imidazo[4,5-b]pyridin-5-ol;
3-(2,4-dimethylphenyl)-3H-imidazo[4,5-b]pyridin-5-ol;
3-(2,6-dimethylphenyl)-3H-imidazo[4,5-b]pyridin-5-ol;
3-(2-isopropylphenyl)-3H-imidazo[4,5-b]pyridin-5-ol;
3-(2-ethylphenyl)-3H-imidazo[4,5-b]pyridin-5-ol;
3-(4-bromo-2-methylphenyl)-3H-imidazo[4,5-b]pyridin-5-ol;
2-amino-3-(2-(trifluoromethyl)phenyl)-3H-imidazo[4,5-b]pyridin-5-ol;
2-methyl-3-(2-(trifluoromethyl)phenyl)-3H-imidazo[4,5-b]pyridin-5-ol;
3-(biphenyl-2-yl)-3H-imidazo[4,5-b]pyridin-5-ol;
3-(3-chloropyridin-4-yl)-3H-imidazo[4,5-b]pyridin-5-ol;
3-(2-nitrophenyl)-3H-imidazo[4,5-b]pyridin-5-ol;
3-(2-bromophenyl)-3H-imidazo[4,5-b]pyridin-5-ol;
3-(2,6-dichlorophenyl)-3H-imidazo[4,5-b]pyridin-5-ol;
3-(4-bromo-5-chloro-2-methylphenyl)-3H-imidazo[4,5-b]pyridin-5-ol;
3-(5-chloro-2-methylphenyl)-3H-imidazo[4,5-b]pyridin-5-ol;
3-cyclopentyl-3H-imidazo[4,5-b]pyridin-5-ol;
3-cycloheptyl-3H-imidazo[4,5-b]pyridin-5-ol;
3-(2,4-dichlorophenyl)-3H-imidazo[4,5-b]pyridin-5-ol;
3-(3-chloro-2-fluorophenyl)-3H-imidazo[4,5-b]pyridin-5-ol;
3-(2-fluoro-3-(trifluoromethyl)phenyl)-3H-imidazo[4,5-b]pyridin-5-ol;
3-(2,3-dichlorophenyl)-3H-imidazo[4,5-b]pyridin-5-ol;
3-(4-fluoro-2-(trifluoromethyl)phenyl)-3H-imidazo[4,5-b]pyridin-5-ol;
3-(2,3,4-trichlorophenyl)-3H-imidazo[4,5-b]pyridin-5-ol;
3-(2,4-bis(trifluoromethyl)phenyl)-3H-imidazo[4,5-b]pyridin-5-ol;
3-(4-chloro-2-(trifluoromethyl)phenyl)-3H-imidazo[4,5-b]pyridin-5-ol;
3-(4-bromo-2-(trifluoromethyl)phenyl)-3H-imidazo[4,5-b]pyridin-5-ol;
2-amino-3-(2-fluorophenyl)-3H-imidazo[4,5-b]pyridin-5-ol;
3-(2,3-difluorophenyl)-3H-imidazo[4,5-b]pyridin-5-ol;

3-(3-fluoro-2-methylphenyl)-3H-imidazo[4,5-b]pyridin-5-ol;
3-(3-chloro-2-methylphenyl)-3H-imidazo[4,5-b]pyridin-5-ol;
3-(2-chloro-3-fluorophenyl)-3H-imidazo[4,5-b]pyridin-5-ol;
2-amino-3-(2,3-difluorophenyl)-3H-imidazo[4,5-b]pyridin-5-ol;
2-amino-3-(3-fluoro-2-methylphenyl)-3H-imidazo[4,5-b]pyridin-5-ol;
2-amino-3-(3-chloro-2-methylphenyl)-3H-imidazo[4,5-b]pyridin-5-ol;
2-amino-3-(2-chloro-3-fluorophenyl)-3H-imidazo[4,5-b]pyridin-5-ol;
3-(2-fluoro-3-methylphenyl)-3H-imidazo[4,5-b]pyridin-5-ol;
3-(tetrahydro-2H-pyran-4-yl)-3H-imidazo[4,5-b]pyridin-5-ol;
2-chloro-3-(2-chlorophenyl)-3H-imidazo[4,5-b]pyridin-5-ol;
2-(5-hydroxy-3H-imidazo[4,5-b]pyridin-3-yl)cycloheptanone;
3-(2-hydroxycycloheptyl)-3H-imidazo[4,5-b]pyridin-5-ol;
2-amino-3-(2,4,5-trichlorophenyl)-3H-imidazo[4,5-b]pyridin-5-ol;
2-methyl-3-(2,4,5-trichlorophenyl)-3H-imidazo[4,5-b]pyridin-5-ol;
3-(2,4,5-trichlorophenyl)-3H-imidazo[4,5-b]pyridin-5-ol;
3-(4-chloronaphthalen-1-yl)-2-methyl-3H-imidazo[4,5-b]pyridin-5-ol;
3-(4-chloronaphthalen-1-yl)-3H-imidazo[4,5-b]pyridin-5-ol;
3-(2,3-dimethylphenyl)-2-methyl-3H-imidazo[4,5-b]pyridin-5-ol;
3-(2,3-dimethylphenyl)-3H-imidazo[4,5-b]pyridin-5-ol;
3-(2-bromo-3-methylphenyl)-2-methyl-3H-imidazo[4,5-b]pyridin-5-ol;
3-(2-bromo-3-methylphenyl)-3H-imidazo[4,5-b]pyridin-5-ol;
2-methyl-3-(naphthalen-1-yl)-3H-imidazo[4,5-b]pyridin-5-ol;
2-methyl-3-(2,3,4-trichlorophenyl)-3H-imidazo[4,5-b]pyridin-5-ol;
2-amino-3-(2,3,4-trichlorophenyl)-3H-imidazo[4,5-b]pyridin-5-ol;
3-(2-methylnaphthalen-1-yl)-3H-imidazo[4,5-b]pyridin-5-ol;
3-(naphthalen-1-yl)-3H-imidazo[4,5-b]pyridin-5-ol;
2-amino-3-(naphthalen-1-yl)-3H-imidazo[4,5-b]pyridin-5-ol;
2-amino-3-(4-chloronaphthalen-1-yl)-3H-imidazo[4,5-b]pyridin-5-ol;
2-amino-3-(2-methylnaphthalen-1-yl)-3H-imidazo[4,5-b]pyridin-5-ol;
2-methyl-3-(2-methylnaphthalen-1-yl)-3H-imidazo[4,5-b]pyridin-5-ol;
3-(4-hydroxycyclohexyl)-3H-imidazo[4,5-b]pyridin-5-ol;
2-(5-hydroxy-3H-imidazo[4,5-b]pyridin-3-yl)cyclohexanone;
3-cyclohexyl-3H-imidazo[4,5-b]pyridin-5-ol;
2-amino-3-cycloheptyl-3H-imidazo[4,5-b]pyridin-5-ol;
3-cyclooctyl-3H-imidazo[4,5-b]pyridin-5-ol;
3-cycloheptyl-2-methyl-3H-imidazo[4,5-b]pyridin-5-ol;
3-(2-hydroxycyclohexyl)-3H-imidazo[4,5-b]pyridin-5-ol;
3-(tetrahydro-2H-thiopyran-4-yl)-3H-imidazo[4,5-b]pyridin-5-ol;
3-(bicyclo[2.2.1]heptan-2-yl)-3H-imidazo[4,5-b]pyridin-5-ol;
3-(2,3-dihydro-1H-inden-4-yl)-3H-imidazo[4,5-b]pyridin-5-ol;
2-amino-3-(2,3-dihydro-1H-inden-4-yl)-3H-imidazo[4,5-b]pyridin-5-ol;
3-(3-bromo-2-(trifluoromethyl)phenyl)-3H-imidazo[4,5-b]pyridin-5-ol;
2-chloro-3-(2-fluorophenyl)-3H-imidazo[4,5-b]pyridin-5-ol;
2-bromo-3-(2-fluorophenyl)-3H-imidazo[4,5-b]pyridin-5-ol;
tert-butyl 4-(5-hydroxy-3H-imidazo[4,5-b]pyridin-3-yl)azepane-1-carboxylate;
2-bromo-3-(2-chlorophenyl)-3H-imidazo[4,5-b]pyridin-5-ol;
3-(2-cyclopropylphenyl)-3H-imidazo[4,5-b]pyridin-5-ol;
3-(2-(trifluoromethoxy)phenyl)-3H-imidazo[4,5-b]pyridin-5-ol;
2-methyl-3-(2-(trifluoromethoxy)phenyl)-3H-imidazo[4,5-b]pyridin-5-ol;
2-amino-3-(2-(trifluoromethoxy)phenyl)-3H-imidazo[4,5-b]pyridin-5-ol;
2-methyl-3-(2-(methylthio)phenyl)-3H-imidazo[4,5-b]pyridin-5-ol;
3-(3-fluoro-2-(trifluoromethyl)phenyl)-3H imidazo[4,5-b]pyridin-5-ol;
3-(2-chlorophenyl)-2-methyl-3H-imidazo[4,5-b]pyridin-5-ol;
2-amino-3-(2-chlorophenyl)-3H-imidazo[4,5-b]pyridin-5-ol;
3-(adamant-1-yl)-3H-imidazo[4,5-b]pyridin-5-ol;
3-(adamant-1-yl)-2-methyl-3H-imidazo[4,5-b]pyridin-5-ol;
3-(adamant-1-yl)-2-amino-3H-imidazo[4,5-b]pyridin-5-ol;
3-(2-fluorophenyl)-2-methyl-3H-imidazo[4,5-b]pyridin-5-ol;
3-(2,2-difluorocycloheptyl)-3H-imidazo[4,5-b]pyridin-5-ol;
3-(2-methylcyclohexyl)-3H-imidazo[4,5-b]pyridin-5-ol;
3-(2-chlorophenyl)-2-cyclopropyl-3H-imidazo[4,5-b]pyridin-5-ol;
3-(2-(trifluoromethylthio)phenyl)-3H-imidazo[4,5-b]pyridin-5-ol;
2-methyl-3-(2-(trifluoromethylthio)phenyl)-3H-imidazo[4,5-b]pyridin-5-ol;
2-amino-3-(2-(trifluoromethylthio)phenyl)-3H-imidazo[4,5-b]pyridin-5-ol;
2-cyclopropyl-3-(2-(trifluoromethoxy)phenyl)-3H-imidazo[4,5-b]pyridin-5-ol;
2-chloro-3-(2-(trifluoromethoxy)phenyl)-3H-imidazo[4,5-b]pyridin-5-ol;
3-cyclohexyl-2-methyl-3H-imidazo[4,5-b]pyridin-5-ol;
2-chloro-3-cyclohexyl-3H-imidazo[4,5-b]pyridin-5-ol;
3-(2-bromophenyl)-2-methyl-3H-imidazo[4,5-b]pyridin-5-ol;
3-(2-bromophenyl)-2-chloro-3H-imidazo[4,5-b]pyridin-5-ol;
2-bromo-3-(2-bromophenyl)-3H-imidazo[4,5-b]pyridin-5-ol;
2-chloro-3-(2-(trifluoromethyl)phenyl)-3H-imidazo[4,5-b]pyridin-5-ol;
2-chloro-3-(2-(trifluoromethylthio)phenyl)-3H-imidazo[4,5-b]pyridin-5-ol;
2-chloro-3-(2-cyclopropylphenyl)-3H-imidazo[4,5-b]pyridin-5-ol;

2-chloro-3-o-tolyl-3H-imidazo[4,5-b]pyridin-5-ol;
2-bromo-3-o-tolyl-3H-imidazo[4,5-b]pyridin-5-ol;
3-(bicyclo[2.2.1]heptan-2-yl)-2-chloro-3H-imidazo[4,5-b]pyridin-5-ol;
3-(1-methylcyclohexyl)-3H-imidazo[4,5-b]pyridin-5-ol;
2-chloro-3-(2-methylcyclohexyl)-3H-imidazo[4,5-b]pyridin-5-ol;
3-(1-ethylcyclohexyl)-2-methyl-3H-imidazo[4,5-b]pyridin-5-ol; and
2-methyl-3-(1-methylcyclohexyl)-3H-imidazo[4,5-b]pyridin-5-ol.

25. A pharmaceutical composition comprising a compound according to claim 1 and a pharmaceutically acceptable carrier.

26. A process for preparing a pharmaceutical composition comprising admixing a compound according to claim 1 and a pharmaceutically acceptable carrier.

* * * * *